United States Patent
Portugal et al.

(10) Patent No.: US 10,370,442 B2
(45) Date of Patent: Aug. 6, 2019

(54) VNAR RECOMBINANT MONOCLONAL ANTIBODIES THAT NEUTRALIZE VASCULAR ENDOPHELIAL GROWTH FACTOR VEGF

(71) Applicant: TERACLON IDF, S.L., Madrid (ES)

(72) Inventors: Carolina Elosua Portugal, Cobena (ES); Maria Teresa Mata Gonzalez, Coyoacan (MX); Tanya Amanda Camacho Villegas, Ensenada (MX); Araceli Olguin Jimenez, Tlalpan (MX); Alexei Fedorovish Licea Navarro, Ensenada (MX); Jorge Fernando Paniagua Solis, Vaud (CH)

(73) Assignee: TERACLON IDF, S.L., Madrid (ES)

( * ) Notice: Subject to any disclaimer, the term of this patent is extended or adjusted under 35 U.S.C. 154(b) by 0 days.

(21) Appl. No.: 15/304,516

(22) PCT Filed: Apr. 17, 2014

(86) PCT No.: PCT/ES2014/070332
§ 371 (c)(1),
(2) Date: Oct. 15, 2016

(87) PCT Pub. No.: WO2015/158937
PCT Pub. Date: Oct. 22, 2015

(65) Prior Publication Data
US 2017/0137504 A1    May 18, 2017

(51) Int. Cl.
*C07K 16/22* (2006.01)
(52) U.S. Cl.
CPC .......... *C07K 16/22* (2013.01); *C07K 2317/20* (2013.01); *C07K 2317/569* (2013.01); *C07K 2317/76* (2013.01)
(58) Field of Classification Search
CPC .............. C07K 16/22; C07K 2317/569; C07K 2317/76; C07K 2317/22; A61K 2039/505
See application file for complete search history.

(56) References Cited

U.S. PATENT DOCUMENTS 8,496,933 B2    7/2013  Paniagua-Solis et al.

FOREIGN PATENT DOCUMENTS

WO    WO 2005/118629    12/2005
WO    WO 2010/040175    4/2010

OTHER PUBLICATIONS

Yu et al., Investigative Ophthalmology & Visual Science 49(2): 522-527, Feb. 2008.*
Cohen et al., Retina 32: 1480-1485, 2012.*
Nuttall S D et al: "Isolation of the New Antigen Receptor From Wobbegong Sharks, and Use as a Scaffold for the Display of Protein Loop Libraries", Molecular Immunology . . . .
. . . Pergamon, GB, vol. 38, No. 4, Aug. 1, 2001: ISSN: 0161-5890, DOI: 10.1016/S0161-5890(01)00057-8.
Dooley H et al: "Selection and characterization of naturally occurring single-domain (IgNAR) antibody fragments from immunized sharks by phage display" Molecular IMMUNOLOGy . . . .
. . . Pergamon, GB, vol. 40, No. 1, Sep. 1, 2003, pp. 25-33, XP003013541, ISSN: 0161-5890, DOI: 10.1016/S0161-5890(03)00084-1.
Janusz Wesolowshi et al: "Single domain antibodies: promising experimental and therapeutic tools in infection and immunity", Medical Microbiology and Immunology, Springer . . . .
. . . Berlin, DE, vol. 198, No. 3, Jun. 16, 2009, pp. 157-174, XP019740594, ISSN: 1432-1831, DOI: 10.1007/S00430-009-0116-7.
Witamer A N et al: "VascularEndothelial Growth Factors and Angiogenesis in eye Disease," Progress in Retinal and Eye Research, Oxford, GB; vol. 22, No. 1, Jan. 1, 2003 . . . .
. . . pp. 1-29, XP009050003, ISSN: 1350-9462, DOI: 10.1016/S1350-9462 (02)00043-5.

* cited by examiner

*Primary Examiner* — Phuong Huynh
(74) *Attorney, Agent, or Firm* — Hill Wallack LLP

(57) ABSTRACT

The present invention refers to the selection, isolation and purification of proteins belonging to variable regions named $V_HNAR$ or vNAR, originated from IgNAR-type immunoglobulins of elasmobranches with antigen receptor abilities. The clones from which they originate are named VEGFv-NAR V32R and V19; and the antibodies are named V32R and V19. Their amino acid sequences and tertiary structures were elucidated, and their ability to neutralize the vascular endothelial growth factor (VEGF) activity was determined. During the development of the invention these proteins were optimized for expression in a production model of *E. coli* at industrial level. The invention involves the use of these antibodies in general to treat conditions related to angiogenesis or neovascularization and in particular to treat neovascularization-related ophthalmic conditions by topical administration.

19 Claims, 68 Drawing Sheets

Specification includes a Sequence Listing.

FIG. 1

ASLDQTPRTA TRETGESLSI NCVLTDTSHI LFGTKWLWNN PGSTDWESIT
IGGRYAESVN NQAKSFSLQI KDLTVEDSGT YYCKAQTIGR RKNLLPRPLV NGIAAMGYSS
SDYDGAGTVL TVN

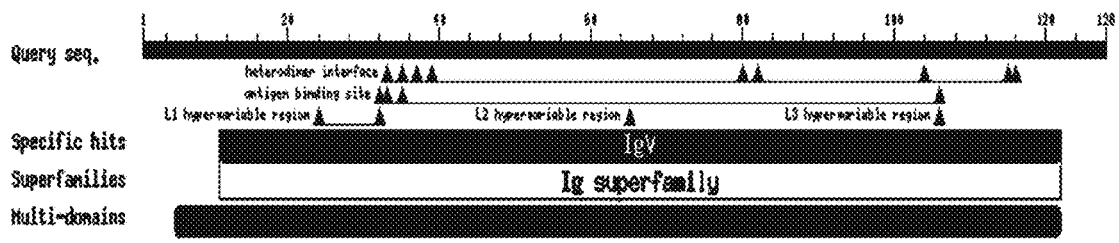

FIG. 2

```
v13    -MASLDQTPRTATRETGESLSINCVLTDTSHILFGTKWLWNNPGSTDWESITIGGRYAES
v32R   MAASLDQTPRTATRETGESLTINCVFTDSSCGLCGTSWFRNMPGSTDWERITIGGRYVES
v19    MAQRVEQTPRTATKETGESLTINCVLRDASFELKDTGWYRTRLGSTNEQSISIGGRYVET
        ;:*******;******;****;  *;*   *  .* *   .;  ***;  ; *;*****.*;

v13    VNNQAKSFSLQIKDLTVEDSGTYYCKAQTIGRRKNLLPRPLVNGIAAMGYSSSD--YDGA
v32R   VNKGAKSFSLQIKDLTVEDSVTYYCKAQ--GHR-------YFSKVCELRCPSYY--YDGA
v19    VNKGSKSFSLRISDLRVEDSGTYKCQAF------------YSLPLGDYMYSLLFRGEKGA
        **; ;*****;*.** **** ** *;*                 :      .    .**

v13    GTVLTVN
v32R   GTVLTVN
v19    GTVLTVN
        *******
```

| pET-20b(+) sequence landmarks | |
|---|---|
| T7 promoter | 353-369 |
| T7 transcription start | 352 |
| pelB coding sequence | 224-289 |
| Multiple cloning sites (Nco I - Xho I) | 158-225 |
| His•Tag coding sequence | 140-157 |
| T7 terminator | 26-72 |
| pBR322 origin | 1500 |
| bla coding sequence | 2261-3118 |
| f1 origin | 3250-3705 |

FIG. 3A (continued)

| pET-28a(+) sequence landmarks | |
| --- | --- |
| T7 promoter | 370-386 |
| T7 transcription start | 369 |
| His•Tag coding sequence | 270-287 |
| T7•Tag coding sequence | 207-239 |
| Multiple cloning sites (BamH I - Xho I) | 158-203 |
| His•Tag coding sequence | 140-157 |
| T7 terminator | 26-72 |
| lacI coding sequence | 773-1852 |
| pBR322 origin | 3286 |
| Kan coding sequence | 3995-4807 |
| f1 origin | 4903-5358 |

The maps for pET-28b(+) and pET-28c(+) are the same as pET-28a(+) (shown) with the following exceptions: pET-28b(+) is a 5368bp plasmid: subtract 1bp from each site beyond BamH I at 198. pET-28c(+) is a 5367bp plasmid: subtract 2bp from each site beyond BamH I at 198.

FIG. 3B (continued)

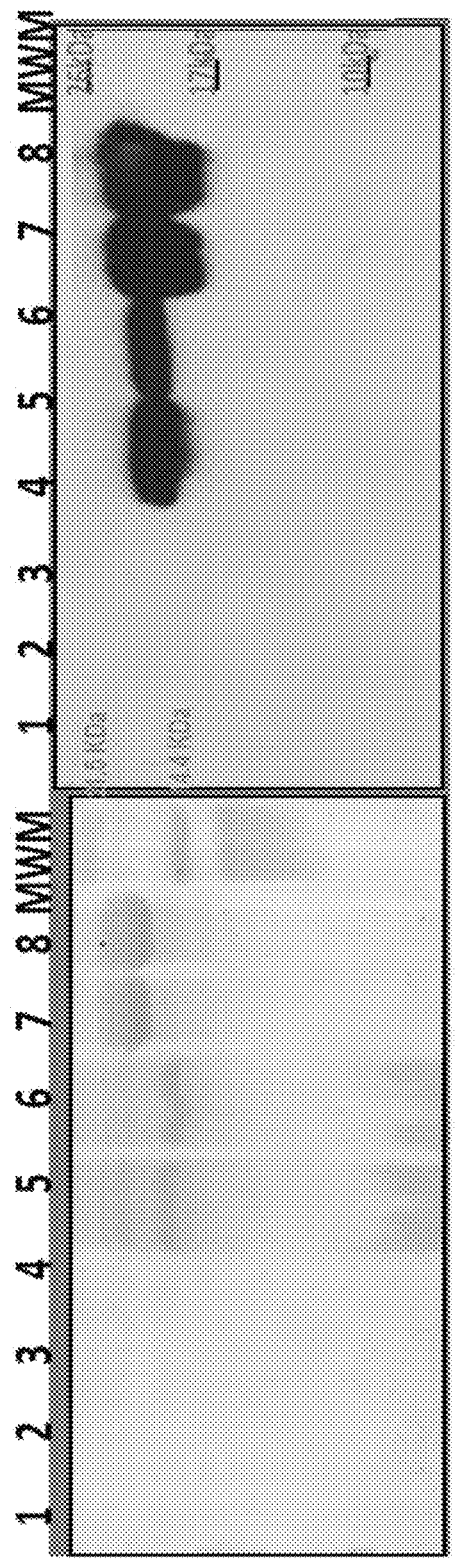

FIG. 14A
FIG. 14B
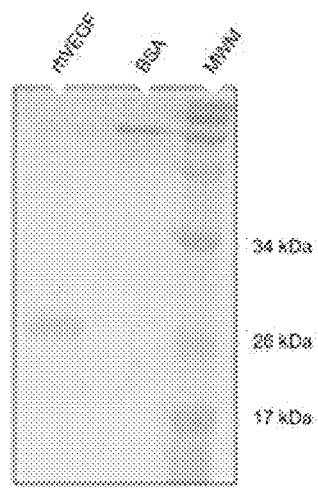
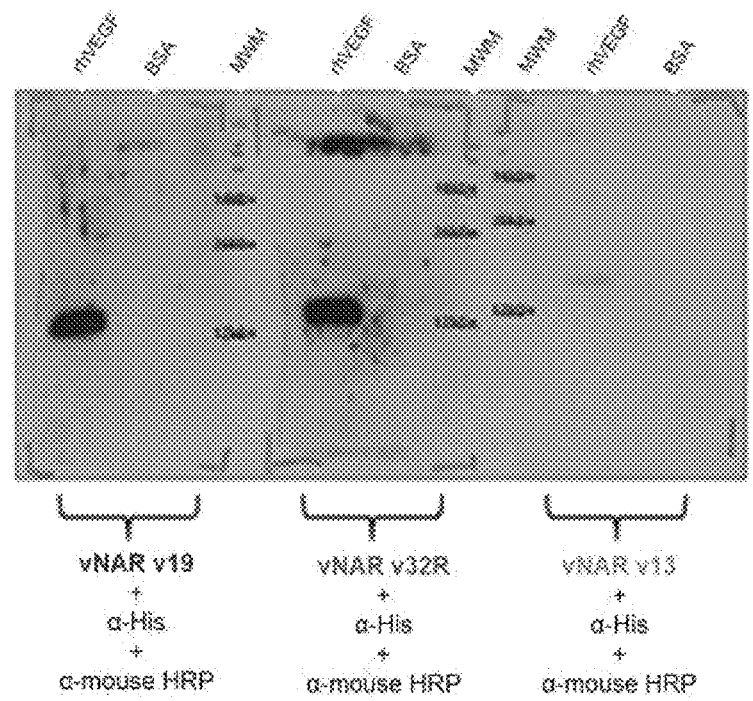

FIG. 29
FIG. 30

FIG. 36
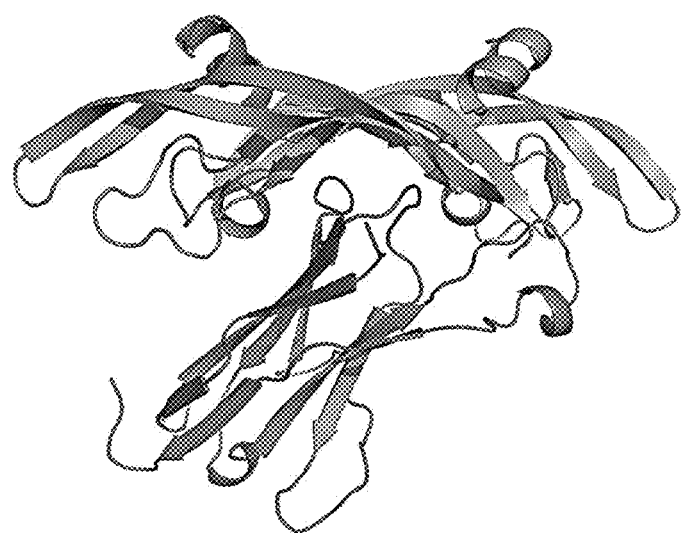
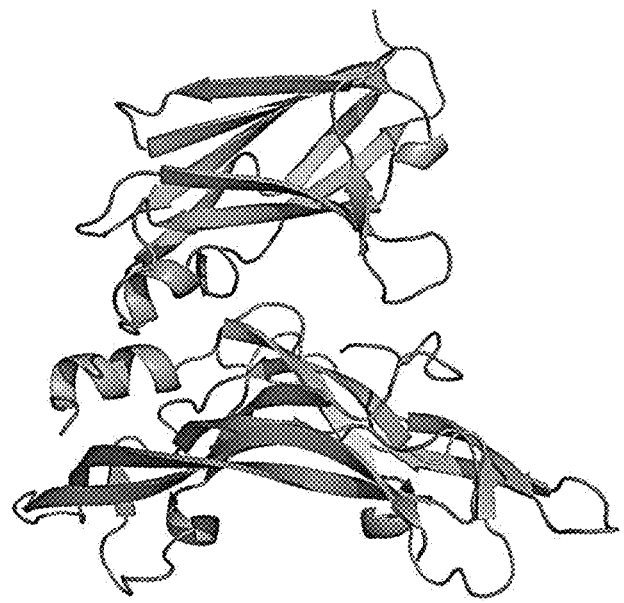
FIG. 37

|   | 1 | 2 | 3 | 4 | 5 | 6 | 7 | 8 | 9 | 10 | 11 | 12 |
|---|---|---|---|---|---|---|---|---|---|----|----|----|
| A | VEGF 4 ng/mL Suramin 100 μM | VEGF 4 ng/mL | VEGF 4 ng/mL vNAR 0.59 μg/mL | VEGF 4 ng/mL vNAR 1.17 μg/mL | VEGF 4 ng/mL vNAR 2.34 μg/mL | VEGF 4 ng/mL vNAR 4.69 μg/mL | VEGF 4 ng/mL vNAR 9.38 μg/mL | VEGF 4 ng/mL vNAR 18.75 μg/mL | VEGF 4 ng/mL vNAR 37.5 μg/mL | VEGF 4 ng/mL vNAR 75 μg/mL | VEGF 4 ng/mL vNAR 150 μg/mL | VEGF 4 ng/mL vNAR 300 μg/mL |
| B | | | | | | | | | | | | |
| C | | | | | | | | | | | | |
| D | | | | | | | | | | | | |
| E | Control without treatment | VEGF 4 ng/mL Buffer | VEGF 4 ng/mL vNAR 0.59 μg/mL | VEGF 4 ng/mL vNAR 1.17 μg/mL | VEGF 4 ng/mL vNAR 2.34 μg/mL | VEGF 4 ng/mL vNAR 4.69 μg/mL | VEGF 4 ng/mL vNAR 9.38 μg/mL | VEGF 4 ng/mL vNAR 18.75 μg/mL | VEGF 4 ng/mL vNAR 37.5 μg/mL | VEGF 4 ng/mL vNAR 75 μg/mL | VEGF 4 ng/mL vNAR 150 μg/mL | VEGF 4 ng/mL vNAR 300 μg/mL |
| F | | | | | | | | | | | | |
| G | | | | | | | | | | | | |
| H | | | | | | | | | | | | |

FIG. 50

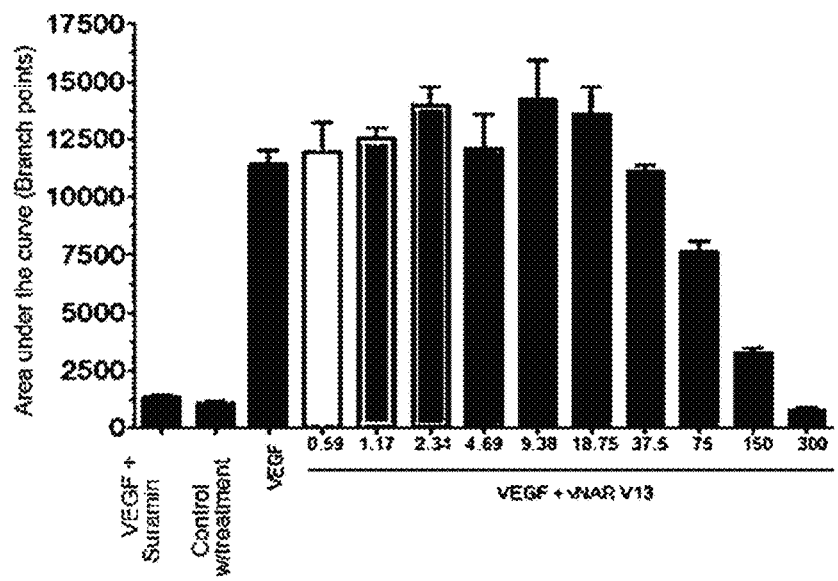
FIG. 52B
FIG. 52C
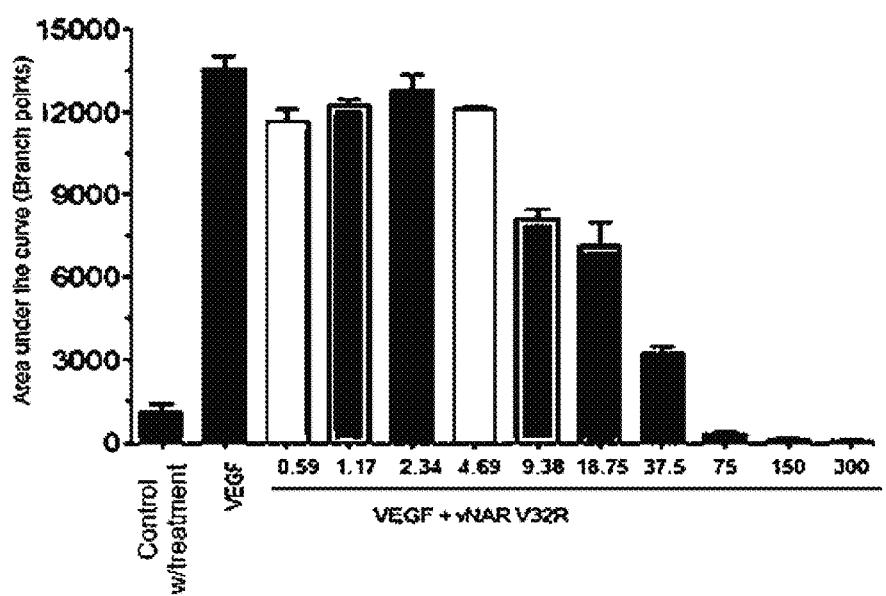

VNAR RECOMBINANT MONOCLONAL ANTIBODIES THAT NEUTRALIZE VASCULAR ENDOPHELIAL GROWTH FACTOR VEGF

FIELD OF THE INVENTION

The present invention refers to the biotechnology field, specifically to the generation of shark-based monoclonal antibodies biopharmaceuticals named vNAR that block the vascular endothelial growth factor (VEGF) and possess remarkable biological and biophysical properties. The vNAR antibodies are highly resistant to environmental conditions and may not require a cold chain. Moreover, they have a good penetration capacity, thus increasing their therapeutic activity.

BACKGROUND OF THE INVENTION

Antibodies are important tools for medical applications. Most antibodies are composed of two heavy and two light chains, both chains form the antigen binding site. Non-conventional antibody structures have been found in llamas, camels, and cartilaginous fishes. These antibodies consist of a single heavy chain with four constant domains and an antigen binding site or variable domain denominated $V_HH$, hcAbs in camels and vNAR or $V_HNAR$ in elasmobranches.[1]

Antibody technology has been developed to provide new therapies and diagnostic systems. It includes, for example, the use of monoclonal antibodies; humanized antibodies, designed to decrease the non-human antigen response; and conjugated antibodies, to improve their properties. The number of antibodies approved by FDA for the treatment of several human diseases has been increasing, approximately 352 of them are on clinical trials (phase I and phase II), accounting for around 25% of all the proteins on clinical trials. A lot of effort has been done in order to reduce the conventional size of antibodies and preserving their antigen binding properties like affinity, avidity and specificity.[2]

Small fragments of antibodies with antigen binding ability are among the technologic alternatives for medical use. Such alternatives have progressed from recombinant molecules, like the fragment of antigen binding (Fab) and/or the single chain variable fragment (scFv), to single binding domains for proteins based on immunoglobulins with $V_H$ domains, which in turn have been used to develop new immunotherapeutic and immunodiagnostic strategies. Mimetics of the Fab's to smaller domains is advantageous since that increases the stability and the possibility for accessing antigenic epitopes that are not recognized by conventional antibodies.[2]

There are three isotypes of immunoglobulins or antibodies from cartilaginous fishes, two of them with two standard heavy and light chains, designated as IgM and IgW (also called IgX or IgNARC) and one atypical isotope called IgNAR which is a homodimer of heavy chains not associated with light chains. The shark antigen receptor immunoglobulins (referred as IgNAR or NAR) have a single variable domain (sdAb fragments) and two fork hypervariable structures to include the entire repertoire with union specificity to recognize the antigens. IgNARs are high soluble and high thermostable small molecules (12 kDa) and with good tissue penetration in vivo, which makes IgNARs a good resource for antibody engineering and therapeutic antibodies.[3,4]

The present invention concerns to selection and isolation of IgNAR antibodies, in particular of its variable region $V_HNAR$, originated in the immunized shark *Heterodontus francisci* or *Orectolobus maculatus* with affinity for cytokines and ability to neutralize their activity. These antibodies are originated generally by the immunological system of cartilaginous fish (sharks, skates, rays, and chimeras). The molecular arrangement of the IgNAR antibodies consists of five constant regions and one variable region which in addition is very similar to the $V_H$ found in camelids, which possibly represents an evolutionary convergence at molecular level.[1,5]

Nuttall and collaborators obtained a non-immune shark antibody library, through phage display technology based on variable regions of IgNAR of the shark *Orectolobus maculatus*. These regions have the ability to recognize proteins like gingipain K protease from *Porphyromonas gingivalis*, the mitochondrial import receptor Tom70, the lysozyme and the Apical Membrane Antigen 1 (AMA1) of *Plasmodium falciparum*, among others. These regions have been cloned in *Escherichia coli* expression systems, being the first description of antigenic specificity of NARs obtained from the natural repertoire of the shark as a probable source of high affinity single domain antibodies.[6,7,8]

Dooley and collaborators in 2003 selected a targeted library generated in *Ginglymostoma cirratum*. These sharks were immunized with hen egg lysozyme (HEL), resulting in highly specific clones to HEL antigen, with a nanomolar affinity (ranging from $10^{-7}$ to $10^{-10}$ M) and with a great resistance to heat denaturalization, since they maintained more than 20% of its activity after 3 hrs of incubation at 100° C.[9]

The genes of IgNAR are grouped; each group consists of a single variable simple region (VH), three elements of diversity (D) and a single joining gene (J). The primary repertoire of IgNAR $V_H$ is generated by four recombination events, resulting in a diverse repertoire of CDR3 both in terms of sequence and length.[6]

Different technologies with shark proteins were developed immediately after the discovery of these single chain antigen receptors due to their high functionality. The isolated and cloned variable domain is very stable; it is 20% smaller than the domain of camelid antibodies and it possesses the same antigen binding ability than the original receptor.

The advantage of this technology is that it combines the properties of the conventional antibodies with the advantages of the small molecules; they have high specificity and low inherent toxicity; due to their low molecular weight they have more possibilities to reach their target site; they are capable of inhibiting enzymes and they can also reach the binding site of cell receptors. All these properties can be exploited for therapeutic uses. Additionally, they have a great potential for being administered by diverse routes, including the topical route. Finally, their production is easy and at low cost.[5]

From the literature it is clear that overexpression of VEGF and their receptors (VEGFR-1, VEGFR-2 and VEGFR-3) is causing increased microvascular permeability and angiogenesis, producing eye pathologies such as diabetic retinopathy, age-related macular degeneration (ARMD), and neovascular glaucoma. The cellular distribution of VEGFR-1, VEGFR-2 and VEGFR-3 receptors suggests various specific functions of the VEGF family in normal retina, both in the retinal vasculature and in neuronal elements.[10]

The vascular endothelial growth factor (VEGF) has been described as a tumor-derived factor with the ability to induce endothelial cell permeability, cell proliferation and angiogenesis, which defines formation of new blood vessels, especially those providing oxygen and nutrients to cancerous tissues. Although many other factors are involved in angiogenesis, VEGF is the key mediator.

The VEGF (or VEGF-A) is a heparin-binding glycoprotein that belongs to a subfamily of growth factors that includes VEGF-B, VEGF-C, VEGF-D and platelet growth factor. As a result of alternative splicing patterns of VEGF mRNA, VEGF exists in at least seven isoforms. The four major isoforms are $VEGF_{121}$, $VEGF_{165}$, $VEGF_{189}$ and $VEGF_{206}$ (the subscripts refer to the number of amino acids of the protein). The predominant species is $VEGF_{165}$ with an affinity for heparin; therefore, part of this isoform is bound and is released by proteolytic cleavage. The rest is free and available for binding to receptors on endothelial cells and it is the result of two distinct processes: the secretion of soluble isoforms and the proteolytic cleavage of bound isoforms. The physiological importance of the different isoforms of VEGF is not clear; however the $VEGF_{165}$ is the major regulator of angiogenesis.

The VEGF binds mainly to two receptors: VEGF receptor-1 (also known as Flt-1) and VEGF receptor-2 (also known as Flk-1 or KDR). Each of these receptors has an extracellular domain (which binds VEGF) with seven immunoglobulin-type areas, a single transmembrane region and an intracellular domain with tyrosine kinase activity. These receptors are mainly found in vascular endothelial cells of developing tissues.

Binding to VEGF receptor-2, directly stimulates angiogenesis and activates a series of signal transduction pathways resulting in the proliferation of vascular endothelial cells, migration of vascular endothelial cells, survival of immature endothelial cells and increased vascular permeability.

Although VEGF receptor-1 was initially thought to act as a "decoy receptor" by reducing the number of molecules of VEGF capable of binding to VEGF receptor-2, recent studies show that VEGF receptor-1 is also capable of inducing a mitogenic signal.

Angiogenesis is the formation of new vascular structures and plays a key role in pathological processes such as the establishment of tumors and eye diseases. Diabetic retinopathy is known as the abnormal growth of new blood vessels and the appearance of fibrous tissue in the retina; when originating beneath the macula it is called Macular Degeneration; and when it is occurs in the iris it is called Neovascular Glaucoma.

Diabetic retinopathy is a condition of the retina that occurs in patients with diabetes mellitus; both type 1 and type 2 after several years of having the disease, especially when the disease is not well controlled. There are two types of diabetic retinopathy: early or non-proliferative diabetic retinopathy and proliferative or advanced diabetic retinopathy. The proliferative diabetic retinopathy is characterized by the abnormal growth of new vessels and subsequent fibrous proliferation in response to retinal ischemia as well as the development of pre-retinal or vitreous hemorrhage.[11] Its importance lies in the fact that it is one of the leading causes of irreversible blindness worldwide and that it can be prevented by taking the proper precautions and applying timely treatment.[11] Diabetic retinopathy is defined as the presence and evolution of typical ocular microvascular injuries in diabetic patients.

Age-related macular degeneration is the leading cause of visual loss in patients over 60 years. The macula is the central area of the retina, and it is responsible of the fine vision used for reading, watching television, see the factions of people and in general the vision of any fine details.[12] The ARMD is a degenerative condition of the macula, which is a common cause of vision loss. It can be classified as wet (neovascular) or dry (non-neovascular). About 10% of the patients suffer from wet macular degeneration. Usual treatment of wet macular degeneration involves the application of one or several injections of medicines within the eye called "antiangiogenics", whose intention is to remove the neovascular membrane. With this treatment, over 90% of patients achieved to maintain vision, and approximately two thirds of patients improved vision, as long as the treatment is applied in a timely manner and not much scarring occurs.

There is the development of new blood vessels in those tissues where the circulation is either damaged through trauma or disease such as those mentioned above. Corneal neovascularization is the abnormal growth of blood vessels causing choriocapillaries passing through Bruch's membrane and then proliferate under the retinal pigment epithelium (type 1) and/or under the retina (type 2). This can occur by rupture of Bruch's membrane, the release of cytokines such as VEGF, inflammation, oxidative stress in the retinal pigment epithelium or vascular insufficiency. This condition is the leading cause of wet macular degeneration and may be associated with various disorders including angioid streaks, choroidal rupture, pathological myopia, chorioretinal lesion and birdshot chorioretinopathy.

There is also the phenomenon of iris neovascularization. The abnormal formation of new blood vessels on the anterior surface of the iris is commonly associated with different conditions which have led to retinal ischemia, such as diabetic retinopathy, central retinal vein occlusion, carotid artery disease, melanoma uveal, prolonged retinal detachment, etc. Neovascularization begins in the pupil margins and often at the same time at the angle of the anterior chamber and spreading over the entire surface. The new vessels are associated with fibrous tissue membranes, which can block the pass of aqueous humor through the trabecular meshwork (neovascular glaucoma) and cause ectropion uveae in the pupillary border. Its usual treatment consists of applying laser photocoagulation to prevent the formation of new blood vessels.

Neovascular glaucoma is a special type of secondary glaucoma occurring as a consequence of the formation of new blood vessels in the iris. These new vessels eventually cause a blockage in the circulation of aqueous humor from the anterior chamber of the eye, which triggers an ocular hypertension. It results from a lack of chronic and maintained retinal oxygen. In response thereto the system produces a number of substances that stimulate neovascularization.

Other pathological processes where the phenomenon of neovascularization is involved are: Retinal Neovascularization, Choroidal Neovascularization, Corneal Neovascularization, Macular Degeneration, Age-Related Macular Degeneration, Retinal Diseases, Diabetic Retinopathy, Vitreous Hemorrhage, Retinal Hemorrhage, Choroiditis, Retinal Detachment, Retinal Drusen, Neovascular Glaucoma, Choroid Diseases, Uveitis, Myopia, Eye Diseases, Fungal Eye Infections, Telangiectasia, Retinal Artery Occlusion, Degenerative Myopia, Retinal Vein Occlusion, Chorioretinitis, Histoplasmosis, Uveal Diseases, Rubella (German Measles), Ocular Toxoplasmosis, Epiretinal Membrane, Coloboma, Choroid Neoplasms, Retinal Degeneration, Retinitis, Retinal Perforations, Herpetic Keratitis, Retinopathy of Prematurity, Cystoid Macular Edema, Papilledema, Uveomeningoencephalitic Syndrome, Optic Disk Drusen, Angioid Streaks, Retinitis Pigmentosa, Vision Disorders, Sympathetic Ophthalmia, Scar, Ocular Burns, Recurrent Ischemia, Eye Injuries, Glaucoma, Eye Hemorrhage, Scotoma, Posterior Uveitis, Fungemia, Retinal Neoplasms, Corneal Diseases, Pigmentary Incontinence, Hemoglobin C Disease, Fibrosis, Opacity of the Cornea, Anterior Uveitis, Hyphema, Sarcoidosis, Aphakia, Iatrogenic Disease, Panuveitis, Eye Cataract, Postoperative Complications, Sickle Cell Anemia, Retinal Vasculitis, Osteoma, Cytomegalovirus Retinitis, Atrophy, Phlebitis, Keratoconus, Sturge-Weber Syndrome, Viral Eye Infections, Eye Abnormalities, Substance-Related Disorders, Penetrating Eye Injuries, Diabetes Mellitus Type 2, Radiation Injuries, Sickle Cell Trait, Pseudophakia, Pigmented Nevus, Proliferative Vitreoretinopathy, Bleeding, Diabetes Mellitus Type 1, Nevus, Optic Nerve Diseases, Vascular Diseases, Candidiasis, Chemical Burns, Microphthalmia.

Worldwide, 285 million people have visual impairment from various causes, and 39 million of them are blind.[14] "The main causes of chronic blindness include cataract, glaucoma, age-related macular degeneration, corneal opacities, diabetic retinopathy, trachoma and eye conditions in children as well as those caused by lack of vitamin A. The age-related blindness as well as due to uncontrolled diabetes is increasing worldwide. Three quarters of all blindness cases are preventable or treatable".[15]

The inhibitory molecules of VEGF activity may be used to limit neovascularization processes which depend upon VEGF action.

The anti-VEGF antibodies bind to the ligand, thus eliminating free-circulating VEGF and preventing its binding to its receptors. Antibodies have been used for this purpose since they are highly specific and only bind to VEGF; the pro-angiogenic effects mediated by all receptors binding to VEGF can be inhibited. Different strategies have been developed to inhibit VEGF-mediated signaling, however, since it showed that a specific anti-VEGF antibody could inhibit tumor growth in animal models described by Ferrara and Davis-Smith, in 1997 began the development of a human version of anti-VEGF antibody.

Bevacizumab is an anti-VEGF monoclonal antibody. This has been the first anti-angiogenic agent approved for cancer treatment; it has been approved for use as a first-line treatment of metastatic colorectal cancer in combination with a chemotherapy regimen. It has been tested in cancers of many organs with positive clinical outcomes including tumor regression and increased medium to long-term survival rate.[16]

In 2004, the FDA accepted the Pegaptanib, the first antiangiogenic drug for the eye administered by intravitreal injection. This anti-VEGF was analyzed in studies of patients with age-related macular degeneration. The results showed stabilization of vision in 70% of treated patients, versus 50% in patients not treated with this antibody.

In 2006, the FDA approved the use of ophthalmic Ranibizumab, which is a recombinant Fab fragment of anti-VEGF humanized murine monoclonal antibody; it has also been used successfully in the treatment of eye diseases for the inhibition of neovascularization that leads to blindness, especially for treating macular degeneration in all its forms, particularly wet ARMD.[17]

The application route of Ranibizumab is intravitreal injection. However, retinal detachment and serious infections are among the side effects caused by Ranibizumab. It has been reported that in mouse it causes the death of photoreceptors and Müller cells of the retina, which are essential for visual function.

Other ophthalmic drugs that act by inhibiting the activity of the VEGF, and intraocularly administered, are the following: the Verteporfin, used as a selective treatment of choroidal neovascularization associated with macular degeneration; Aflibercept which is used to treat wet age-related macular degeneration, and dexamethasone, corticosteroid which has shown to reduce the inflammatory process causing the macular edema when applied as an intravitreal implant.

U.S. Pat. No. 8,496,933, Paniagua-Solis et al., refers to the selection, isolation and production of a protein belonging to variable regions named $V_H$NAR or vNAR, originated from IgNAR-type immunoglobulins of elasmobranches with antigen receptor abilities. This vNAR was named V13 and it was selected by its capacity to bind specifically to the vascular endothelial growth factor (VEGF). It works by neutralizing the activity of VEGF, and it has been characterized by its sequence, selected and optimized, and which is the closest state of the art to the invention, incorporated herein by reference in its entirety.

The trials on anti-VEGF therapies have tried a variety of dosing strategies such as: when to start treatment, dosing frequency, and how these strategies can be followed in medical treatment, since secondary or side effects as hypertension, proteinuria, bleeding, damage to the healing of surgical wounds, even fatal complications such as arterial thrombosis, gastrointestinal perforation and reversible posterior focal leukoencephalopathy, route of administration, the invasiveness of the methods, the high dose, bioavailability, instability as well as high costs, long treatments, among others, lead to the need of research for new molecules that have better performance. Even with such alternatives, it is required to develop better drugs that inhibit the activity of VEGF for eye treatments in order to remove or reduce side effects.

The present invention describes novel clones and molecules named V19, V32R and the aforementioned V13, characterized by their three-dimensional structure, their sequences and affinities to VEGF and useful in treating eye conditions, particularly for the treatment of diabetic retinopathy, macular degeneration, neovascular glaucoma or ocular conditions related to angiogenesis.

SUMMARY OF THE INVENTION

The present invention refers to the generation of shark-based therapeutic monoclonal antibodies known as IgNARs which are comprised of heavy chains of immunoglobulins. Specifically the present invention relates to the selection of the variable domains (vNARs) of these heavy chains. In this case, they are characterized by their ability to recognize the cytokine known as vascular endothelial growth factor (VEGF). The vNARs are of interest in the field of biotechnology due to their biological and biophysical properties. The vNAR antibodies are highly resistant to environmental conditions and have a high capacity for topical therapeutic action. Together with the variable domains derived from camel immunoglobulin (known as $V_H$H), the vNARs are the smallest biological molecules capable of recognizing antigens. Due to these properties the vNARs outweigh the disadvantages and drawbacks of conventional therapy with monoclonal antibodies.

Moreover, the present invention refers to the selection, isolation and purification of proteins belonging to variable regions named $V_H$NAR or vNAR, originated from IgNAR-type immunoglobulins of elasmobranches with antigen receptor abilities. The clones from which they originate are named VEGFvNAR V32R and V19; and the antibodies are named V32R and V19 (also defined as either v19 or v32R).

The present invention describes new clones and molecules named V19, V32R and the aforementioned V13, characterized by their three-dimensional structure, their sequences and affinities to VEGF and useful in treating eye conditions, particularly for the treatment of diabetic retinopathy, macular degeneration, neovascular glaucoma or ocular conditions related to angiogenesis.

In order to demonstrate that the new clones are not a laboratory artifice and that they actually comprise differential antibodies that provide a surprising and unexpected technical advantage over the prior art, the characterization of the clone V13 has also been included herein—previously described in U.S. Pat. No. 8,496,933—and it has been subjected to the same isolation and purification protocols performed in the development of the invention in order to compare the results. Moreover, in order to improve yields, different tests and methods of expression and purification were carried out during the development of the invention in order to detect and get the best conditions for expression and purification of proteins, as well as the subsequent assessment on the performance of each of the obtained clones to bind and neutralize VEGF.

BRIEF DESCRIPTION OF FIGURES

FIG. 1: Amino acid sequence of the protein anti-VEGF vNAR V13, indicating where the supposed conserved domains were detected.

FIG. 2: Alignment between the sequences corresponding to the clones V13, V32R y V19.

FIG. 8: Analysis of subcellular fractions detection of VEGFvNAR v19 without signal peptide: A: SDS PAGE 15% acrylamide reducing conditions, staining with Coomasie blue. B: Electroblotted to nitrocellulose membrane, hybridization with anti-His (1:3000) plus anti-mouse secondary antibody conjugated to peroxidase (1:3000). Revealed by ECL. Samples per lane: 1) VEGFvNAR v19 extracellular fraction 30° C., 2) VEGFvNAR v19 extracellular fraction 30° C., 3) VEGFvNAR v19 periplasmic fraction 30° C., 4) VEGFvNAR v19 periplasmic fraction 37° C., 5) VEGFvNAR v19 soluble cytoplasmic fraction 30° C., 6) VEGFvNAR v19 soluble cytoplasmic fraction 37° C., 7) VEGFvNAR v19 insoluble cytoplasmic fraction (Inclusion bodies) 30° C., 8) VEGFvNAR v19 insoluble cytoplasmic fraction (Inclusion bodies) 37° C.

FIG. 14: Western-Blot Analysis. A: Acrylamide gel electrophoresis (15% SDS-PAGE) of the rhVEGF samples (500 ng) and BSA control (5000 ng). B: Electroblotted to nitrocellulose membrane and sequential hybridization with the corresponding vNAR (10 μg), anti-HIS (1:3000) plus anti-mouse secondary antibody conjugated to peroxidase (1:3000). Revealed by ECL.

FIG. 29: Model 1 of the complex VEGF (chains in green and cyan) with vNAR V19 (chain in magenta).

FIG. 30: Model 2 of the complex VEGF (chains in green and cyan) with vNAR V19 (chain in magenta).

FIG. 36: Model 1 of the complex VEGF (chains in green and cyan) with vNAR V32R (chain in magenta).

FIG. 37: Model 2 of the complex VEGF (chains in green and cyan) with vNAR V32R (chain in magenta).

FIG. 50: Design of experiment. The vNAR antibody concentrations tested in ELISA plate of 96 wells are shown (A-H rows, 1-12 columns needed for quadruplicates), as well as the positive and negative controls used throughout the experiment.

Untreated controls (A) show minimal formation of tubes in the course of 14 days of testing. Treatment with VEGF 4 ng/mL shows the increase in the formation of tubes (B) with respect to control. It is observed that the higher the concentration of V32R antibody, the tube formation decreases (C-H).

Figure 54:
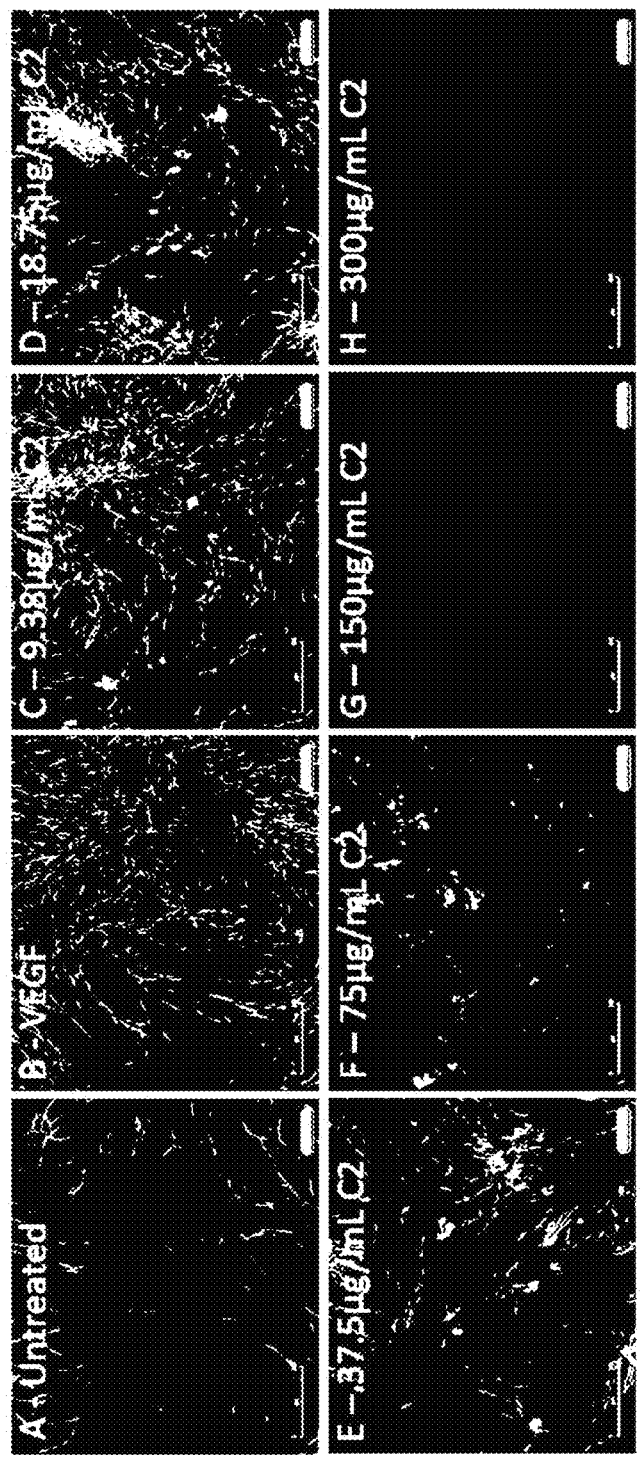

FIG. 54: Representative images of the effect of VEGF and the vNAR V19 antibody in the networking formation. Untreated controls (A) show minimal formation of tubes in the course of 14 days of testing. Treatment with VEGF 4 ng/mL shows the increase in the formation of tubes (B) with respect to control. It is observed that the higher the concentration of V19 antibody, the tube formation decreases (C-H).

Figure 55:
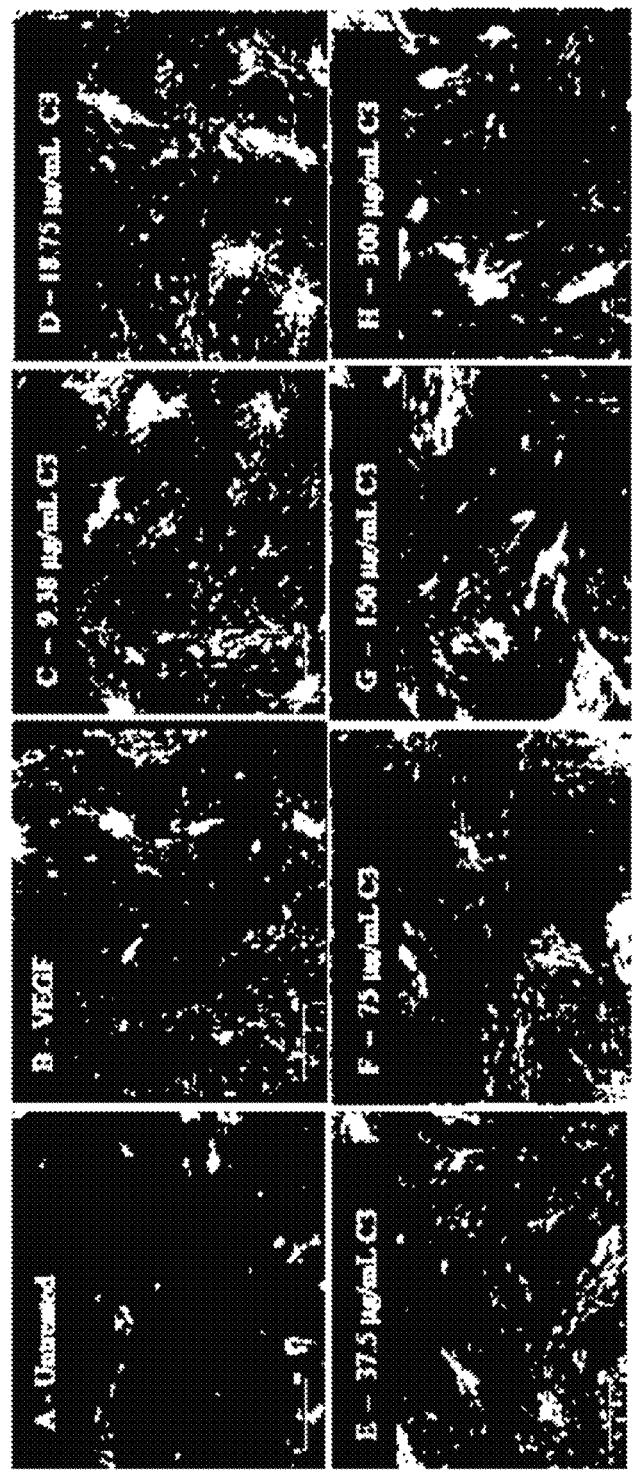

FIG. 55: Representative images of the effect of VEGF and the vNAR V13* antibody in the networking formation. Untreated controls (A) show minimal formation of tubes in the course of 14 days of testing. Treatment with VEGF 4 ng/mL shows the increase in the formation of tubes (B) with respect to control. It is observed that the higher the concentration of V13 antibody, the tube formation decreases (C-H). *Clone in the referred patent U.S. Pat. No. 8,496,933.

Figure 56:
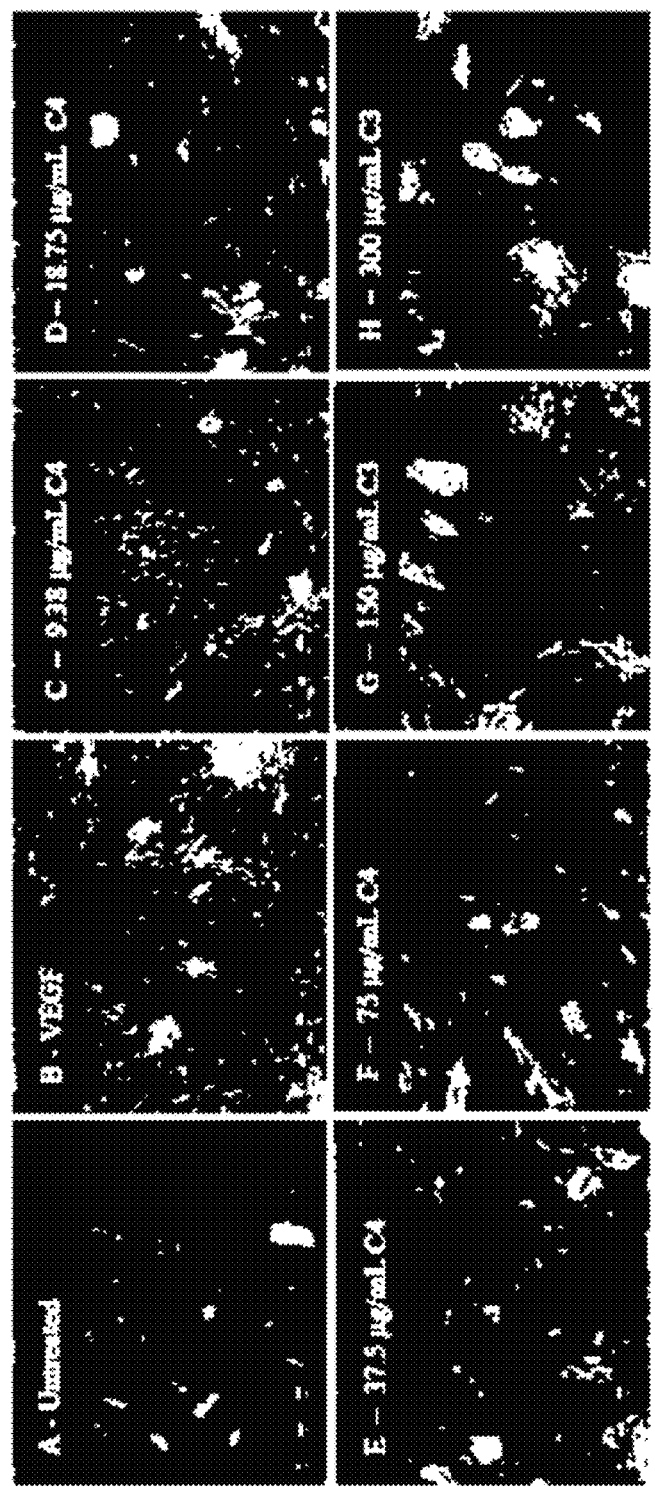

FIG. 56: Representative images of the effect of VEGF and the reference antibody* in the networking formation. Untreated controls (A) show minimal formation of tubes in the course of 14 days of testing. Treatment with VEGF 4 ng/mL shows the increase in the formation of tubes (B) with respect to control. It is observed that the higher the concentration of reference antibody, the tube formation decreases (C-H). *Ranibizumab (Genentech/Roche).

DETAILED DESCRIPTION OF THE INVENTION

The present invention refers to the generation of shark-based therapeutic monoclonal antibodies known as IgNAR (by the acronym of new antigen receptor) which are comprised of heavy chains of immunoglobulins. Specifically the present invention relates to the selection of the variable domains (vNAR) of these heavy chains. In this case, they are characterized by their ability to recognize the cytokine known as vascular endothelial growth factor (VEGF). The vNARs are of interest in the field of biotechnology due to their biological and biophysical properties. The vNAR products are highly resistant to environmental conditions and have a high capacity for topical therapeutic action. Together with the variable domains derived from camel immunoglobulin (known as $V_HH$); the vNARs are the smallest biological molecules capable of recognizing antigens. Due to these properties the vNARs outweigh the disadvantages and drawbacks of conventional therapy with monoclonal antibodies.

The present invention refers to the selection, isolation and purification of proteins belonging to variable regions named $V_HNAR$ or vNAR, originated from IgNAR-type immunoglobulins of elasmobranches with antigen receptor abilities. The clones from which they originate are named VEGFvNAR V32R and V19; and the respective antibodies are named V32R and V19 (also defined as either v19 or v32R).

The present invention also refers to the development of vNAR-based biopharmaceuticals that block the vascular endothelial growth factor (VEGF) since they have a high and very specific affinity for VEGF. These generated molecules have been subjected to different isolation and purification protocols. They are characterized by their intrinsic properties such as their sequence and three-dimensional structure, as well as their affinity and ability to recognize its target molecule which results in a more efficient neutralizing capacity than of other related molecules.

Vectors used for the selection of the clones are: pCOMb3X, with resistance to Ampicillin and Carbenicillin. The production strain is ER2537 and expression strains used were TOP10F' and BL21 (DE3), the latter being selected for expression, because its deficiency in protease contributes to improve yields.

In Example 1, the obtaining of the gene bank of specimens immunized by phage display from where the V19 and V32R clones originate, as well as the V13 clone described in the prior art, and which was used as comparative along the characterization of V19 and V32R, is described. ELISAs were performed with vNAR protein selected from the periplasmic space expressed in TOP10F'. From the results of the ELISA for expression and recognition of anti-VEGF vNAR, the clones were screened by affinity for VEGF and proceeded to obtain the sequences of each.

In order to demonstrate that the new clones are not a laboratory artifice and that they actually comprise differential antibodies that provide a surprising and unexpected technical advantage over the prior art, the characterization of the clone V13 has also been included herein—previously described in U.S. Pat. No. 8,496,933—and it has been subjected to the same isolation and purification protocols performed in the development of the invention in order to compare the results.

The DNA sequence that codifies for the protein of clone 13 specific for VEGF is the following one (identified as SEQ. ID NO: 1 in the list of sequences). The example 4 shows the method for obtaining the sequences:

```
GCAAGCCTGGACCAAACACCAAGAACGGCAACGAGAGAGACAGGCGAA

TCCCTGAGCATTAACTGCGTCCTCACTGATACTAGCCATATTTTGTTC

GGCACAAAATGGCTCTGGAATAATCCGGGTTCAACAGATTGGGAAAGC

ATAACGATTGGCGGACGATATGCTGAATCAGTCAACAACCAAGCAAAG

TCATTTTCTCTGCAAATCAAGGACCTGACAGTTGAAGACAGTGGCACC

TATTACTGCAAGCGCAAACCATAGGAAGACGCAAAAATCTACTTCCAC

GCCCATTGGTGAACGGTATAGCTGCGATGGGGTATAGCTCCAGTGACT

ACGACGGAGCTGGCACCGTGCTGACTGTGAAC
```

The resulting clone V13 was characterized by having high specificity for human VEGF, its aminoacidic sequence is the following (identified in the list of sequences as SEQ. ID NO: 2):

```
ASLDQTPRTA TRETGESLSI NCVLTDTSHI LFGTKWLWNN

PGSTDWESIT IGGRYAESVN NQAKSFSLQI KDLTVEDSGT

YYCKAQTIGR RKNLLPRPLV NGIAAMGYSS SDYDGAGTVL

TVN
```

FIG. 1 shows the protein sequence of anti-VEGF vNAR V13, described in U.S. Pat. No. 8,496,933 indicating the conserved domains.

The Clone V19 was selected from panning round 4 against the cytokine $VEGF_{165}$ of species *Orectolobus maculatus*.

The plasmid DNA sequence of the clone V19 (418 bp) is the following and corresponds to SEQ. ID. NO: 3:

```
CAACGGGTTGAACAAACACCAAGAACAGCAACAAAAGAGACGGGCGAA

TCACTGACCATCAACTGCGTCCTAAGAGATGCTAGTTTTGAATTAAAA

GACACGGGCTGGTATCGGACAAAATTGGGTTCAACAAATGAGCAGAGT

ATATCAATTGGCGGACGATATGTTGAAACAGTCAACAAGGGATCAAAG

TCCTTTTCTCTGAGAATTAGTGATCTGAGAGTTGAAGACAGTGGCACG

TATAAGTGTCAAGCATTCTATTCTCTTCCGTTGGGCGATTACAACTAT

TCTCTGCTGTTTAGGGGTGAGAAAGGAGCTGGCACCGTGCTGACTGTG

AAC
```

The amino acid sequence for vNAR19 (V19) corresponds to SEQ. ID. NO. 4:

```
AQRVEQTPRTATKETGESLTINCVLRDASFELKDTGWYRTKLGSTNEQ

SISIGGRYVETVNKGSKSFSLRISDLRVEDSGTYKCQAFYSLPLGDYN

YSLLFRGEKGAGTVLTVN
```

The plasmid DNA sequence of the clone V32R (421 bp), selected from an immunization scheme of the species Heterodontus francisci employing round 4, is the following and corresponds to SEQ. ID. NO. 5:

```
GCAAGCCTGGACCAAACACCAAGAACGGCAACGAGAGAGACGGGCGAA

TCCCTGACCATTAACTGCGTCTTCACTGATTCTAGCTGTGGTTTGTGC

GGCACATCTTGGTTCCGGAATAATCCGGGTTCAACAGATTGGGAACGC

ATAACGATTGGCGGACGATATGTTGAATCAGTCAACAAGGGAGCAAAG

TCATTTTCTCTGCAAATCAAGGACCTGACAGTTGAAGACAGTGTCACC

TATTACTGCAAAGCGCAAGGTCATCGATACTTCAGTAAGGTGTGCGAG

CTGCGATGTCCCAGTTACTACTACGACGGAGCTGGCACCGTGCTGACT

GTGAAC
```

The amino acid sequence of vNAR v32R corresponds to SEQ. ID. NO. 6:

```
AASLDQTPRTATRETGESLTINCVFTDSSCGLCGTSWFRNNPGSTDWE

RITIGGRYVESVNKGAKSFSLQIKDLTVEDSVTYYCKAQGHRYFSKVC

ELRCPSYYYDGAGTVLTVN
```

FIG. 2 shows the alignment between the sequences corresponding to the clones V13, V32R y V19, as reference, and indicating the differences thereof.

In order to improve the yields previously obtained, different tests and methods of expression and purification were carried out during the development of the invention in order to detect and achieve the best conditions for expression and purification of proteins, as well as the subsequent assessment on the performance of each of the obtained clones to bind and neutralize VEGF.

The synthesis of genes encoding antibody VEGFvNAR fused at its carboxy-terminus to the coding sequences of the 6His and HA tags was performed. The key feature of this synthesis was optimization of codons for expression in Escherichia coli. The synthetic genes were cloned in 2 bacterial plasmids. These were used to transform competent cells of E. coli DH5α strain. Table 1 shows the constructs tested for each of the sequences V13, V19 y V32R.

TABLE 1

Constructs for expression in E. coli

| | |
|---|---|
| VEGFvNAR 1 | SP-VEGFvNAR ORF-6His-HA |
| VEGFvNAR 2 | VEGFvNAR ORF-6His-HA |
| VEGFvNAR 3 | SP-VEGFvNAR-ORF |
| VEGFvNAR 4 | VEGFvNAR-ORF |

Figure 3A:
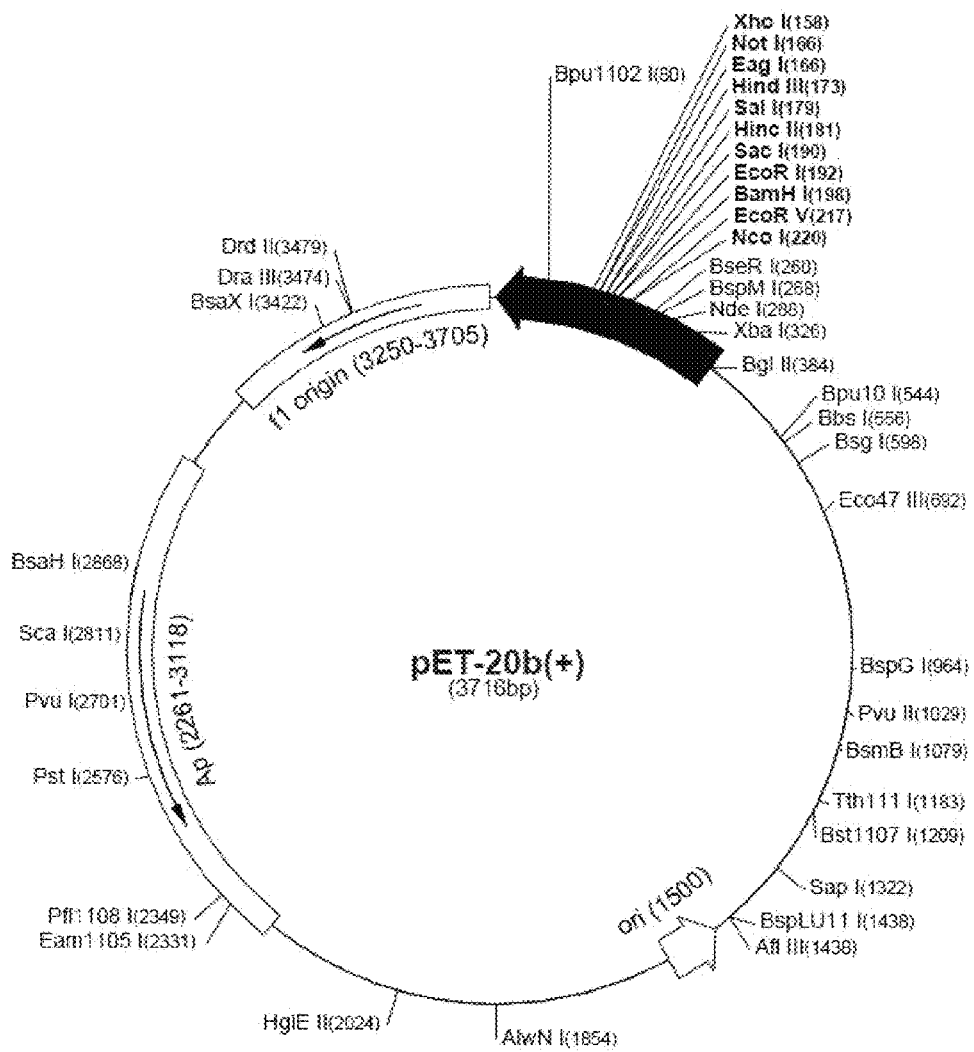
FIG. 3: Expression plasmids used to generate the constructs: A: pET20b+(vNAR 1 and 3), B: pET28a+(vNAR 2 ad 4).
Figure 3B:
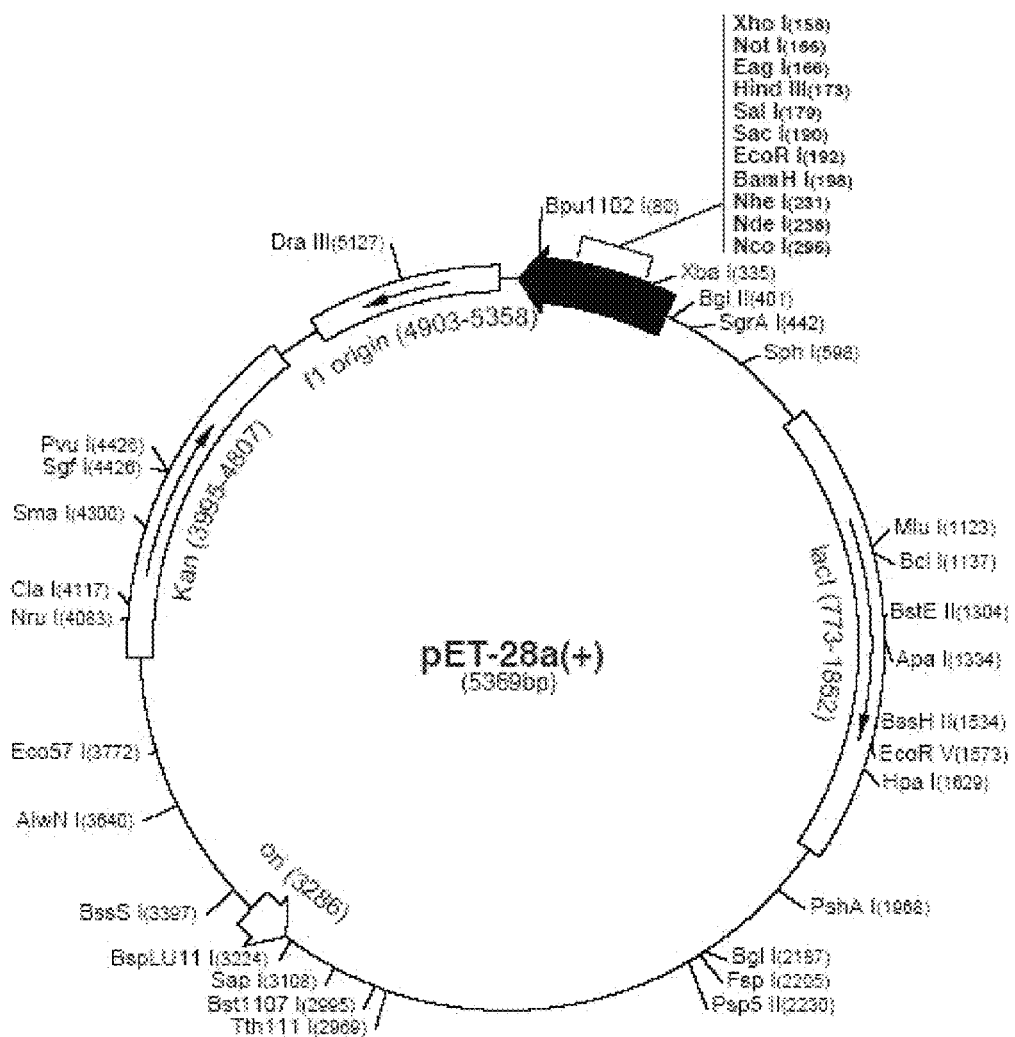

The expression plasmids used to generate these constructs, FIGS. 3A and 3B, are pET20b+(vNAR 1 and 3) and pET28a+(vNAR 2 and 4). Subcloning of the sequence of interest is performed into a vector that includes the signal peptide pelB.

Cloning of VEGFvNAR is executed in a bacterial expression vector (pET20b+). Amplification plus the isolation of the Open Reading Frame (ORF) of the recombinant antibody was performed from the synthetic gene by PCR with specific oligonucleotides. By using restriction enzymes, the amplified fragment was subcloned into a specifically selected bacterial expression vector and containing the pelB signal that will direct the protein to the periplasm, once it is expressed. The clones were obtained after transformation of the ligation mixture (plasmid+insert) in competent cells of E. coli DH5α strain. For the subcloning of the sequence of interest into a vector that does not include the signal peptide pelB: Cloning of VEGFvNAR in a bacterial expression vector (pET28a+) was performed in parallel and a second subcloning of the antibody was performed from the same synthesized cDNA template that has been used for the previous cloning, but this time excluding the signal peptide, in order to direct the entire protein to the cell cytoplasm.

Both in pET20b+ and pET28a+, transformants obtained were individualized by selection in solid culture (LB Agar/Ampicillin), and 2 transformants by genetic construction for preservation and analysis of plasmid DNA by sequencing, as a confirmatory method, are selected.

With the purified recombinant DNAs of the last point, we proceeded to the transformation in a suitable E. coli line for protein expression, a strain that is deficient in proteases, BL21 (DE3) strain, as mentioned above. The clones obtained were individualized and again their nature was confirmed by colony-PCR and agarose gel electrophoresis.

By using the positive clones, the expression of protein was evaluated at small scale starting from 50 ml of bacterial culture at two temperatures (30° C. and 37° C.) and two times of incubation: 16 and 20 hours. These variables of temperature and time are studied in order to obtain the best conditions for the production of proteins. This pilot study is based on the use of bacterial cultures in liquid medium from the producing clones in E. coli BL21 (DE3) and the expression inducer IPTG.

Figure 4:
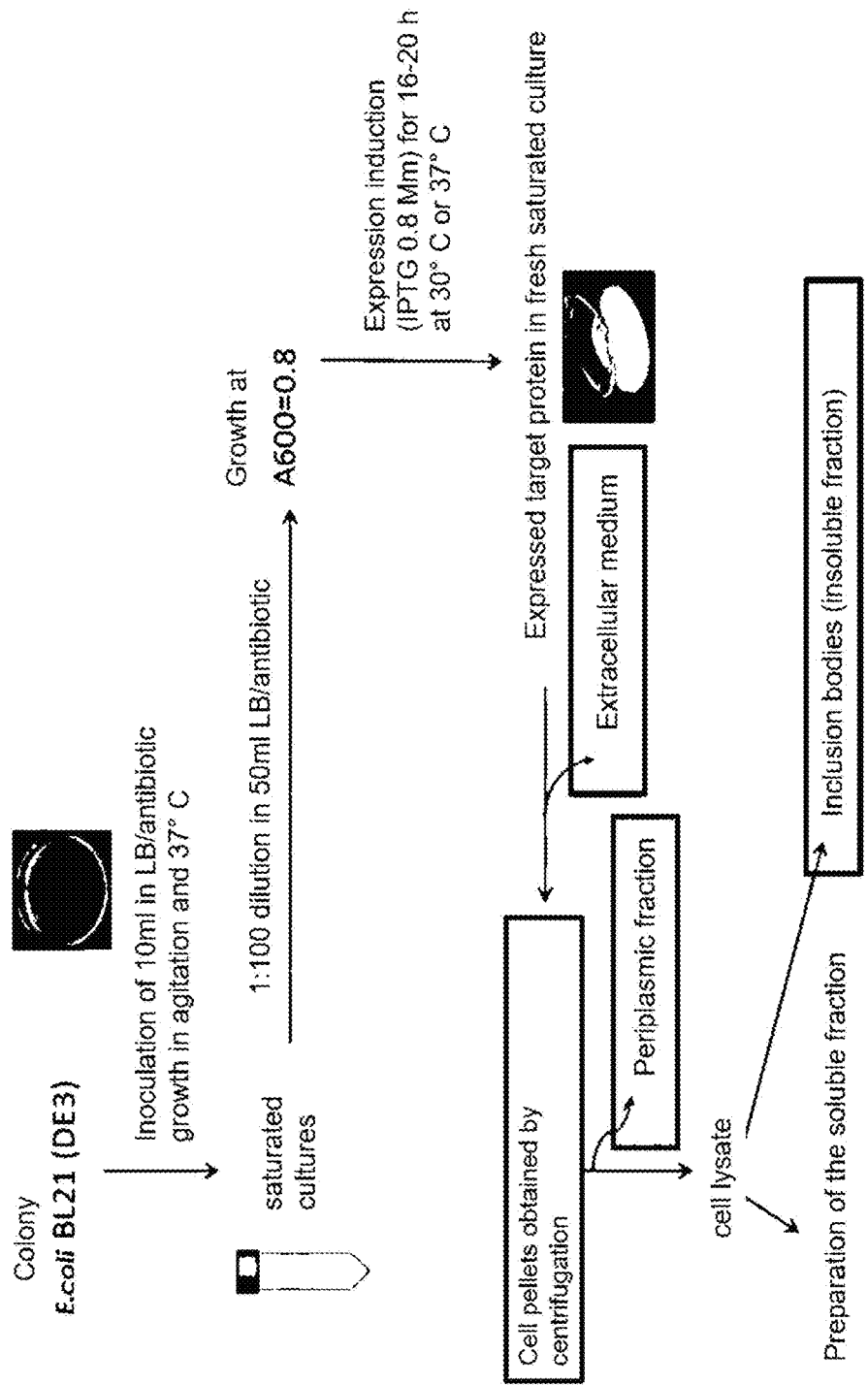
FIG. 4: Processing of the culture of E. coli BL21 (DE3) until the obtaining of periplasmic fractions and the soluble and insoluble cytoplasmic fractions.
Figures 5A, 5B:
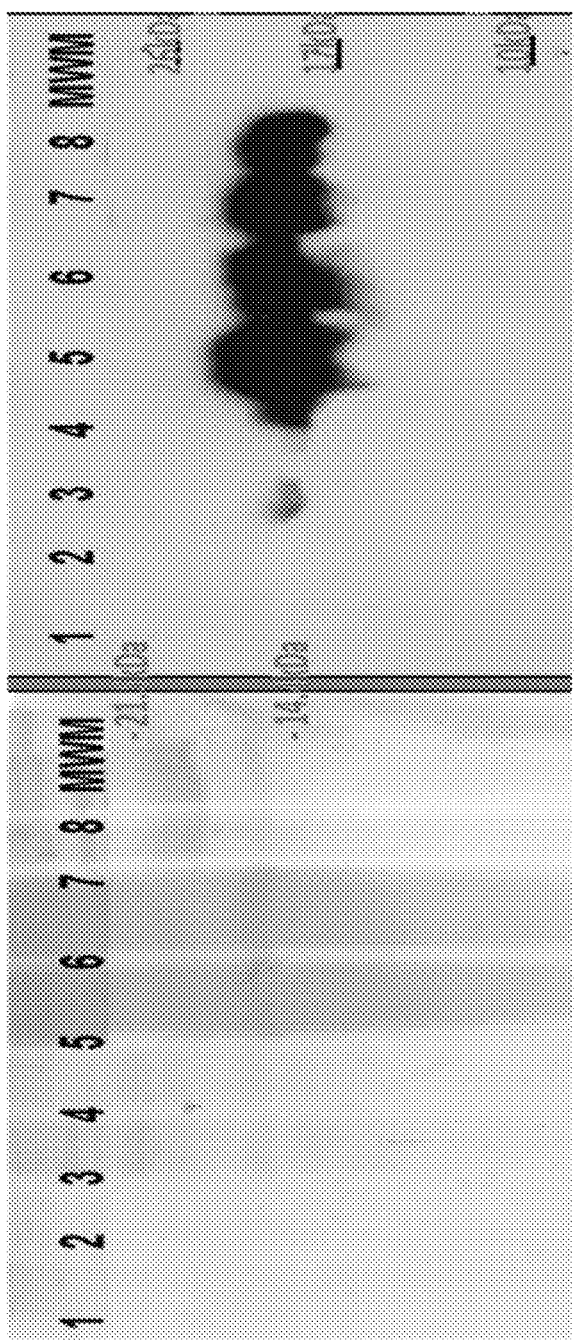
FIG. 5: Analysis of subcellular fractions detection of VEGFvNAR v32R with signal peptide (sp): A: SDS PAGE 15% acrylamide reducing conditions, staining with Coomasie blue. B: Electroblotted to nitrocellulose membrane, hybridization with anti-His (1:3000) plus anti-mouse secondary antibody conjugated to peroxidase (1:3000). Revealed by ECL (by the acronym of enhanced chemiluminescence). Samples per lane: 1) spVEGFvNAR v32R extracellular fraction 30° C., 2) spVEGFvNAR v32R extracellular fraction 30° C., 3) spVEGFvNAR v32R periplasmic fraction 30° C., 4) spVEGFvNAR v32R periplasmic fraction 37° C., 5) spVEGFvNAR v32R soluble cytoplasmic fraction 30° C., 6) spVEGFvNAR v32R soluble cytoplasmic fraction 37° C., 7) spVEGFvNAR v32R insoluble cytoplasmic fraction (Inclusion bodies) 30° C., 8) spVEGFvNAR v32R insoluble cytoplasmic fraction (Inclusion bodies) 37° C.
Figure 6B:
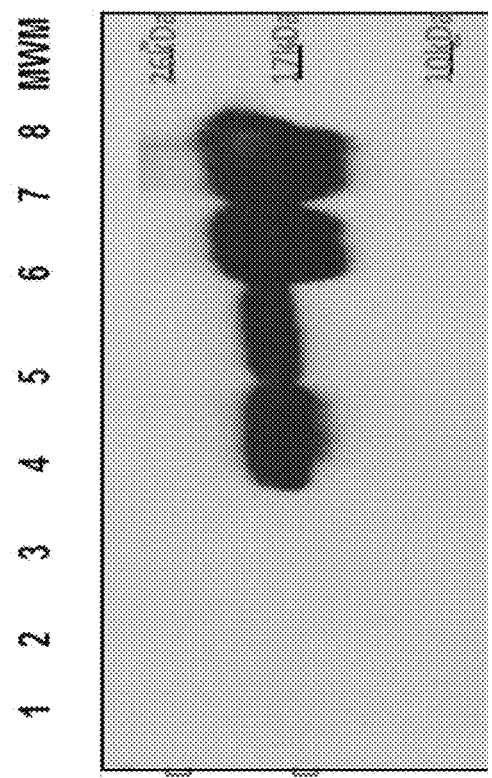
FIG. 6: Analysis of subcellular fractions detection of VEGFvNAR v32R without signal peptide: A: SDS PAGE 15% acrylamide reducing conditions, staining with Coomasie blue. B: Electroblotted to nitrocellulose membrane, hybridization with anti-His (1:3000) plus anti-mouse secondary antibody conjugated to peroxidase (1:3000). Revealed by ECL. Samples per lane: 1) VEGFvNAR v32R extracellular fraction 30° C., 2) VEGFvNAR v32R extracellular fraction 30° C., 3) VEGFvNAR v32R periplasmic fraction 30° C., 4) VEGFvNAR v32R periplasmic fraction 37° C., 5) VEGFvNAR v32R soluble cytoplasmic fraction 30° C., 6) VEGFvNAR v32R soluble cytoplasmic fraction 37° C., 7) VEGFvNAR v32R insoluble cytoplasmic fraction (Inclusion bodies) 30° C., 8) VEGFvNAR v32R insoluble cytoplasmic fraction (Inclusion bodies) 37° C.
Figure 6A:
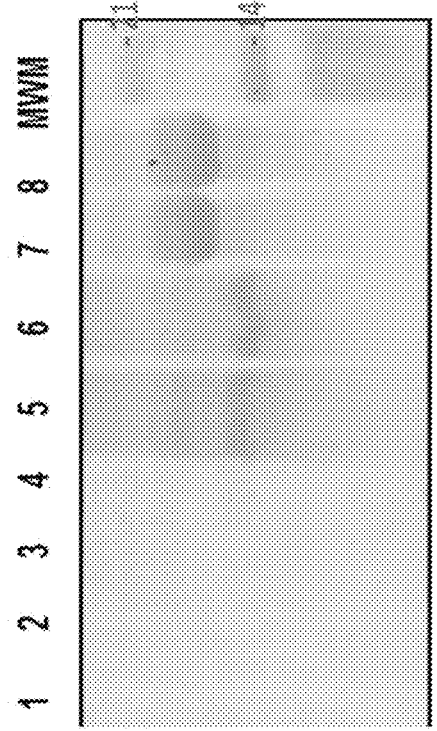
Figure 7A:
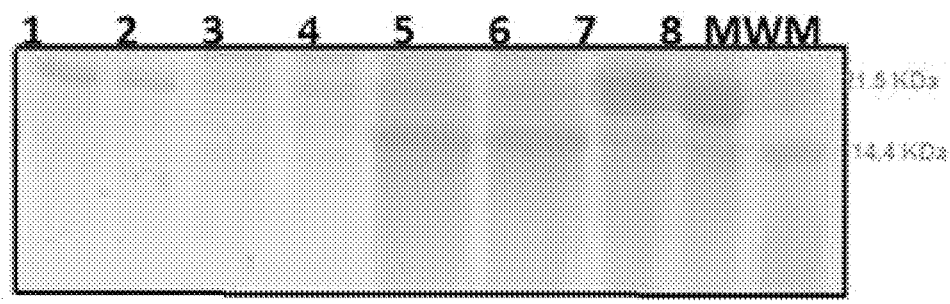
FIG. 7: Analysis of subcellular fractions detection of VEGFvNAR v19 with signal peptide (sp): A: SDS PAGE 15% acrylamide reducing conditions, staining with Coomasie blue. B: Electroblotted to nitrocellulose membrane, hybridization with anti-His (1:3000) plus anti-mouse secondary antibody conjugated to peroxidase (1:3000). Revealed by ECL. Samples per lane: 1) spVEGFvNAR v19 extracellular fraction 30° C., 2) spVEGFvNAR v19 extracellular fraction 30° C., 3) spVEGFvNAR v19 periplasmic fraction 30° C., 4) spVEGFvNAR v19 periplasmic fraction 37° C., 5) spVEGFvNAR v19 soluble cytoplasmic fraction 30° C., 6) spVEGFvNAR v19 soluble cytoplasmic fraction 37° C., 7) spVEGFvNAR v19 insoluble cytoplasmic fraction (Inclusion bodies) 30° C., 8) spVEGFvNAR v19 insoluble cytoplasmic fraction (Inclusion bodies) 37° C.
Figure 7B:
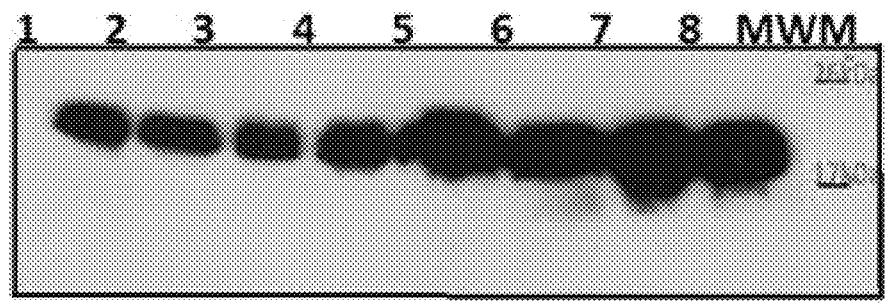
Figure 9A:
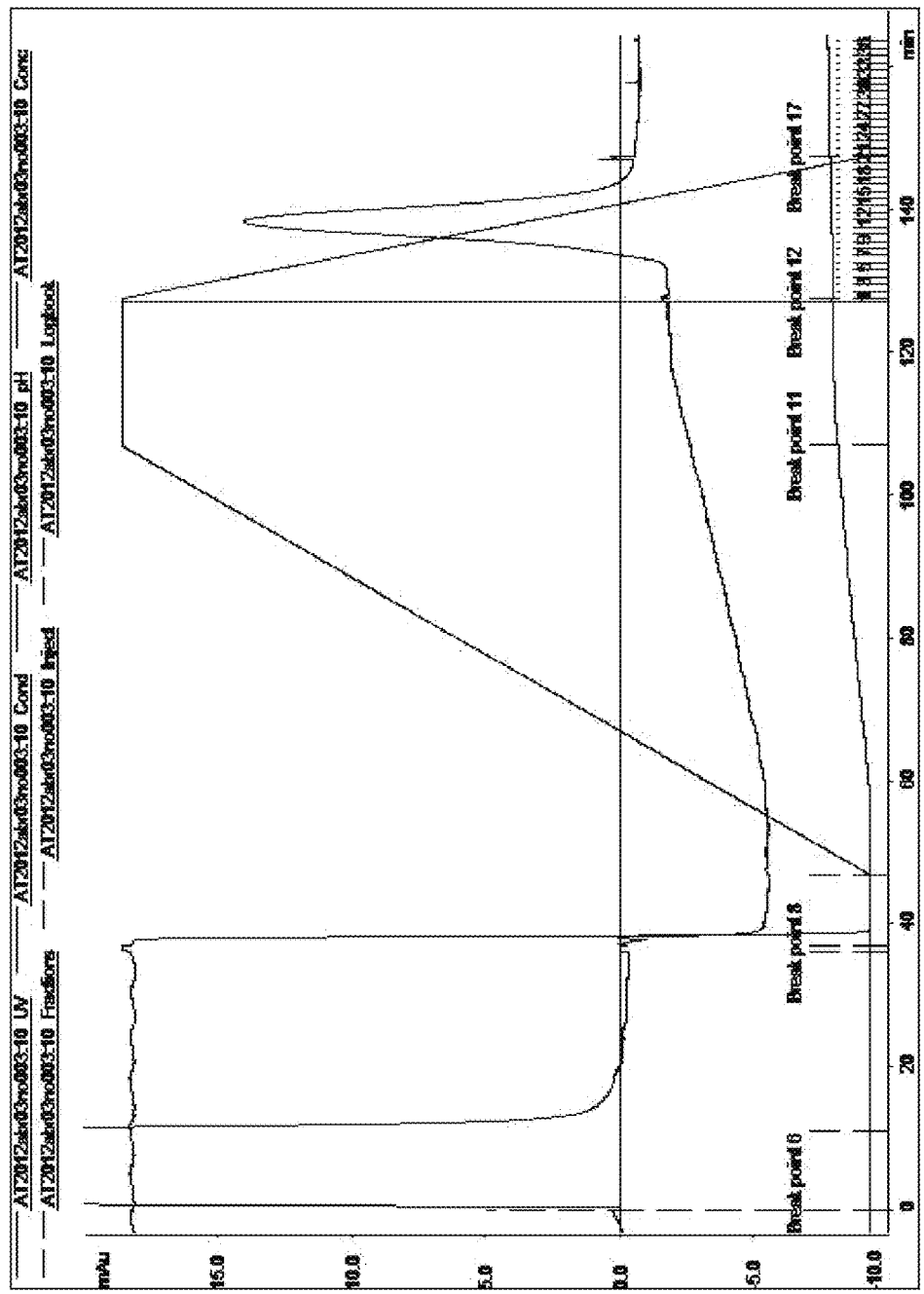
FIG. 9: Insoluble cytoplasmic fraction corresponding to VEGFvNAR v32R with signal peptide. A: Solubilization of the added protein and FPLC chromatography (on-column refolding) in HisTrap FF crude 1 ml affinity columns. B: Analysis by acrylamide gel electrophoresis (15% SDS-PAGE).
Figure 9B:
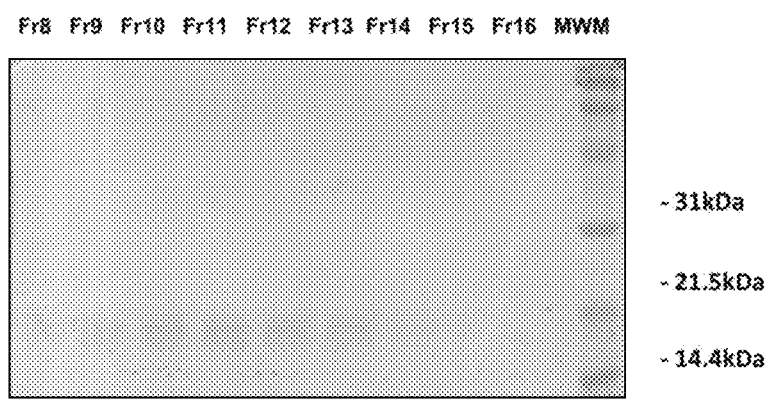
Figure 10A:
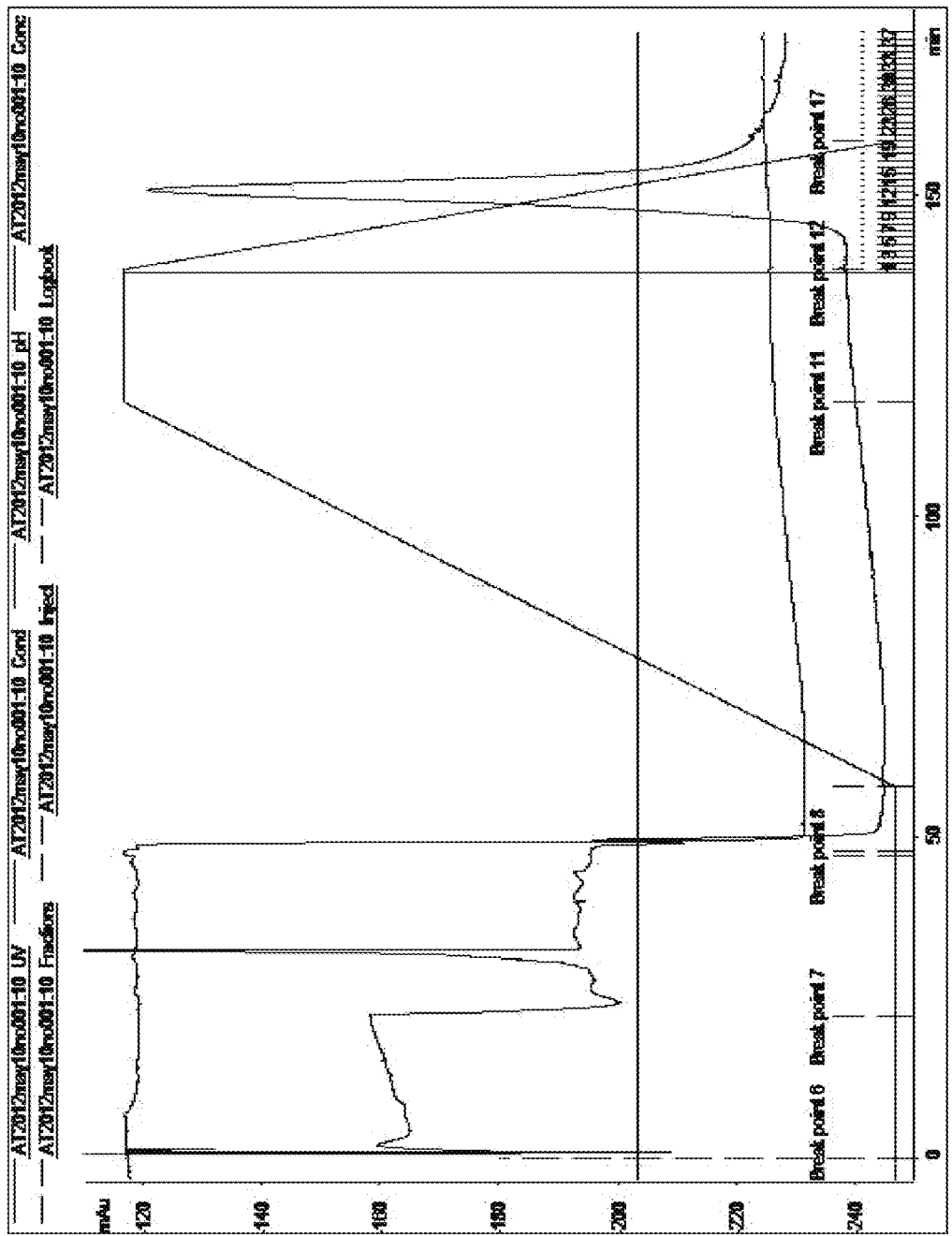
FIG. 10: Insoluble cytoplasmic fraction corresponding to VEGFvNAR v32R without signal peptide. A: Solubilization of the added protein and FPLC chromatography (on-column refolding) in HisTrap FF crude 1 ml affinity columns. B: Analysis by acrylamide gel electrophoresis (15% SDS-PAGE).
Figure 10B:
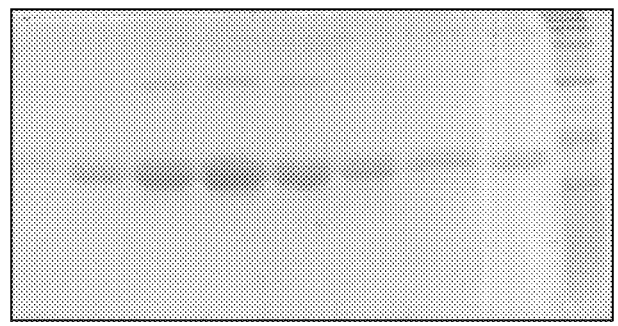
Figure 11A:
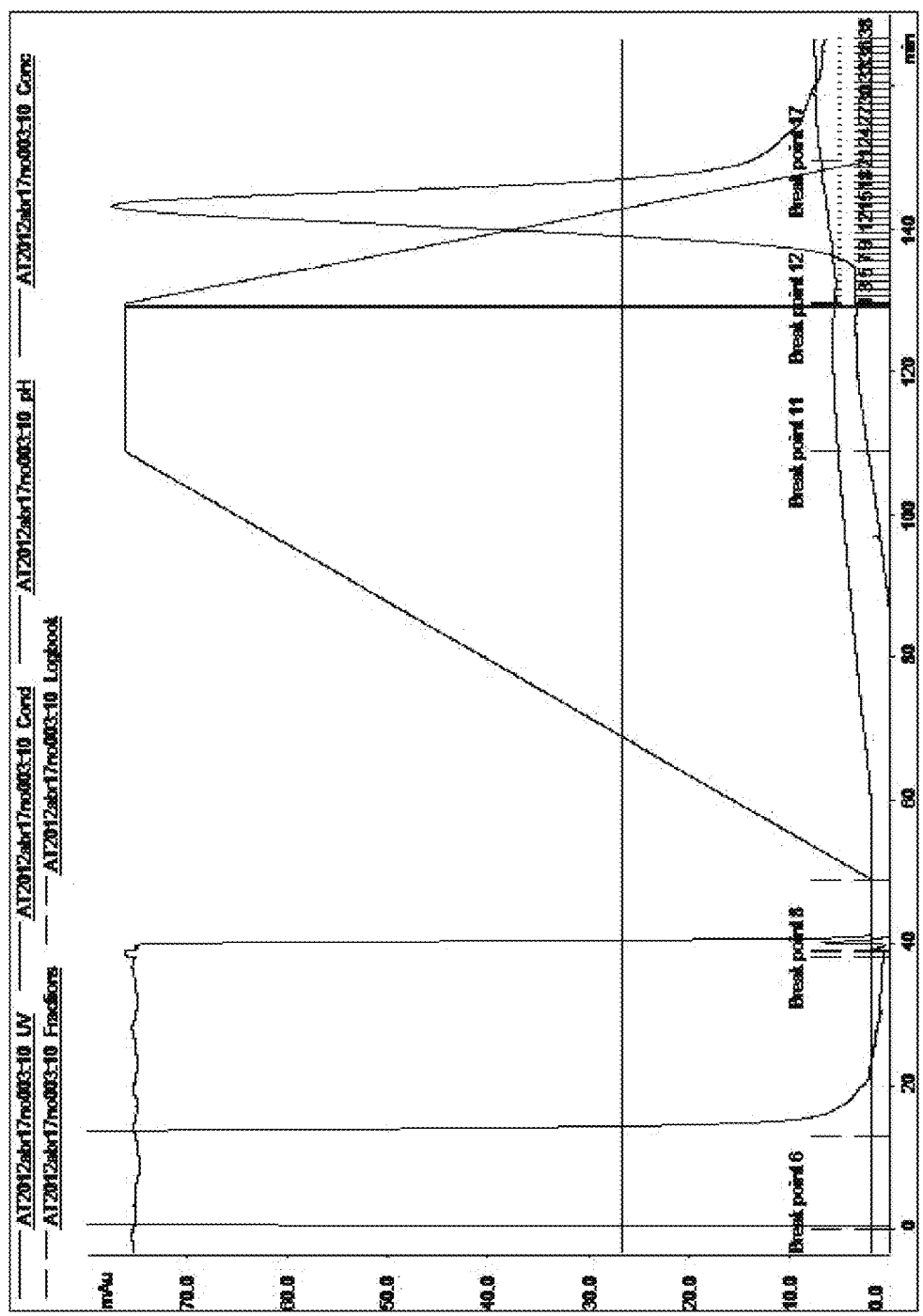
FIG. 11: Insoluble cytoplasmic fraction corresponding to VEGFvNAR v19 with signal peptide. A: Solubilization of the added protein and FPLC chromatography (on-column refolding) in HisTrap FF crude 1 ml affinity columns. B: Analysis by acrylamide gel electrophoresis (15% SDS-PAGE).
Figure 11B:
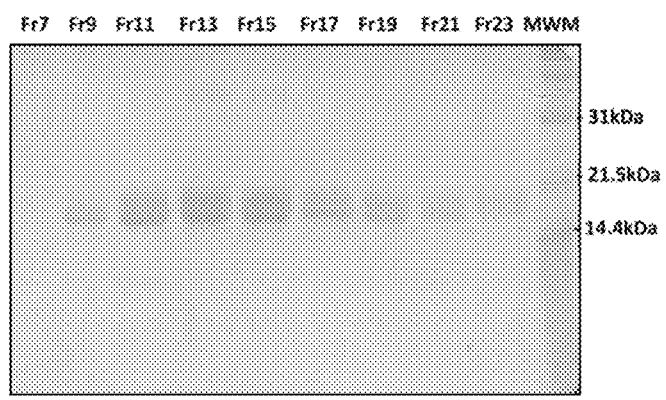
Figure 12A:
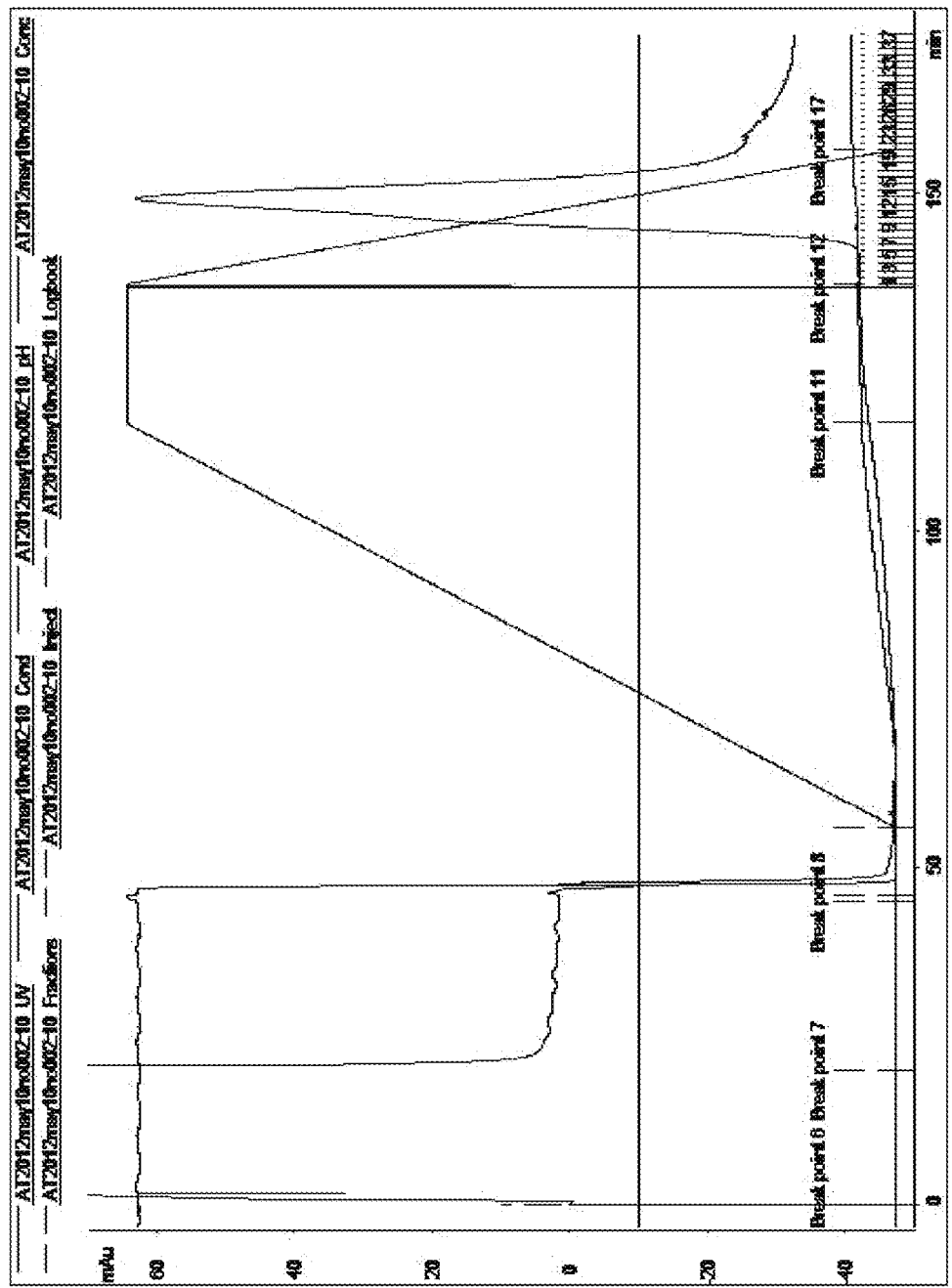
FIG. 12: Insoluble cytoplasmic fraction corresponding to VEGFvNAR v19 without signal peptide. A: Solubilization of the added protein and FPLC chromatography (on-column refolding) in HisTrap FF crude 1 ml affinity columns. B: Analysis by acrylamide gel electrophoresis (15% SDS-PAGE).
Figure 12B:
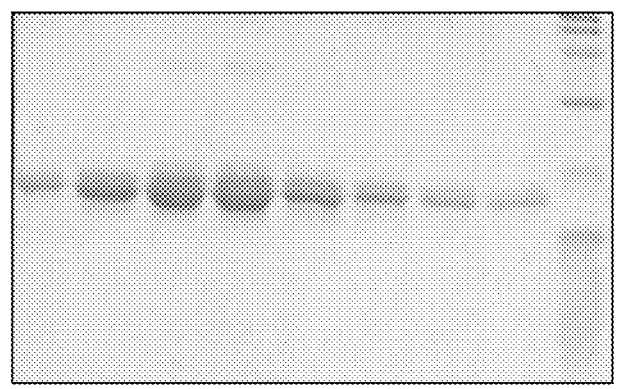

The culture was processed by centrifugation, thus separating the cells from the culture medium. The cells were treated to obtain the periplasmic fraction, on one hand, by a sucrose-mediated osmotic shock; and on the other, they were lysed with lysozyme, detergent and sonication to extract from them soluble and insoluble intracellular components separated by centrifugation. The process scheme is in FIG. 4, whereas the methodology is described in example 3.

At this stage, the expression levels of the recombinant protein of interest were analyzed in each of the different cellular fractions (secreted protein into the culture medium, periplasm, cytoplasmic and inclusion bodies) in order to assess the amount of protein in each cellular fraction and then determine its functionality, namely, the recognition or specific binding by the protein obtained from each fraction to the hVEGF protein.

Constructs for all clones, with and without signal peptide, were performed, maintaining the histidine tails and HA. Expression levels were evaluated in each one of them.

Different locations of the vNARs proteins, either secreted or intracellularly (either in soluble or insoluble fractions), were analyzed. The results presented in table 2 correspond to expression levels of the vNAR. In such results it appears that the vNAR proteins are expressed forming inclusion bodies which imply that they occur in the insoluble cytoplasmic fraction.

One of the best candidates initially considered was the extracellular VEGFvNAR1. This was identified by electrophoresis, but after performing an affinity test by ELISA, we found that this protein fraction had almost no affinity for the target molecule, while the most active fraction was the insoluble cytoplasmic.

Example 2 describes the obtaining of BL21 (DE3) producer clones and further processing until the performance of the Western blot and ELISA assays to measure recognition of each expressed vNAR, previously purified.

Example 3 describes the protocols to obtain subcellular fractions: periplasmic, extracellular, soluble cytoplasmic and insoluble cytoplasmic corresponding to the inclusion bodies. In each of these fractions protein concentrations were determined, as well as from the Western-blot analysis. Results are shown in FIGS. 5 to 8.

From the results obtained, we concluded that the presence of the signal peptide does not improve the expression in any of the fractions; further, its absence improved the concentrations obtained from the different vNARs present in the insoluble cytoplasmic fraction as inclusion bodies.

Since active vNARs proteins, obtained by the aforementioned recombinant methods, were found forming inclusion bodies, the research conducted during the development of the invention was directed to dissolve them by applying specific alternative methods in order to disaggregate the proteins and obtain them in a pure state, and soluble, without compromising their binding ability to the target molecule regardless the procedure.

In order to improve the yields previously obtained, different tests and methods of expression and purification were carried out during the development of the invention in order to detect and get the best conditions for expression and purification of proteins, as well as the subsequent assessment on the performance of each of the obtained clones to bind and neutralize VEGF.

The alternative method included in the present application is known as On-column refolding (or refolding in situ) consisting of the following steps: 1) cell lysis by sonication, 2) isolation of inclusion bodies 3) solubilization with guanidine chloride, protein purification by chromatography on His-Trap columns and column refolding using denaturing buffers of urea; and 4) eluting the solubilized and refolded protein. With both methods the vNARs would undergo denaturation and a refolding process to re-acquire their tertiary conformation, as described below in detail.

To carry out the processing by On-column refolding technique, it must be started from a plasmid containing the sequence of interest optimized for expression in *E. coli*. A design consisting in an open reading frame (ORF) was used, which encodes a fusion protein formed by vNAR antibodies and six HIS and HA tags. These tags fused to the molecule of interest are necessary because it allows both monitoring the production of the biological system of expression and its subsequent purification; in this case using standardized procedures, the presence of these tags does not interfere in any way with the performance of the molecules and they are later removed in the production stage.

The method of On-Column Refolding is a process of purification by affinity chromatography on immobilized metals; specific affinity resins for fused proteins with 6×His are used, in this case the protein of interest is in an insoluble fraction. Before the On-Column Refolding process takes place, the protein undergoes solubilization with guanidine chloride. During the On-column Refolding process, the sample of denatured protein is injected into the column where it is retained by affinity while binding buffer (A1) is maintained, see example 5. After switching to solubilization buffer (A2), the refolding gradient begins up to 100%. At this point the process of protein refolding has concluded. Subsequently this buffer is progressively replaced by elution buffer (A3) that causes the release of the proteins bound until then to the affinity column. Finally the eluted fractions containing protein were analyzed on acrylamide gel electrophoresis—SDS to study its size and composition.

The 1 ml fractions, with an absorbance at 280 nm, are the solubilized forms and fixed by affinity column and are refolded in situ and then eluted by adding imidazole at different fractions.

TABLE 2

Expression Levels vNAR V13

| Construct | Temperature | EXTRACELLULAR | PERIPLASMIC | SOLUBLE CYTOPLASMIC | INSOLUBLE CYTOPLASMIC |
|---|---|---|---|---|---|
| | | EXPRESSION LEVELS OF PROTEINS (mg of protein per liter of culture) | | | |
| VEGFvNAR 1 | 30° C. | ++ (1.7 mg/L) | +++ | <5% (0 mg/L) | 75% (0.4 mg/L) | 20% (0.44 mg/L) |
| VEGFvNAR 2 | 37° C. | + | +++ | 5% | 50% | 40% |
| VEGFvNAR 3 | 30° C. | − | ++++ | 0% | 10% (0.3 mg/L) | 90% (0.27 mg/L) |
| VEGFvNAR 4 | 37° C. | − | +++ | 0% | 0% | 100% |

The first purification method used for the V13 molecule, was the method known as On-bench refolding which basically consists of the following steps: 1) cell lysis by sonication, 2) isolation of the inclusion bodies, 3) solubilization with buffers of urea, 4) purification by affinity columns or immobilized metal ion (TALON™), 5) refolding with buffers including the glutathione redox system (GSH, G-S-S-G), and 6) elution of the solubilized protein and refolded through its pass by affinity chromatography (His Trap) using non-denaturing buffers.

Figure 13:
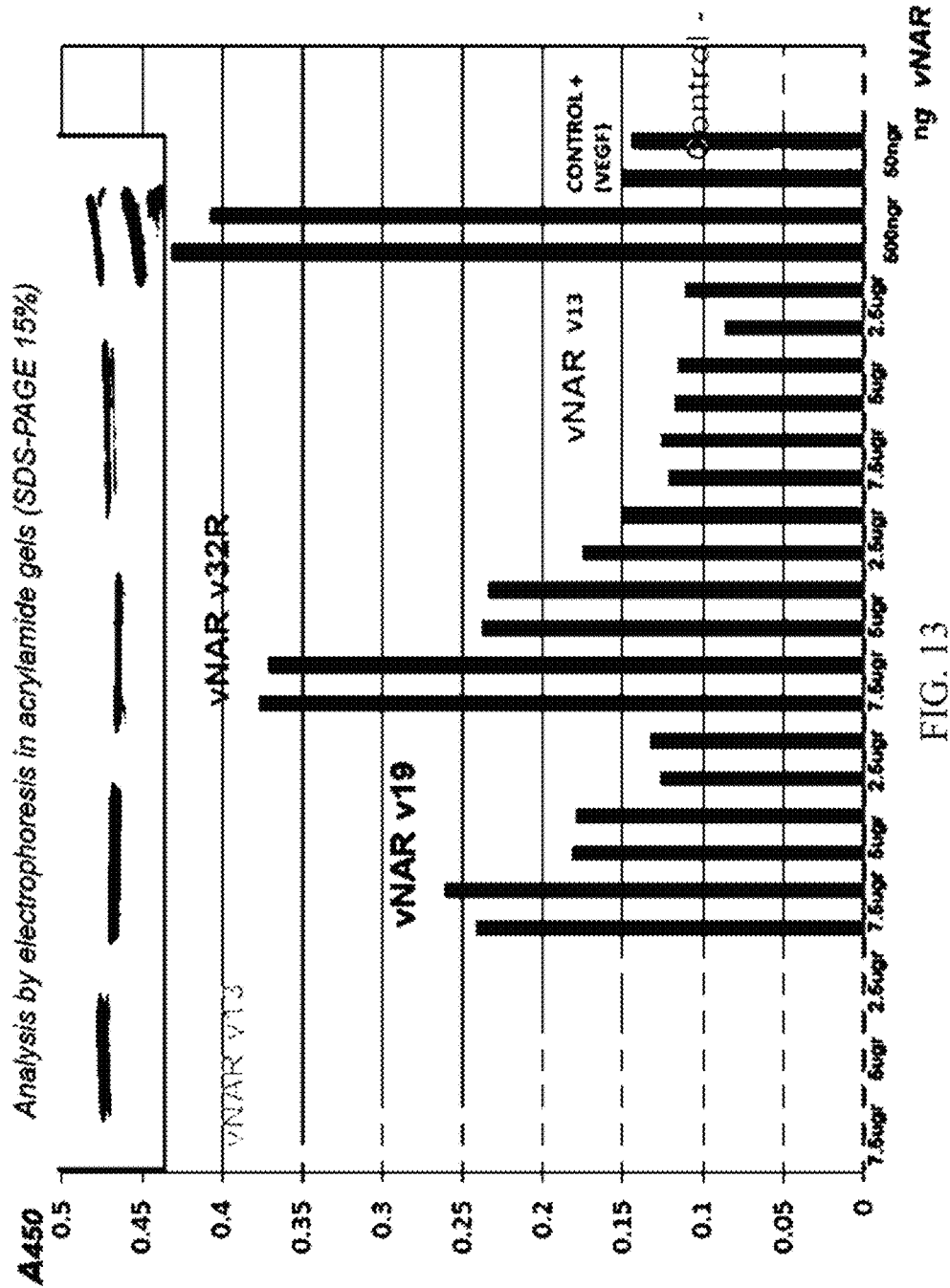
FIG. 13: Indirect ELISA upholstered with 200-300 ng/well of rhVEGF. Primary antibody vNAR V13, V19 or V32R, preps B, purify by On-column refolding. Control: primary antibody vNAR purify by On-column refolding (1 mg/ml). Secondary antibody: rabbit anti-HA 1:1000, tertiary antibody: goat anti-rabbit-HRPO 1:1000. Control+anti-VEGF Abcam, 500 or 50 ng/well. Revealed with TMB (3,3',5,5'-tetramethylbenzidine), Absorbance measured at 450 nm.

The eluted proteins subjected to this chromatography system are analyzed by acrylamide gel electrophoresis (15 μL of each fraction) and by Western-blot to verify their nature. Samples thus recovered were found in 20 mM Tris HCl, 0.5M NaCl, 1 mM β-mercaptoethanol, 0.3 M imidazole, 100 mM L-arginine buffer. The results of this processing are described in FIGS. 9 to 12. Afterwards, the functional validation of anti-VEGF vNAR was carried out by analyzing their binding properties to its target molecule that is the human VEGF A isoform 165. The analyses performed for this functional validation were ELISA, Dot-blot, Western-blot and flow cytometry, immunofluorescence and immunohistochemistry. As can be seen, the protein reflecting the higher affinity would be V32R, and all are superior in affinity to molecule V13 described in the granted U.S. Pat. No. 8,496,933. The improvement achieved by the "new" method applied is observed when comparing the same molecule V13 with 2 different processings. The results of the ELISA assays are shown in FIG. 13. The results of the Western-Blot analysis are shown in FIG. 14.

FIG. 14 shows in a comparative manner the amounts of the protein recognizing VEGF, of the vNAR V19 and V32 of this invention in view of the obtained V13. Both new proteins, V19 and V32R, possess an affinity and recognition capacity significantly higher than V13.

The anti-VEGF vNAR molecules have been optimized and their affinity properties have been significantly increased, so that their neutralizing capacities have been also increased, and the amount of vNAR needed to neutralize VEGF is lower. See example 10.

Briefly, we found in the test of affinity that the new target molecules obtained are higher in affinity and activity to that obtained in the U.S. Pat. No. 8,496,933.

Figure 15A:
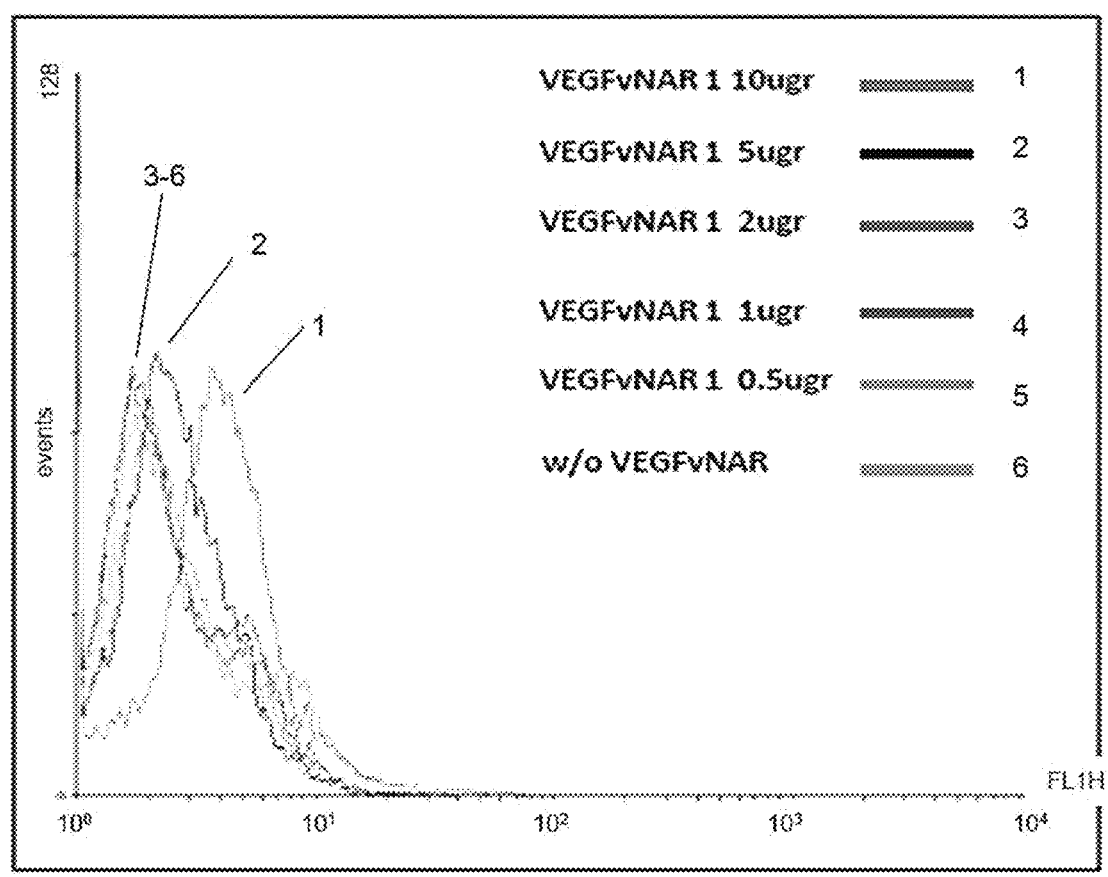
FIG. 15: Flow cytometry for U937 cells ($10^6$); cells are permeabilized in their membrane and treated with VEGFvNAR1, namely SP-VEGFvNARORF-6His-HA being in this case V13 (soluble extracellular)+Anti-HIS antibody (1:200)+goat anti-rabbit-alexa fluor 488 antibody (1:200). a) VEGFvNAR1 extracellular. b) Control anti-VEGF (Abcam).
Figure 15B:
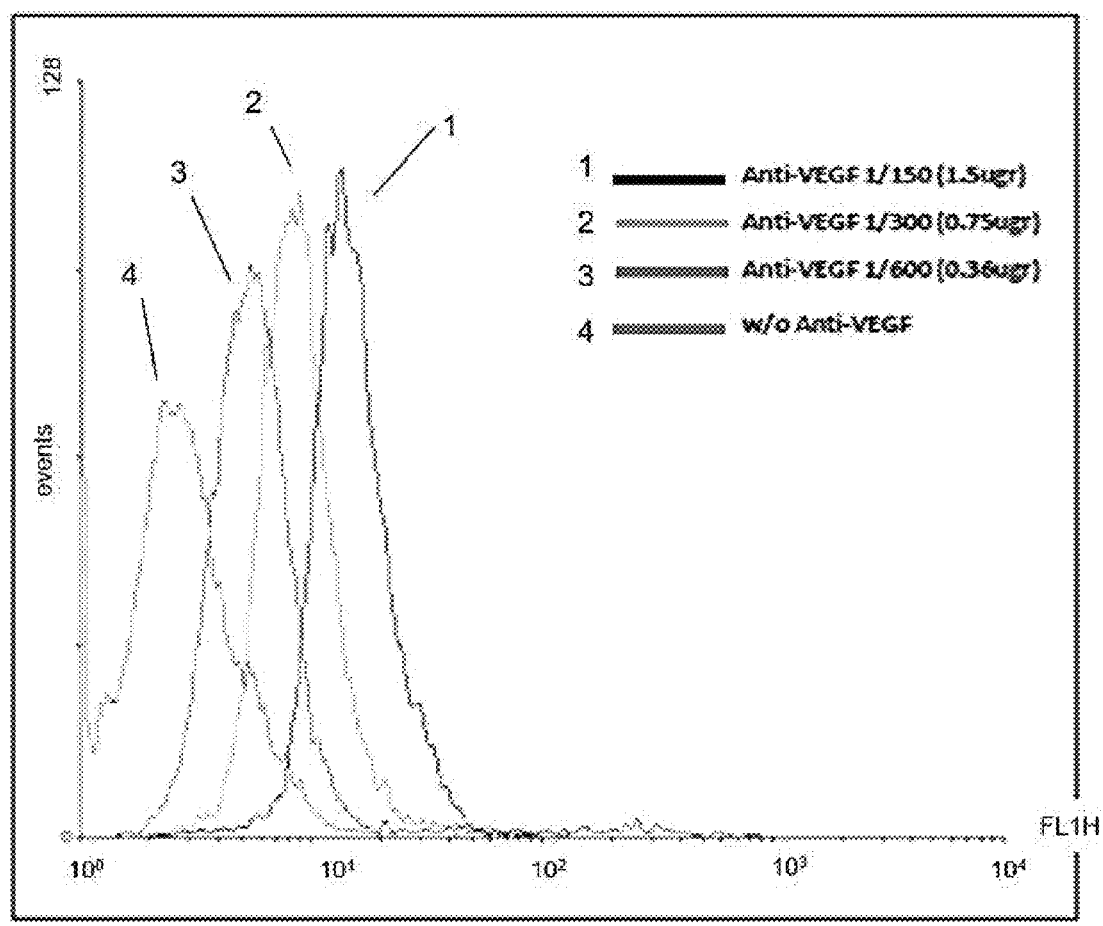
Figure 16A:
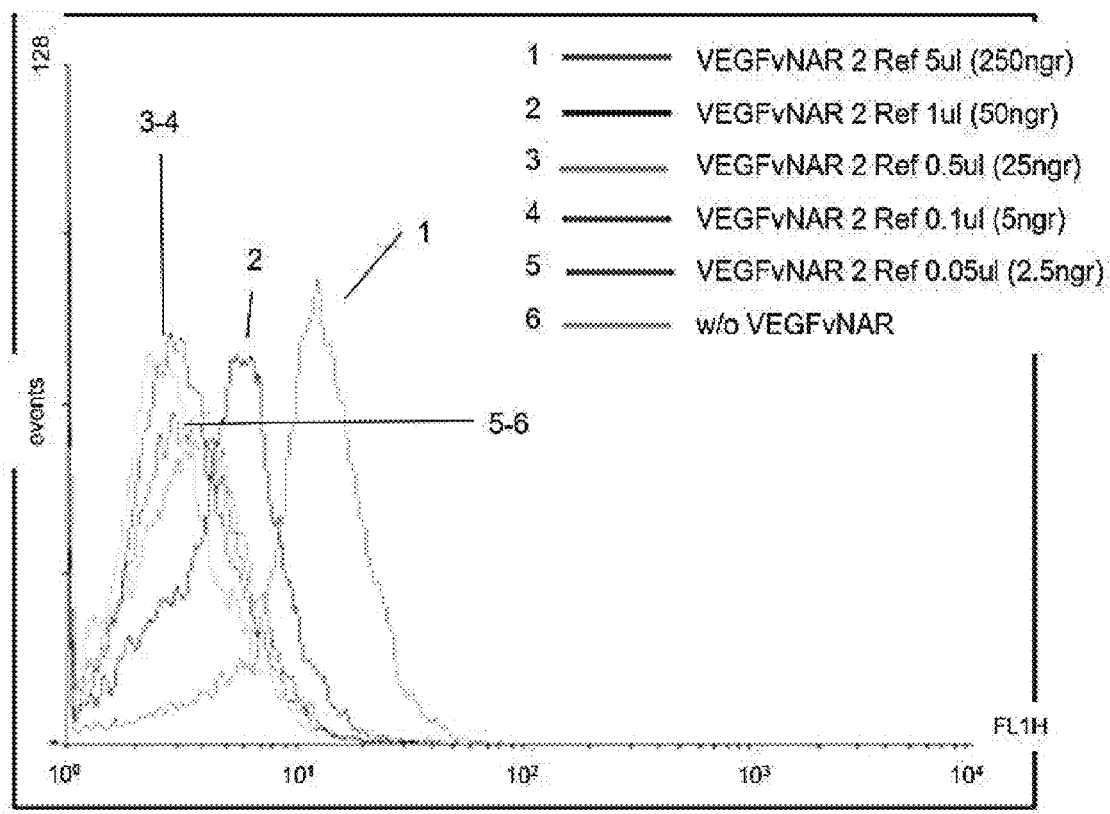
FIG. 16: Flow cytometry for U937 cells ($10^6$); cells are permeabilized in their membrane and treated with VEGFvNAR2, namely SP-VEGFvNARORF-6His-HA being in this case V13 (refolded insoluble cytoplasmic fraction)+Anti-HIS antibody (1:200)+goat anti-rabbit-alexa fluor 488 antibody (1:200). A) VEGFvNAR2 (Refolded). B) Control anti-VEGF (Abcam).
Figure 16B:
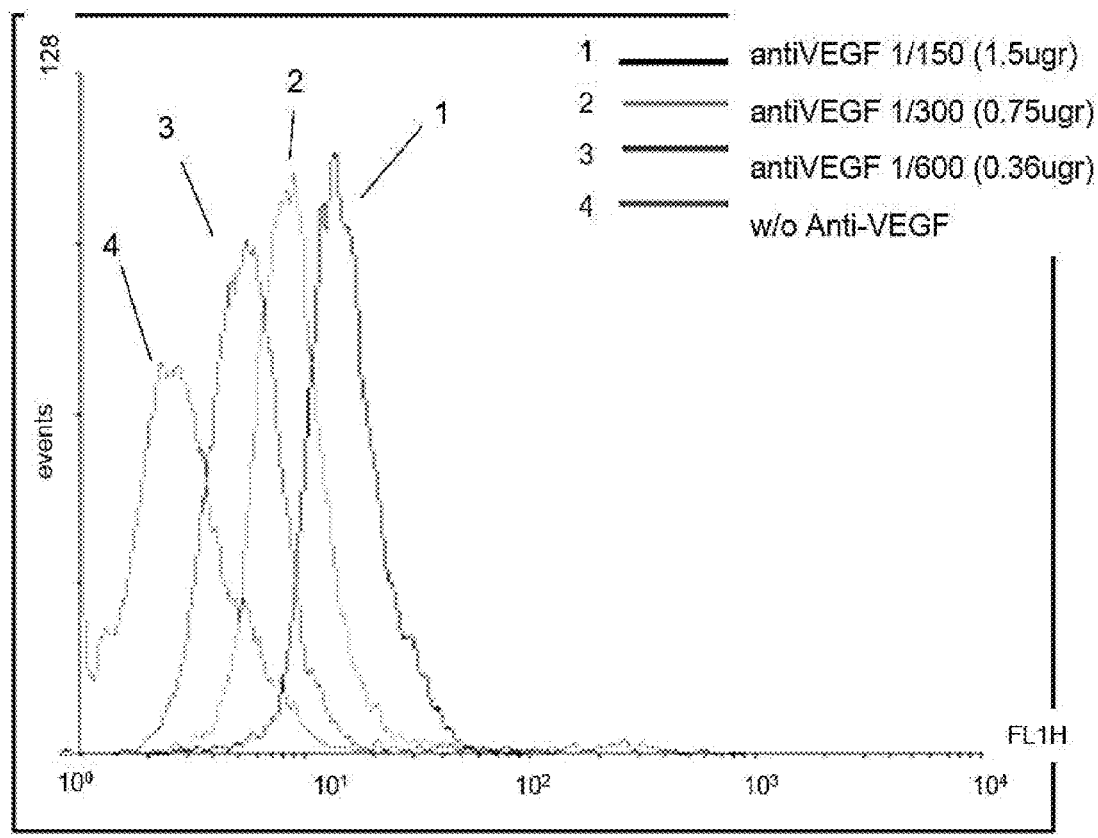

Functional validation of purified and refolded vNARs by flow cytometric assays was performed. For this purpose the cell line U937, monocytes of the myeloid lineage expressing different cytokines and chemokines, was used. The VEGF is constitutively expressed and secreted. This cell line is a model commonly used in the biomedical sciences. Binding capacity of the anti-VEGF vNAR V13, V19 and V32R at intracellular level was determined. The assay is described in example 6. The results for V13 are shown in FIGS. 15 and 16.

Molecules that are provided in the present invention were characterized in silico. Three-dimensional structures (tertiary) were prepared by homology modeling and refinement by molecular dynamics simulations.

The search for the optimal structure is conducted through three successive filters: 1) complex grouping based on their pattern of contacts; 2) preliminary energy analysis of the best representatives of each group; and 3) the molecular dynamics of the 2 complex protein—protein with better energy to find the most stable binding mode. The energy pattern of interactions was analyzed on the optimal structure.

As control, the interaction of a close homologue of V19 was analyzed with AMA1 protein (code PDB: 2Z8V)[18] that provided a reference free-energy-of-binding for this type of interactions.

In the case of the V19 and VEGF molecules, the optimum structure was made from existing homologous crystal structures, already published, in this case only missing residues were modeled and resulting structures were relaxed by molecular dynamics. The simulation time used was 5-6 ns. The structure of protein V19 was derived from the crystal structure PDB, code: 1VES[19], mutating Alanine 111 to Valine. The crystal of the VEGF protein was obtained from the PDB, code 1VPF[20]

The Root-mean-square deviation (RMSD) of proteins was measured, compared to the starting structure, throughout the dynamics in order to evaluate the stability of said structure. The smaller the RMSD value is more stable. The measurement was carried out both globally and at the level of residue.

Once the structures were analyzed, the protein—protein complex were obtained. For this, several protein-protein docking analysis of each complex was performed (VEGF-V19 and VEGF-V32R), in which different areas of bonding and orientations were evaluated until determine the optimal.

VEGF

Figure 17:
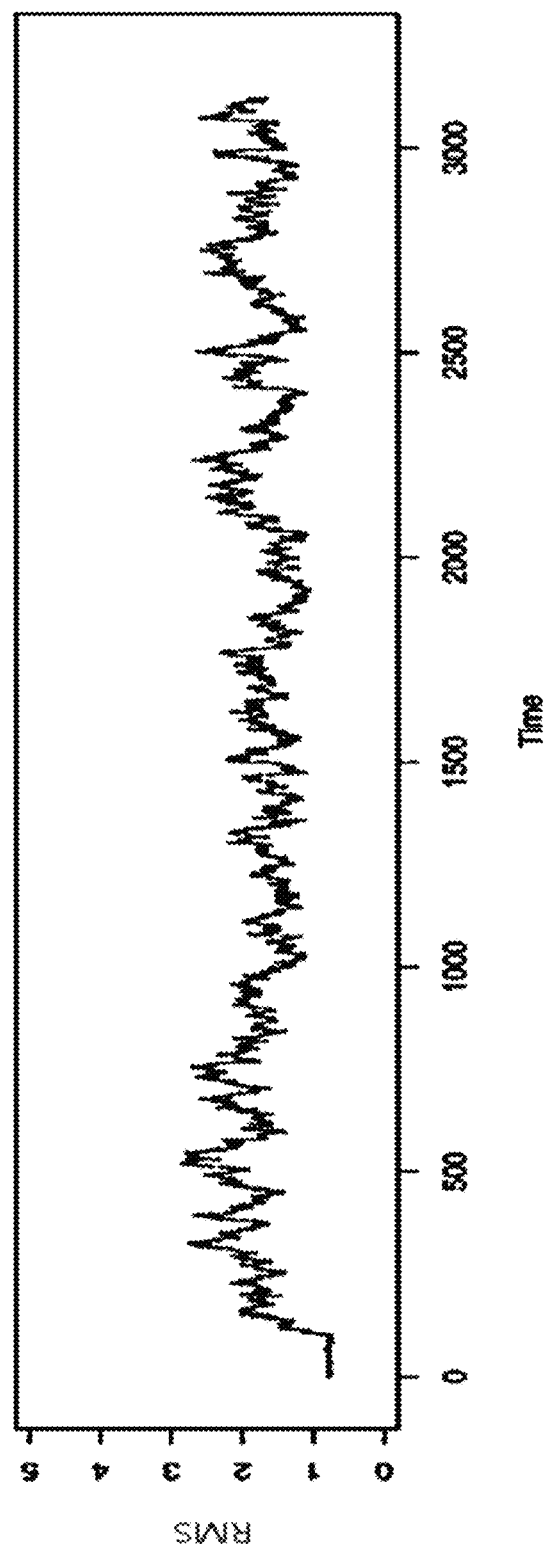
FIG. 17: Root Mean Square Deviation (RMSD) values measured during simulation of 6 ns for VEGF. The Y axis represents RMSD and the X axis the step number of the dynamic (each step are 2 picoseconds).

The fluctuation global values (RMSD) throughout dynamics did not exceeded 2 Å (FIG. 17), but there were many fluctuations around this value. The system is a dimer composed of two groups of β sheets connected by α helices of one or two turns. These structural motifs are highly mobile, which produce the cited fluctuations.

Figure 18:
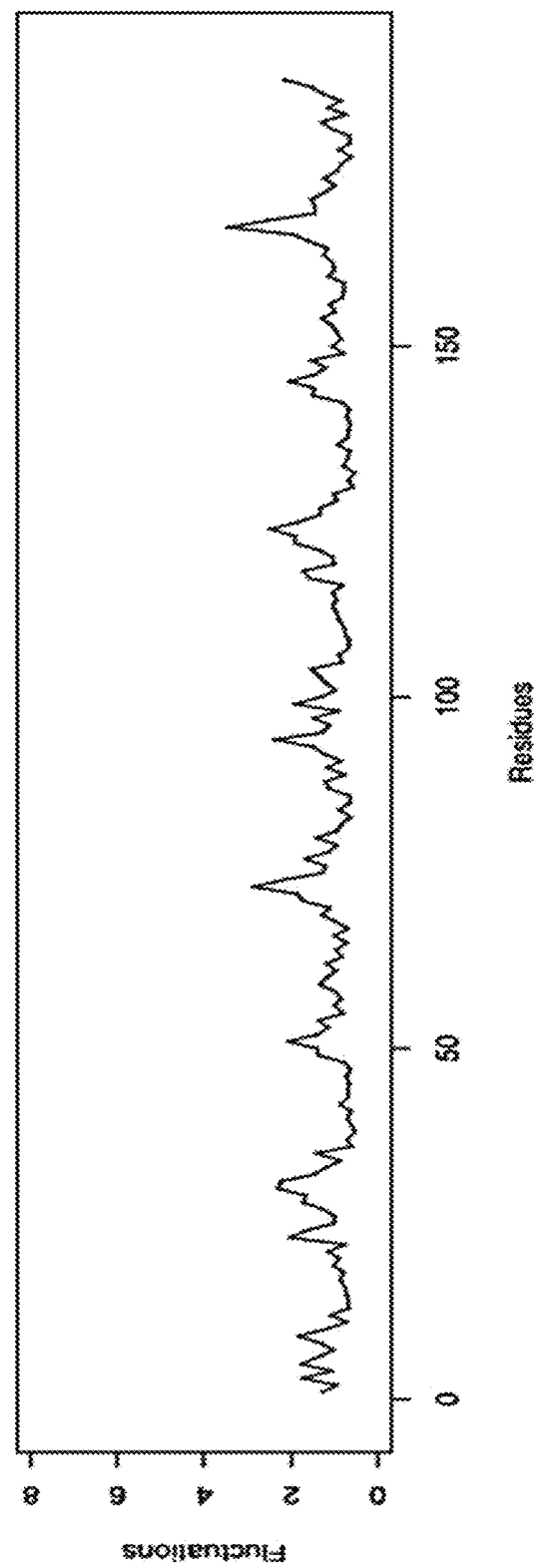
FIG. 18: Average fluctuations of VEGF residues. The Y axis represents RMSD values and the X axis the number of residues.

In general, the fluctuation values per residue did not exceeded 2 Å (FIG. 18), except interconnecting loops of β sheets, which are located approximately every 25 residues. Since it is a dimer, the fluctuation pattern is repeated for both subunits.

Figure 19:
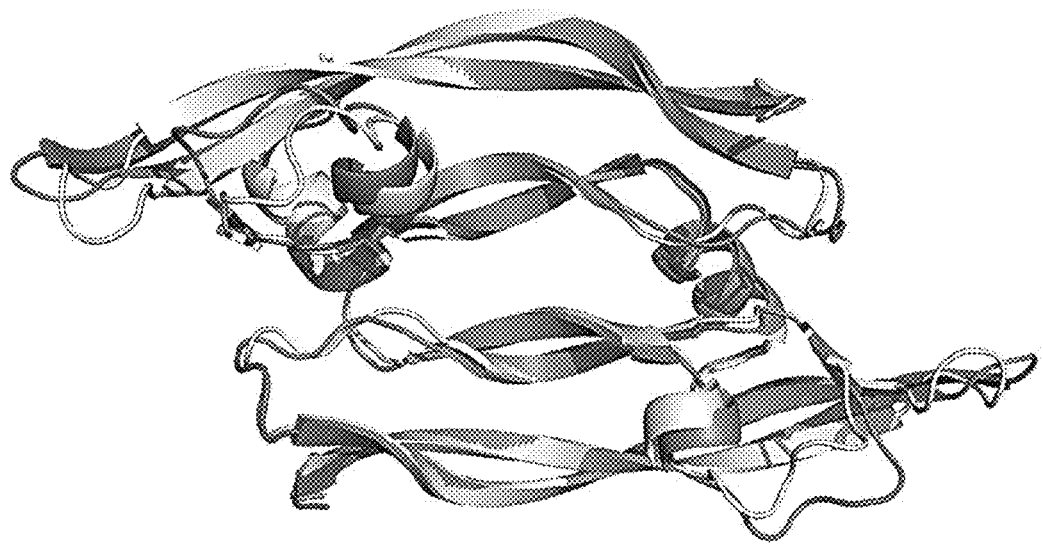
FIG. 19: Overlay of the initial (gray) and last (cyan) structure from the dynamic of VEGF.

The superposition of the initial structure coincides with the minimized average structure of the last 500 ps of simulation (FIG. 19).

V19

Figure 20:
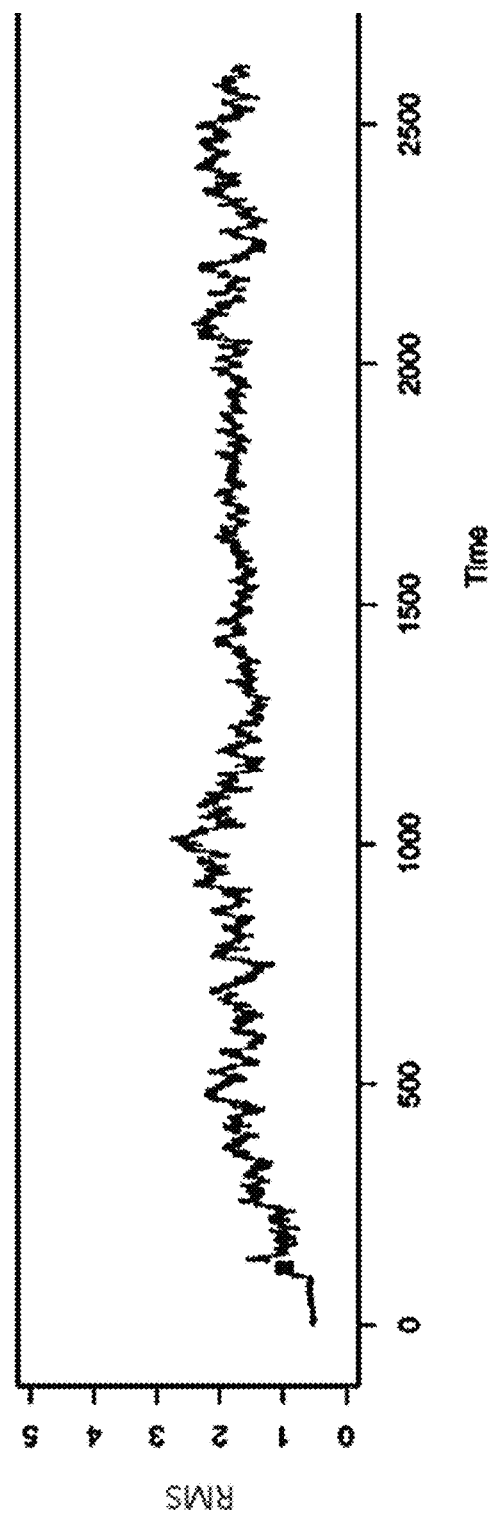
FIG. 20: Root Mean Square Deviation (RMSD) values measured during simulation of 5 ns for vNAR V19. The Y axis represents RMSD and the X axis the step number of the dynamic (each step are 2 picoseconds).

With respect to the overall fluctuation, the system was stable. The global RMSD values throughout the dynamics did not exceeded 2 Å (FIG. 20). The structure of V19 consists of various β sheets connected by loops, the mobility of these loops and their reorientation to the solvent makes the RMSD of the protein to fluctuate.

Figure 21:
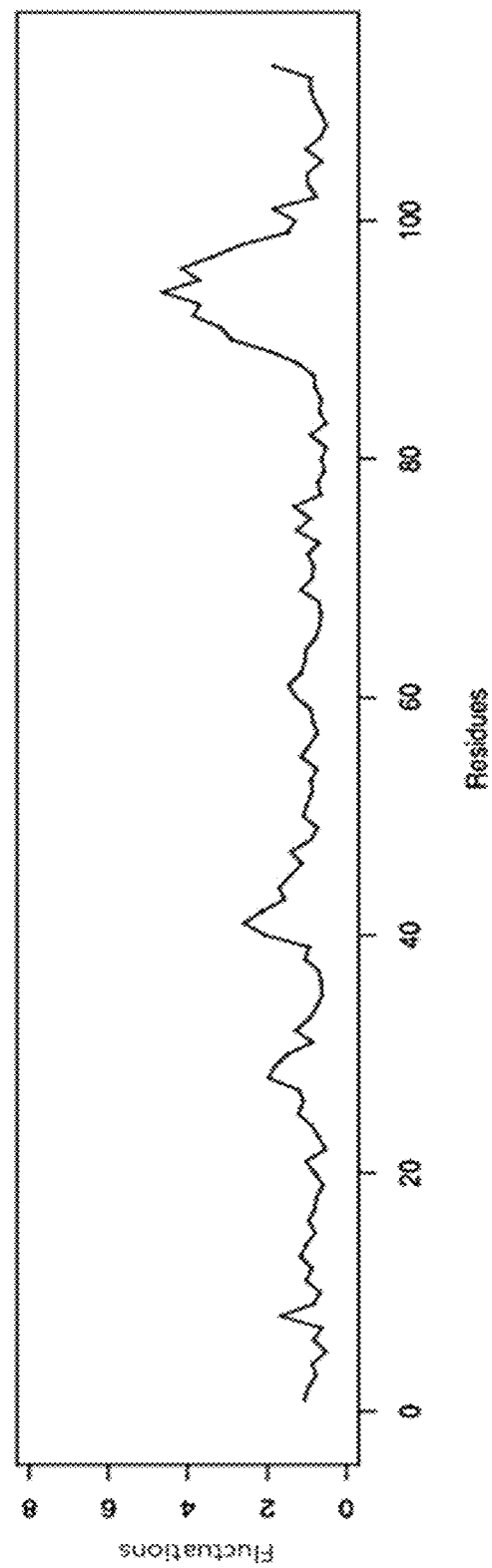
FIG. 21: Average fluctuations of vNAR V19 residues. The Y axis represents RMSD values and the X axis the number of residues.

The fluctuation by residue was low (FIG. 21), not exceeding generally 2 Å, except for the region between the residues 85-100, where values for up to 4 Å are achieved. This area corresponds to the variable region of the antibody, consisting of two β sheets interconnected by a loop; it has high flexibility and it is the recognition site for binding to other proteins.

Figure 22:
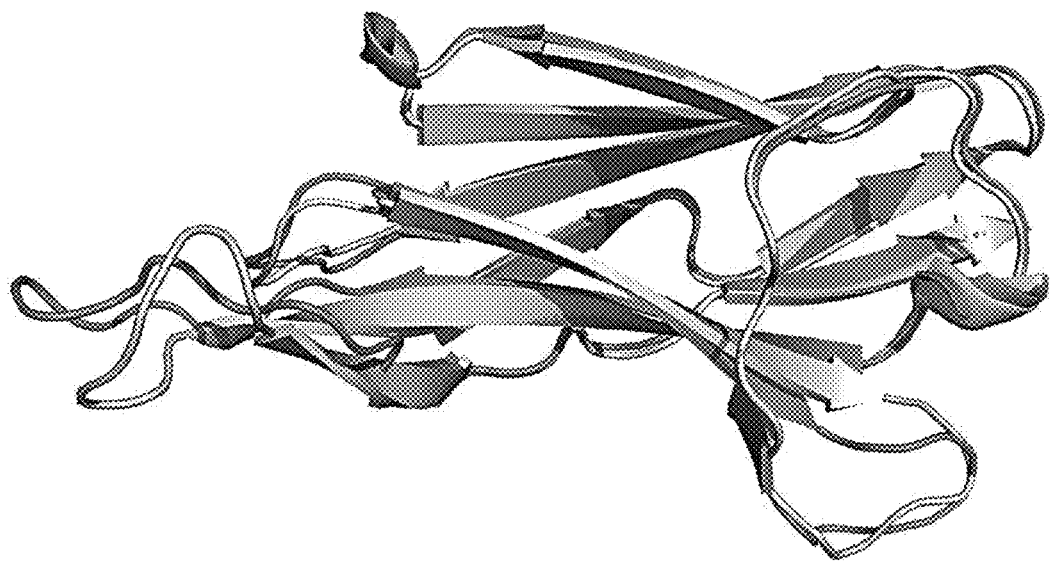
FIG. 22: Overlay of the initial (gray) and last (cyan) structure from the dynamic of vNAR V19.

When overlaying the initial structure with the minimized average structure of the last 500 ps of simulation, similarity was observed between the structures except the loop mentioned above, located between residues 85-100 (FIG. 22).

V32R

The homology modeling was performed and it was refined by molecular dynamics. It started from a model based on the structures 2Z8V[18] y 2I26[21], with a simulation time of 20 ns. The RMSD value was measured throughout the dynamic, with respect to the starting structure, in order to evaluate the stability of said structure, both globally and at the level of residue.

Figure 23:
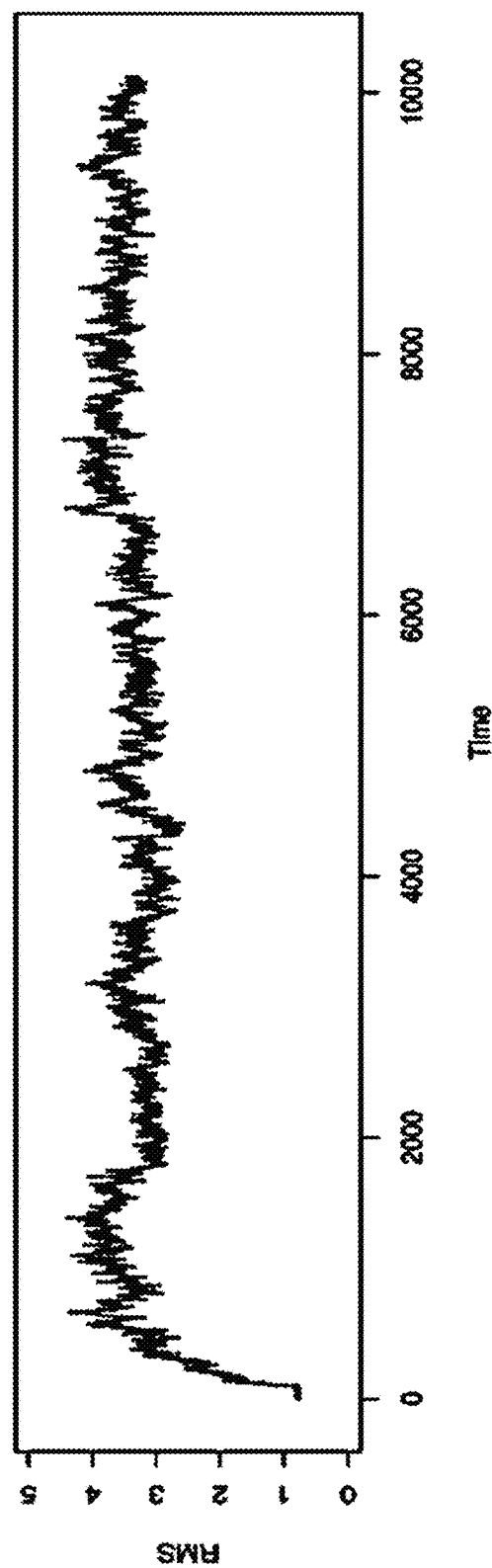
FIG. 23: Root Mean Square Deviation (RMSD) values measured during simulation of 20 ns for vNAR V32R. The Y axis represents RMSD and the X axis the step number of the dynamic (each step are 2 picoseconds).

The overall fluctuation reached 4 Å. In the first nanoseconds the model moved away from its initial structure to remain stable for the rest of the simulation (FIG. 23).

Figure 24:
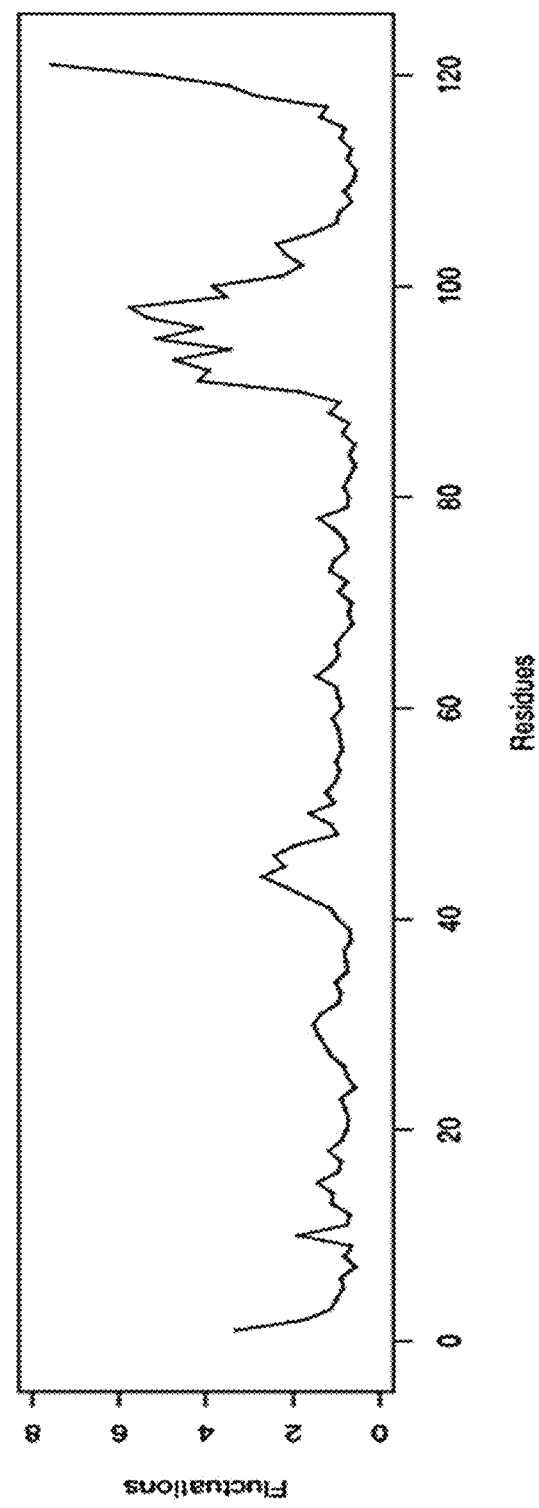
FIG. 24: Average fluctuations of vNAR V32R residues. The Y axis represents RMSD values and the X axis the number of residues.

The fluctuation by residue showed significant fluctuations in two regions lying between residues 40-50 and 90-110 reaching values of more than 4 Å. Once the unfolding of the loop is produced, corresponding to residues 90-110, the protein was stable. The remaining fluctuations were accumulated in the loops that connect the β sheets, as well as the C-terminal end (see FIG. 24).

Figure 25:
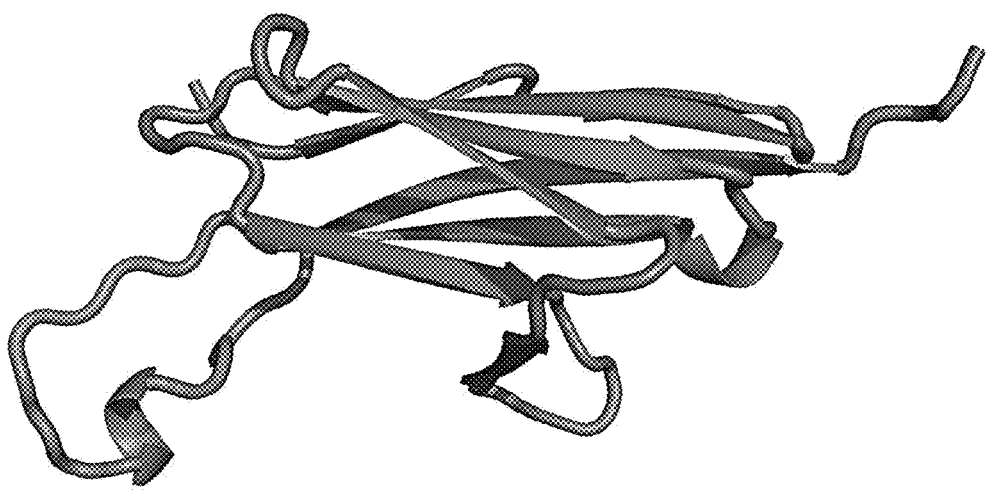
FIG. 25: Image of vNAR V32R structure indicating by color code the fluctuations observed during the dynamic, from red (regions with higher mobility) to blue (more static).
Figure 26:
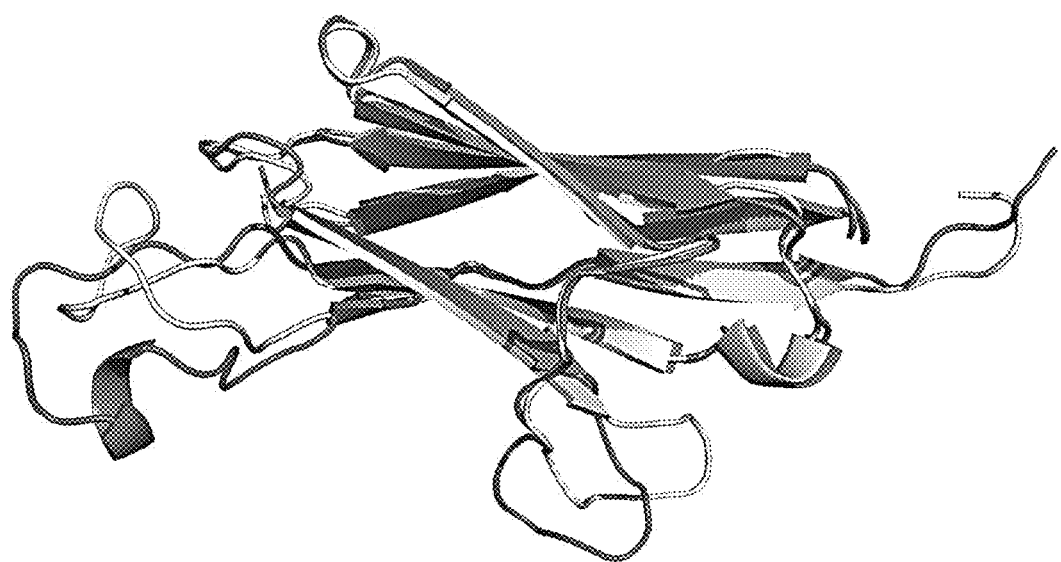
FIG. 26: Overlay of the initial (gray) structure of V32R over the last (cyan) structure of the dynamic with the most mobile regions highlighted in dark blue.
Figure 27:
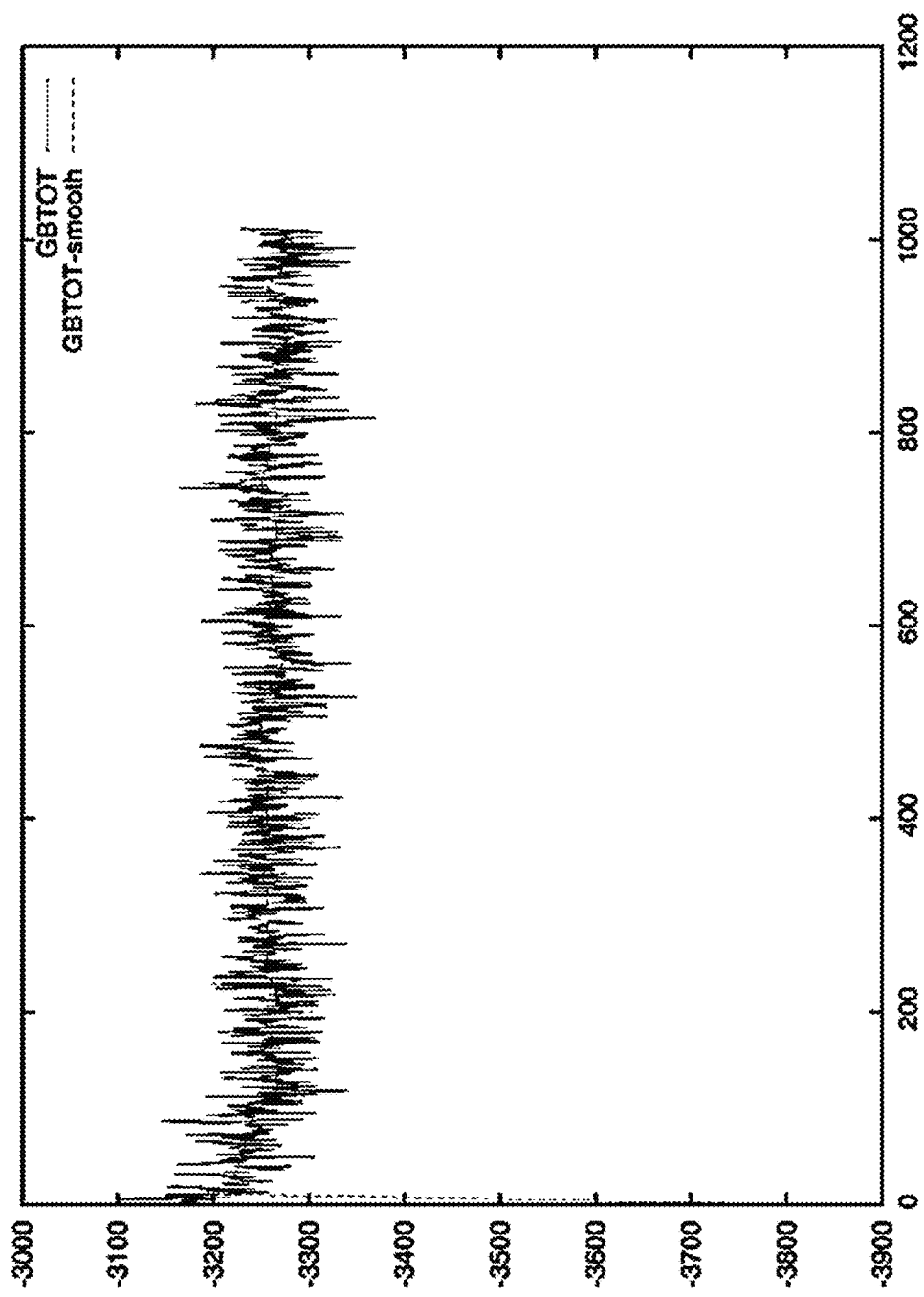
FIG. 27: Values of free energy of binding for each instant of the dynamic of vNAR V32R (each step are 2 picoseconds). The Y axis represents the global energy in kcal/mol and the X axis the step number of the dynamic.
Figure 28:
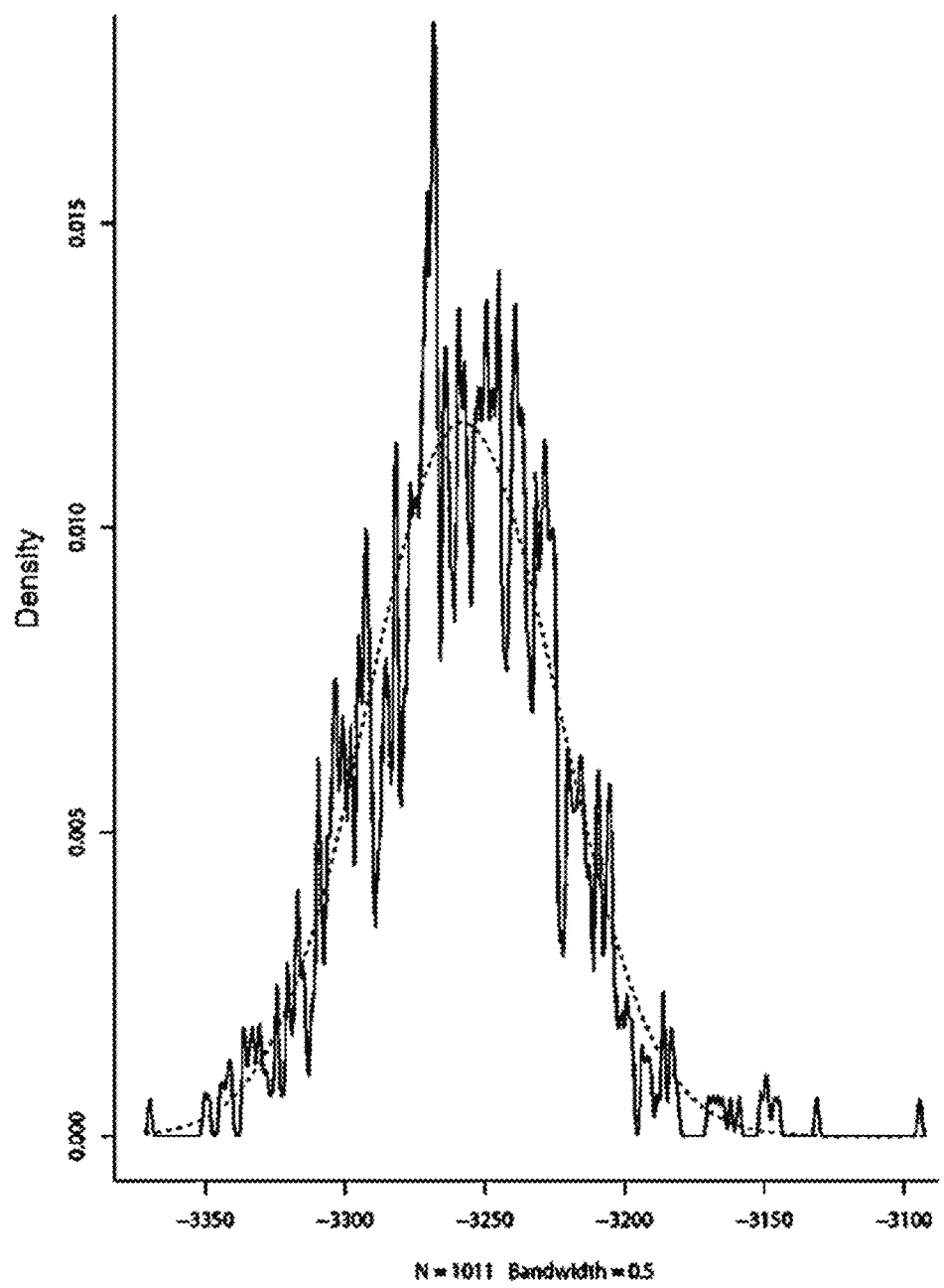
FIG. 28: Density energy values achieved by vNAR V32R during the dynamic. The Y axis shows the density and the X axis shows the global energy value in kcal/mol. The dotted line represents the Gaussian function associated with the distribution.
Figure 31:
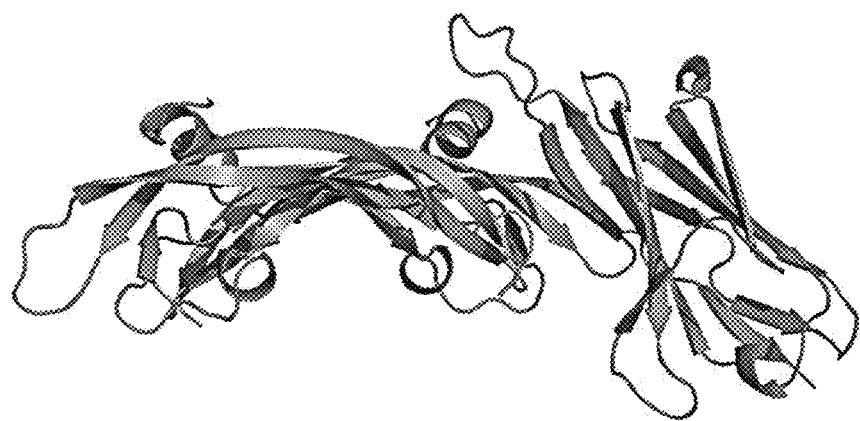
FIG. 31: Model 3 of the complex VEGF (chains in green and cyan) with vNAR V19 (chain in magenta).
Figure 32:
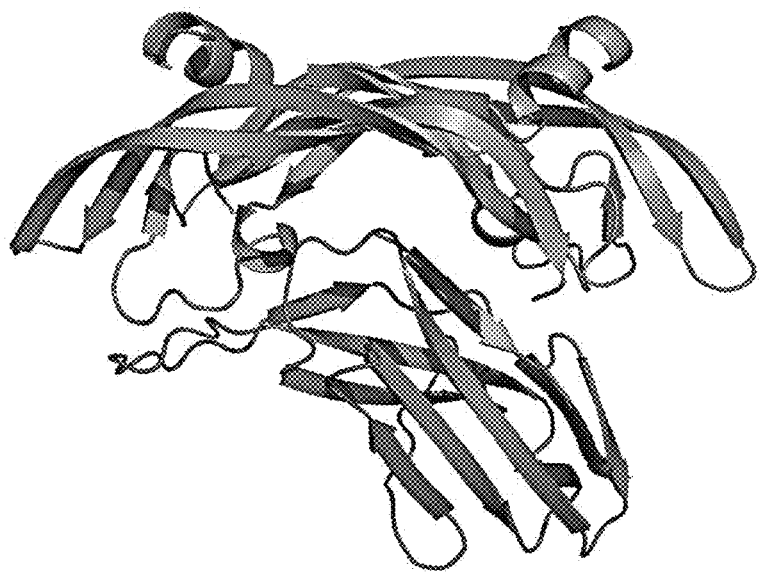
FIG. 32: Model 4 of the complex VEGF (chains in green and cyan) with vNAR V19 (chain in magenta).
Figure 33:
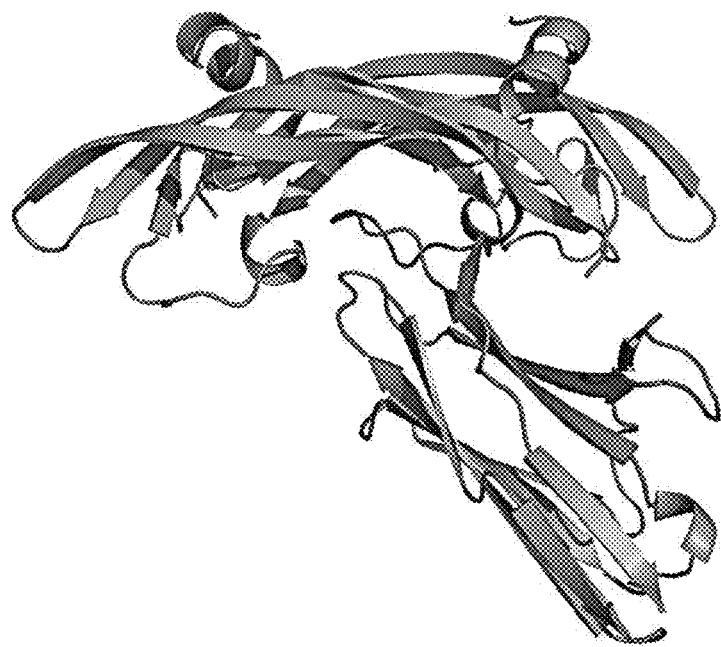
FIG. 33: Model 5 of the complex VEGF (chains in green and cyan) with vNAR V19 (chain in magenta).

FIG. 25 shows an image wherein the most mobile zones of vNAR V32R are represented. In the superposition of the initial structure and the minimized average of the last 500 ps, it was seen that the two structures are similar. Fluctuations were detected in residues G89-Y105 and R39-R49 (FIG. 26). The energy analysis of V32R shows that the most probable energy value for the molecule is −3250 Kcal/mol (FIGS. 27 and 28).

Protein-Protein Docking

Interaction models were generated using techniques of protein-protein docking. The results obtained were filtered in order to find the different binding zones and the optimum orientation. The filtering steps were the following:

1) Grouping of complexes based on their contact pattern and removal of solutions in which vNARs do not interact with VEGF through the area of the antibody recognition loop.
2) Study of receptor and ligand electrostatics by calculations of APBS (Adaptive Poisson-Boltzmann Solver) and elimination of those solutions where electrostatic shocks are observed.
3) Preliminary energy analysis of the best representatives of each group. Energy calculation of the other models, and correction of its value in function of the contact surface between both proteins.
4) Selecting models to study based on the following criteria:
   The total energy value (kcal/mol)
   The Van der Waals energy
   The Van der Waals energy together with energy of the hydrogen bridges Protein-Protein Docking V19-VEGF After this filtering process 5 bonding patterns were obtained (FIGS. 29-33) and molecular dynamics was applied thereto, in order to study the structural, energetic stability and contact map.

Comparative Energy with Respect to the Control Model

In order to try to choose the models that best represent the binding mode between VEGF and V19, a comparative study of the interaction energy of each was made with reference to the control complex (homologue of V19 in crystal of 2Z8V). The energy values are corrected based on the interaction surface; since the energy is calculated as a summatory, a significant correlation between the values obtained and the involved surface was present. On the other hand, the total energy consists of a Coulomb term; another associated with Van der Waals forces and it is completed with the strength of the hydrogen bridges. In the case of the complex of AMA1-homologue of V19, it was seen that when selecting the actual interactions of the artifactuals, it was more discriminating to do without the Coulomb term in the energy evaluation. The decomposition is also presented in results of Table 3.

Table 3 shows the interaction energy (kcal/mol) of the models chosen for the VEGF-V19 complex. Energy values and occluded surface have been calculated for the minimized average structure of the last 500 ps of dynamics. ($E_{total}$: total energy; $E_{vdw}$: Van der Waals energy; $E_{HB}$: energy of hydrogen bridges; SASA: solvent accessible surface area).

TABLE 3

Interaction energy (kcal/mol) of the models chosen for the VEGF-V19 complex

| MODELS | $E_{total}$ | $E_{vdw}$ | $E_{HB}$ | SASA | $E_{total}$/SASA | $E_{vdw}$/SASA | $E_{vdw+HB}$/SASA |
|---|---|---|---|---|---|---|---|
| control | −144.04 | −101.30 | −19.42 | 893.50 | 0.1612 | 0.1134 | 0.1351 |
| model 1 | −139.50 | −89.09 | −11.03 | 929.70 | 0.1500 | 0.0958 | 0.1077 |
| model 2 | −62.86 | −55.69 | −5.83 | 669.70 | 0.0939 | 0.0832 | 0.0919 |
| model 3 | −63.17 | −50.18 | −7.74 | 446.80 | 0.1414 | 0.1123 | 0.1296 |
| model 4 | −100.36 | −76.29 | −11.58 | 794.10 | 0.1264 | 0.0961 | 0.1107 |
| model 5 | −97.58 | −83.25 | −10.12 | 912.80 | 0.1069 | 0.0912 | 0.1023 |

In view of the data, and the structural stability studied in the previous sections, the model 2 was discarded as the mode of binding between VEGF and v19.

Comparative of Contact with Respect to the Control Model

FIG. 34 shows the contact matrices of each of the models to be compared with contacts of the control complex (homologue of V19 in crystal of 2Z8V). In view of the interactions between homologue of V19 and its receptor in the crystal, we can say that there are three areas of interaction in V19: zone 1, which corresponds to the X-terminal end (residues 1-2); zone 2 comprised between residues 25-35, which corresponds to the secondary recognition loop and zone 3, involving the residues between positions 89 and 103 and which corresponds to the main loop of recognition.

For interaction maps from the models of complex VEGF-V19 (FIG. 35a-35e), the expected repetition of the binding zones view for V19 in the control complex was confirmed.

With all the data obtained, together with the fluctuations pattern, it was shown that the model of our molecule matched MODEL 1 (FIG. 29), as it provides the best structural stability and interaction energy throughout the simulation, besides having a contact pattern similar to that seen in the control complex (homologue of vNAR V19 with AMA1).

Protein-Protein Docking vNAR V32R-VEGF

Four modes of binding between VEGF and vNAR V32R (FIGS. 36-39) covering the main orientations were isolated. Energies along molecular dynamics of 20 ns were analyzed in order to determine its structural and energetic stability as well as its contact map. To do this, we start with the structures obtained after refining VEGF and vNAR V32R. Subsequently, interaction models were generated using techniques of protein-protein docking. The results obtained were filtered in order to find the different binding zones, and the optimum orientation following the same protocol as in the previous case.

Comparative Energy with Respect to the Control Model

In order to try to choose the models that best represent the binding mode between VEGF and V32R, a comparative study of the interaction energy of each was made with reference to the control complex (homologue of V19 in crystal of 2Z8V). The energy values were corrected based on the interaction surface; since the energy was calculated as a summatory, a significant correlation between the values obtained and the involved surface was present. On the other hand, the total energy consists of a Coulomb term; another associated with Van der Waals forces and it is completed with the strength of the hydrogen bridges. In the case of the complex of AMA1-homologue of V19, it was seen that when selecting the actual interactions of the artifactuals, it was more discriminating to do without the Coulomb term in the energy evaluation. Therefore, in this case this type of decomposition is reiterated. Table 4 shows the interaction energy (kcal/mol) of the models chosen for the VEGF-V32R complex. Energy values and occluded surface have been calculated for the minimized average structure of the last 500 ps of dynamics. ($E_{total}$: total energy; $E_{vdw}$: Van der Waals energy; $E_{HB}$: energy of hydrogen bridges; SASA: solvent accessible surface area).

TABLE 4

Interaction energy (kcal/mol) of the models chosen for the VEGF-V32R complex

| MODELS | $E_{total}$ | $E_{vdw}$ | $E_{HB}$ | SASA | $E_{total}$/SASA | $E_{vdw}$/SASA | $E_{vdw+HB}$/SASA |
|---|---|---|---|---|---|---|---|
| control | −144.04 | −101.30 | −19.42 | 893.50 | 0.1612 | 0.1134 | 0.1351 |
| model 1 | −127.05 | −77.01 | −15.99 | 827.50 | 0.1535 | 0.0930 | 0.1124 |
| model 2 | −75.10 | −67.56 | −6.29 | 655.60 | 0.1146 | 0.1030 | 0.1126 |
| model 3 | −116.46 | −63.55 | −17.26 | 816.30 | 0.1427 | 0.0779 | 0.0990 |
| model 4 | −74.12 | −48.93 | −7.39 | 645.30 | 0.1143 | 0.0758 | 0.0873 |

In view of the data, and the structural stability studied in the previous sections, the model 4 was discarded as the mode of binding between VEGF and v32R.

Comparative of Contact with Respect to the Control Model

Figure 34:
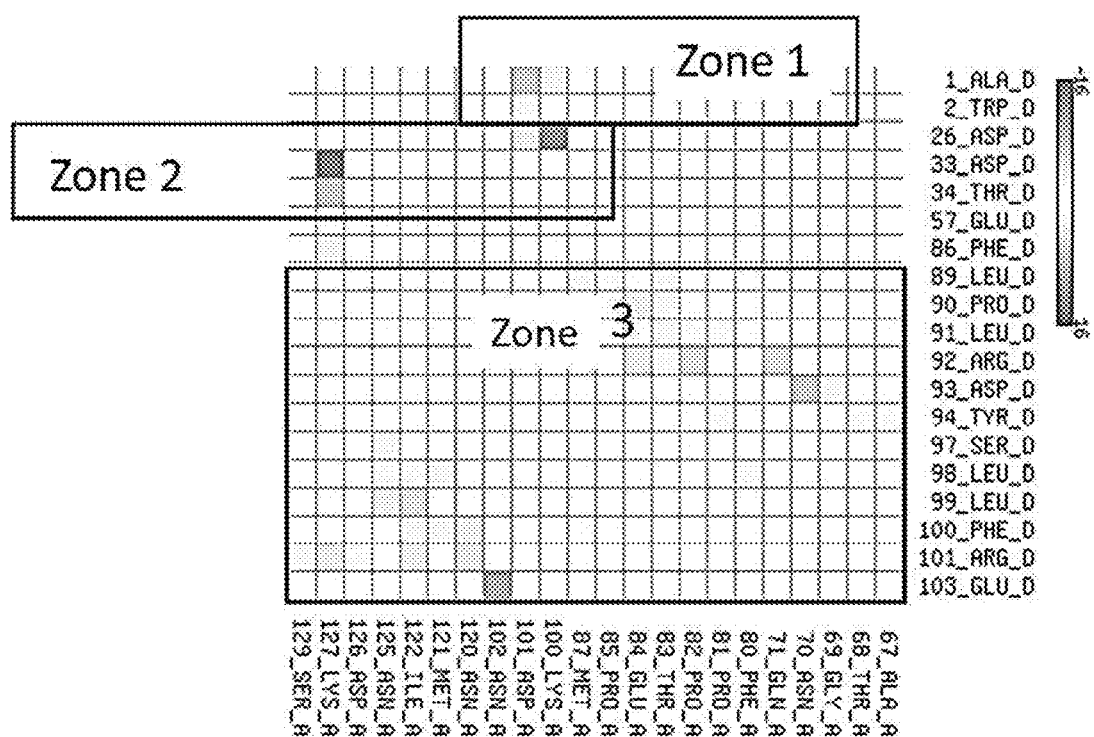
FIG. 34: Map of interactions for complex control (2Z8V). Interactions between the V19 homolog (chain D displayed in vertical) and its receptor (chain A displayed in horizontal) are shown in the image. The color scale is based on the value of the interaction energy: the redder is the representation, the more favorable interaction; and the bluer, less favorable.
Figure 35A:
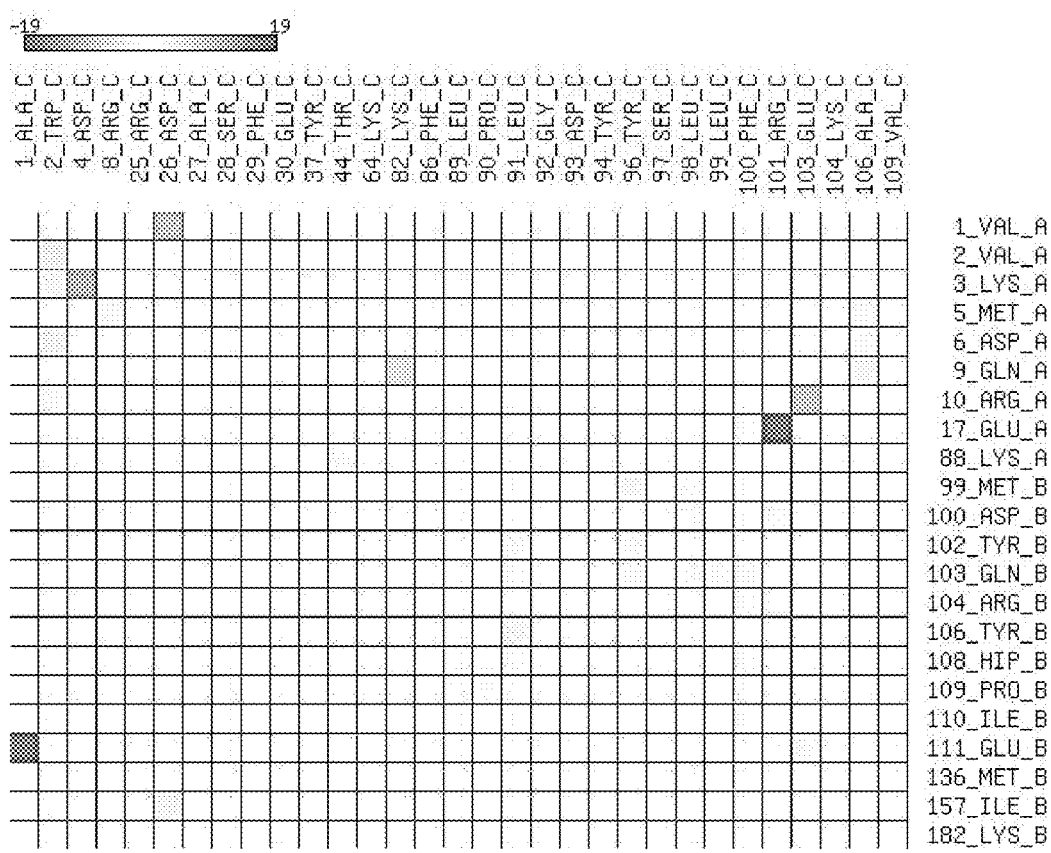
FIG. 35a, 35b, 35c, 35d, 35e: Map of interactions for complex VEGF-V19. Interactions between V19 (chain C displayed in vertical) and its receptor (chain A and chain B displayed in horizontal) are shown in the image. The color scale is based on the value of the interaction energy: the redder is the representation, the more favorable interaction; and the bluer, less favorable.
Figure 35B:
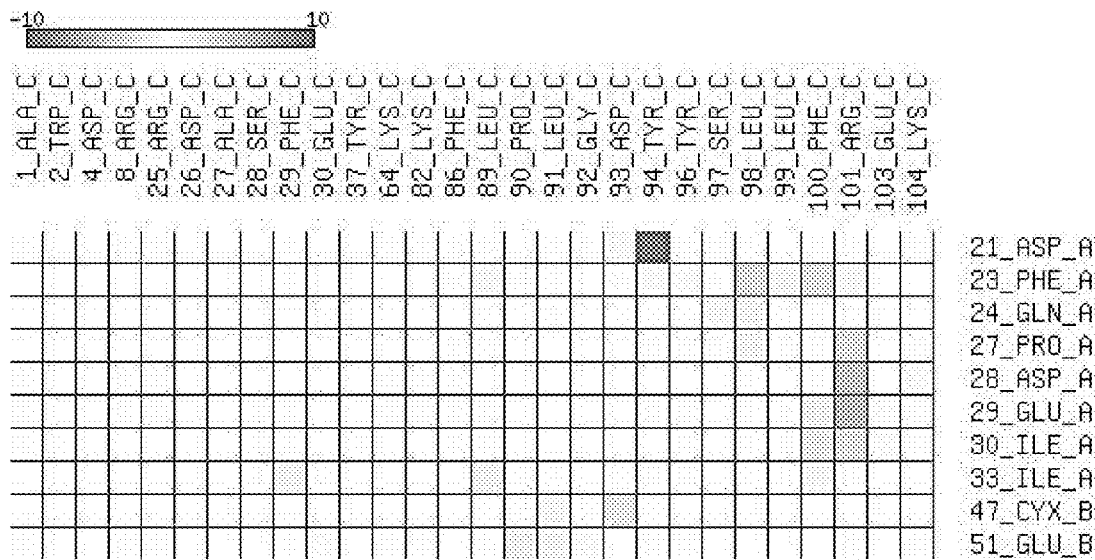
Figure 35C:
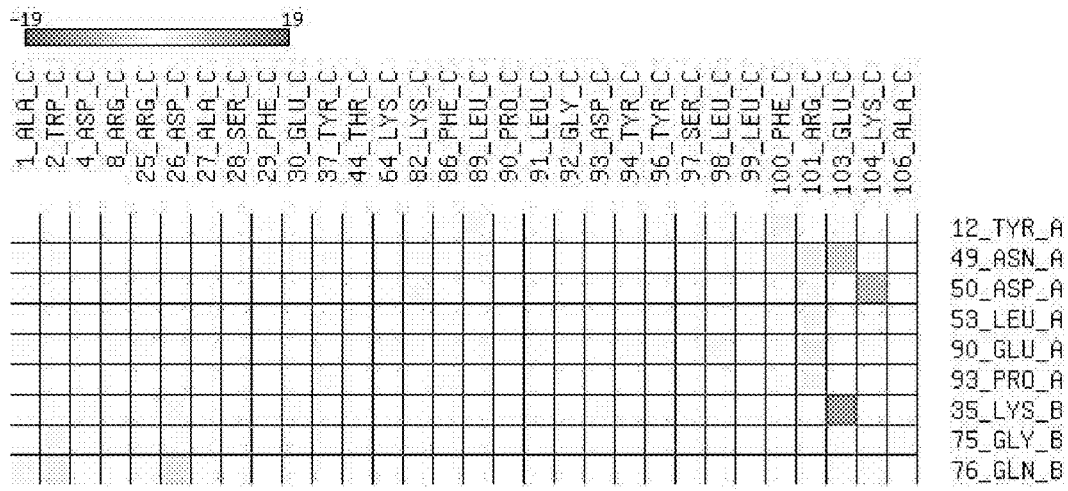
Figure 35D:
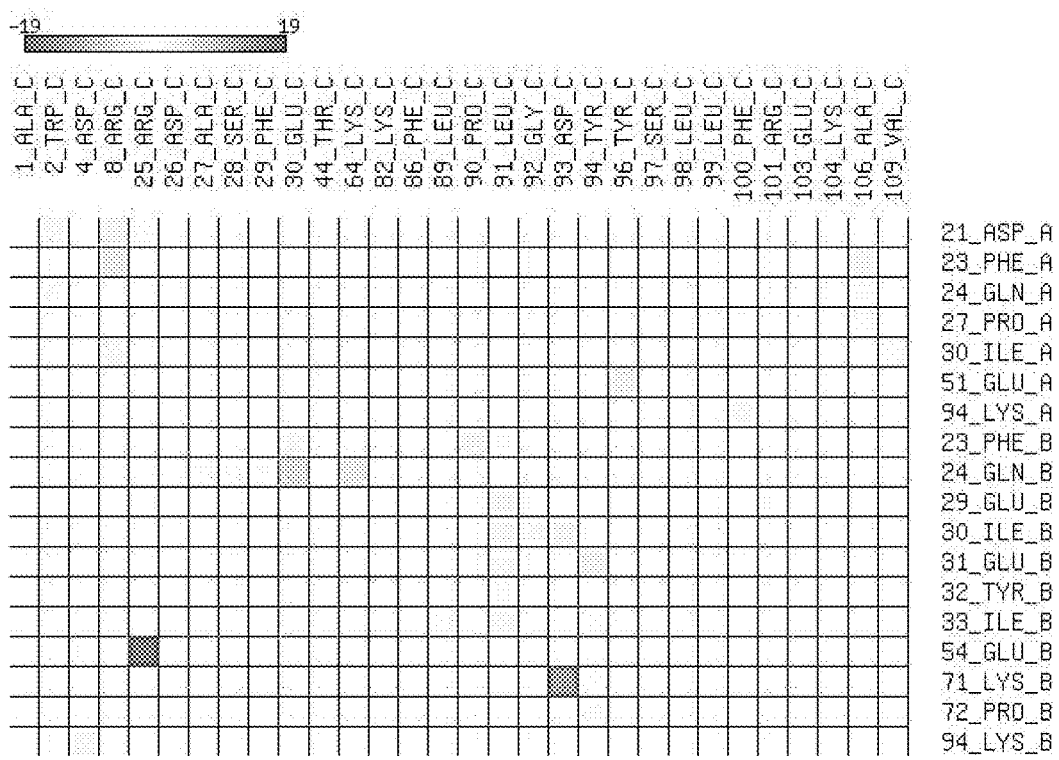
Figure 35E:
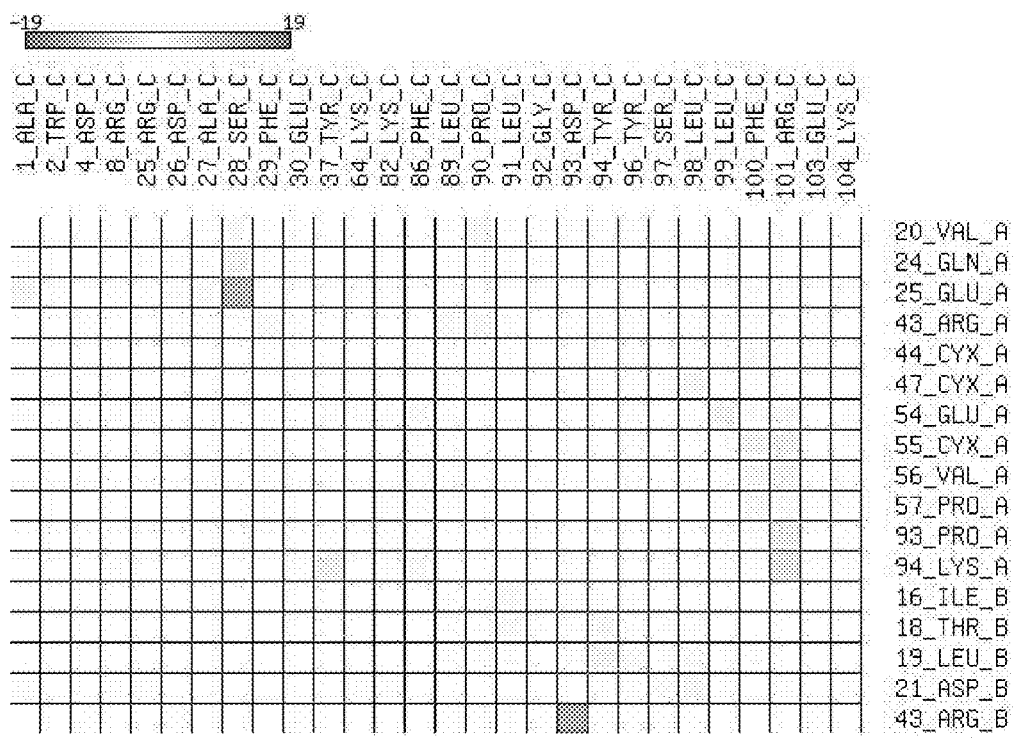

As in the case of V19-VEGF docking, the contact matrices of each of the models to be compared with contacts of the control complex (homologue of V19 in crystal of 2Z8V, FIG. 34) are considered. In the case of the interaction maps of the complex models VEGF-V32F (FIG. 40a-40d), it is expected the binding zones seen for V19 in the control complex are repeated.

Figure 38:
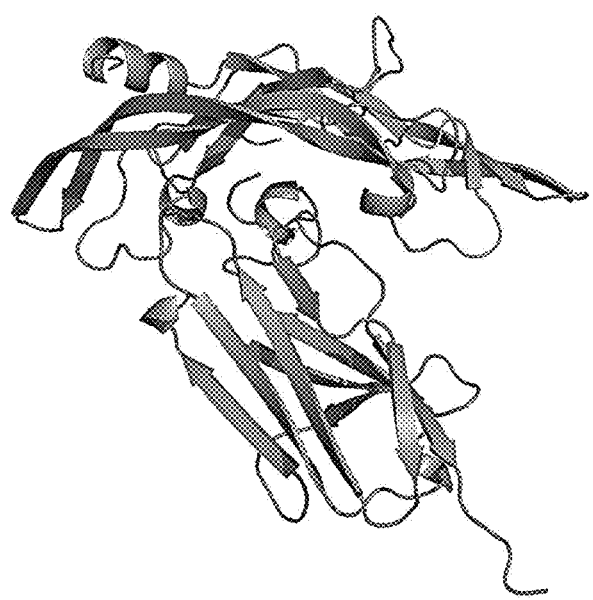
FIG. 38: Model 3 of the complex VEGF (chains in green and cyan) with vNAR V32R (chain in magenta).
Figure 39:
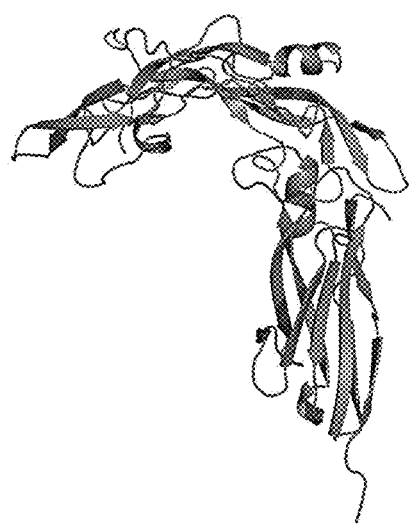
FIG. 39: Model 4 of the complex VEGF (chains in green and cyan) with vNAR V32R (chain in magenta).
Figure 40A:
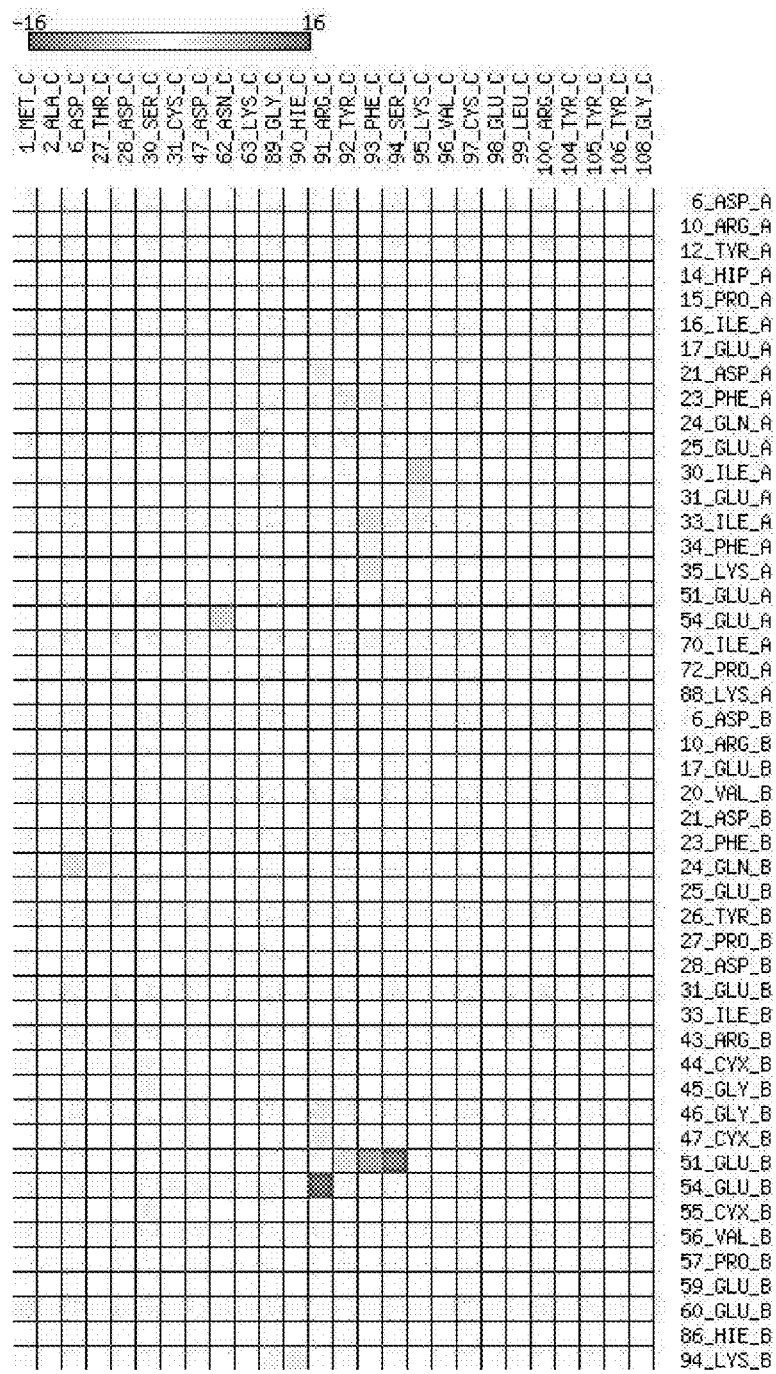
FIGS. 40a, 40b, 40c, 40d: Map of interactions for complex VEGF-V32R. Interactions between V32R (chain C displayed in vertical) and its receptor (chain A and chain B displayed in horizontal) are shown in the image. The color scale is based on the value of the interaction energy: the redder is the representation, the more favorable interaction; and the bluer, less favorable.
Figure 40B:
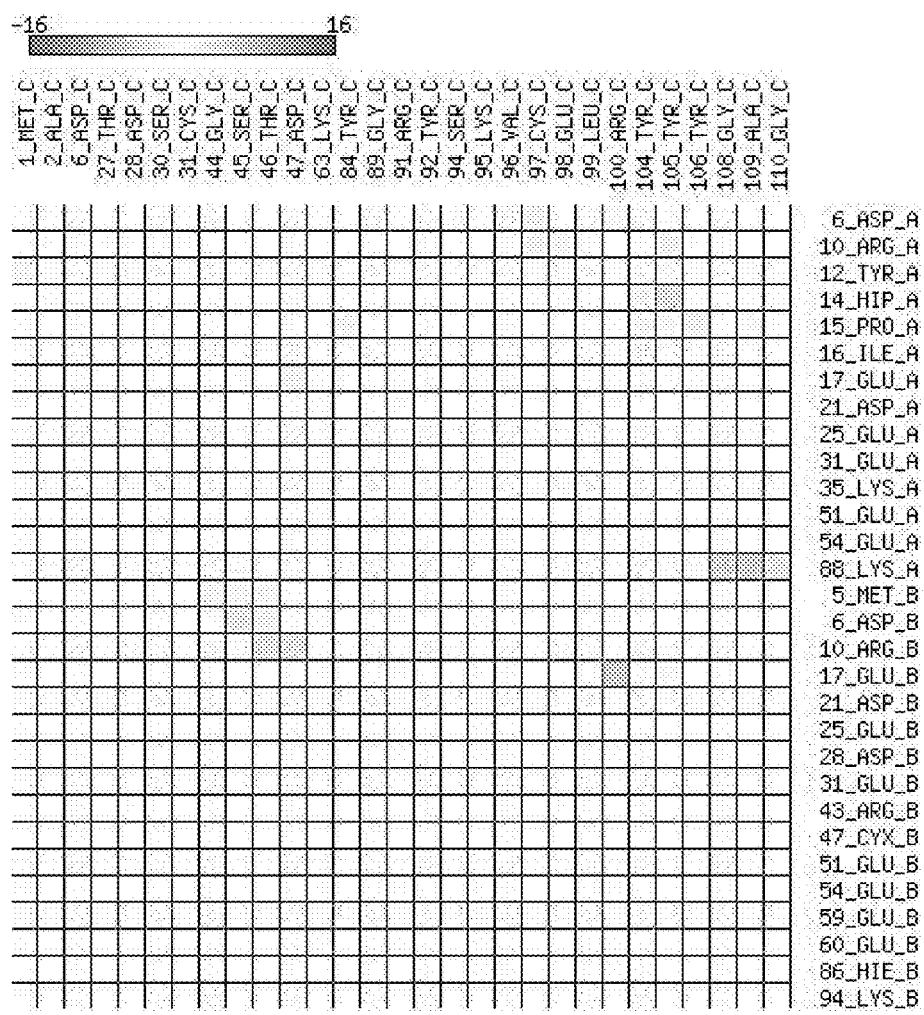
Figure 40C:
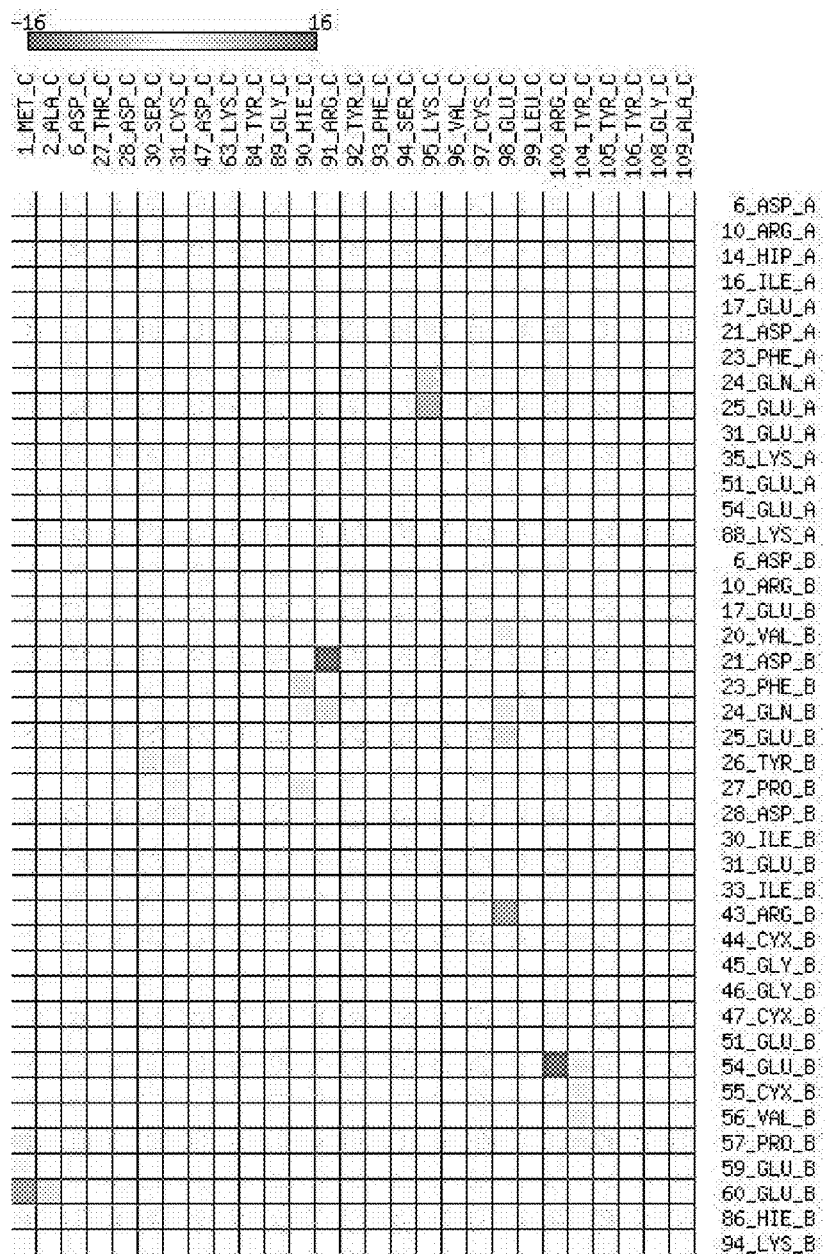
Figure 40D:
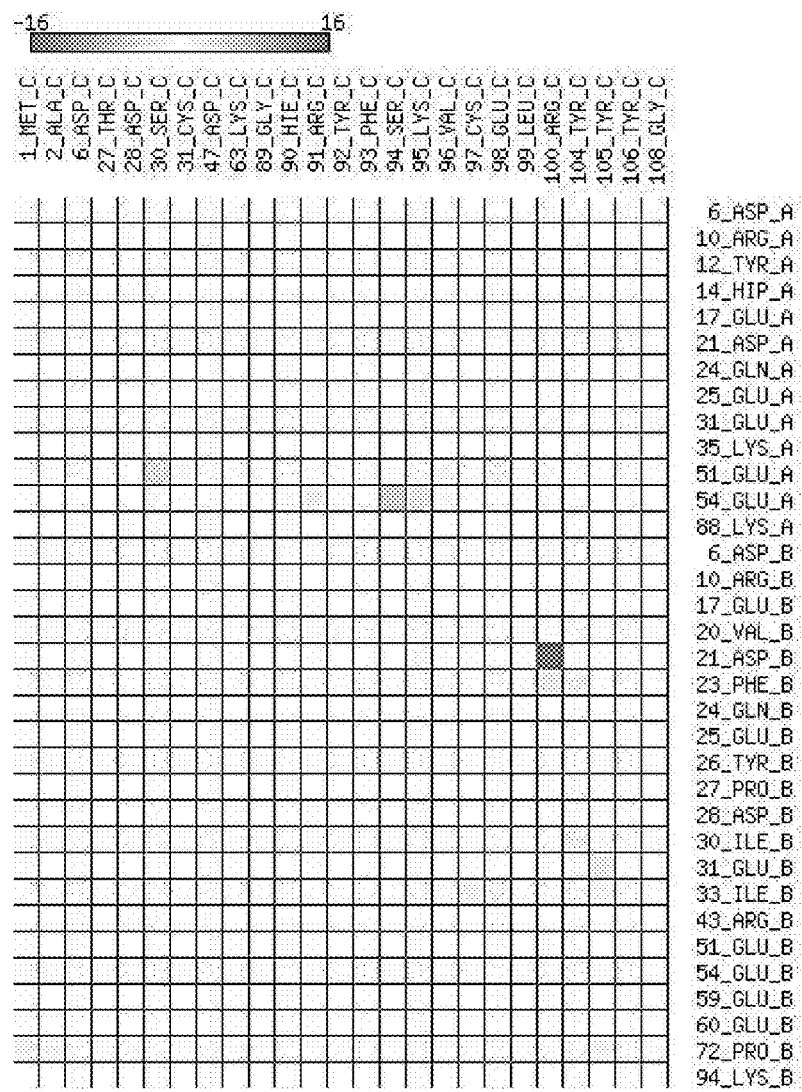

With all the data obtained, together with the fluctuations pattern, it was shown that the model of our molecule matched MODEL 3 (FIG. 38), as it is considered optimal in function of its structural stability and interaction energy. Besides, it reproduced the pattern of interactions observed in the control complex. Based on all previous data, additional information was obtained that will provide a wider support for the characterization of the molecules of the present invention:

Disulfide Bridges

The disulphide bridges (SS) present in proteins treated in the study are shown below. Specifically, the cysteines forming said disulfide bridges are marked with an X in yellow on the sequences in FASTA format (text-based format for representing either nucleotide sequences or peptide sequences, in which nucleotides or amino acids are represented using single-letter codes). Following is a description by pairs of cysteine that form the bridge. Numbering of proteins begins with residue number 1 and it is continuous although chain is changed.

VEGF

Figure 41:
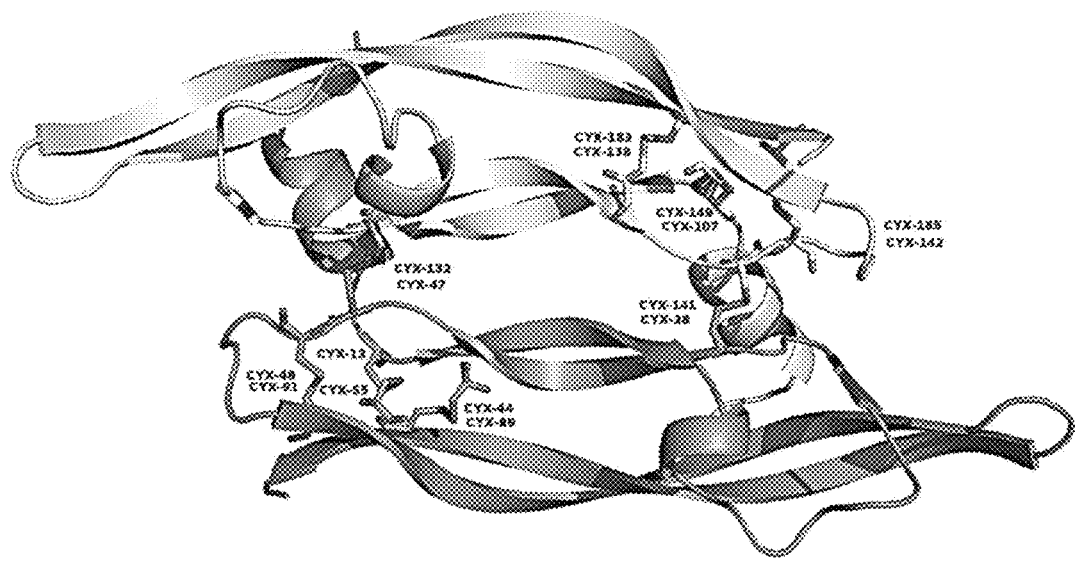
FIG. 41: Disulfide bridges of VEGF.

A dimer that has three disulfide bridges in each subunit and two bridges between subunits, with a total of eight disulfide bridges, which imply 16 cysteines (FIG. 41 and Table 5).

```
>VEGF: A|PDBID|CHAIN|SEQUENCE (SEQ. ID. NO. 7):
  1    VVKFMDVYQRSYXHPIETLVDIFQEYPDEIEYIFKPSXVPLMRXGGXXNDEGLEXVPTEE
 61    SNITMQIMRIKPHQGQHIGEMSFLQHNKXEXRPK

>VEGF: B|PDBID|CHAIN|SEQUENCE (SEQ. ID. NO. 7):
 95    VVKFMDVYQRSYXHPIETLVDIFQEYPDEIEYIFKPSXVPLMRXGGXXNDEGLEXVPTEE
155    SNITMQIMRIKPHQGQHIGEMSFLQHNKXEXRPK
```

TABLE 5

Pairs of Cysteines forming S—S bond in VEGF

| SUBUNIT A | SUBUNIT B | INTERSUBUNIT |
|---|---|---|
| 13-55 | 107-149 | 38-141 |
| 44-89 | 138-183 | 47-132 |
| 48-91 | 142-185 | | vNAR V19

Figure 42:
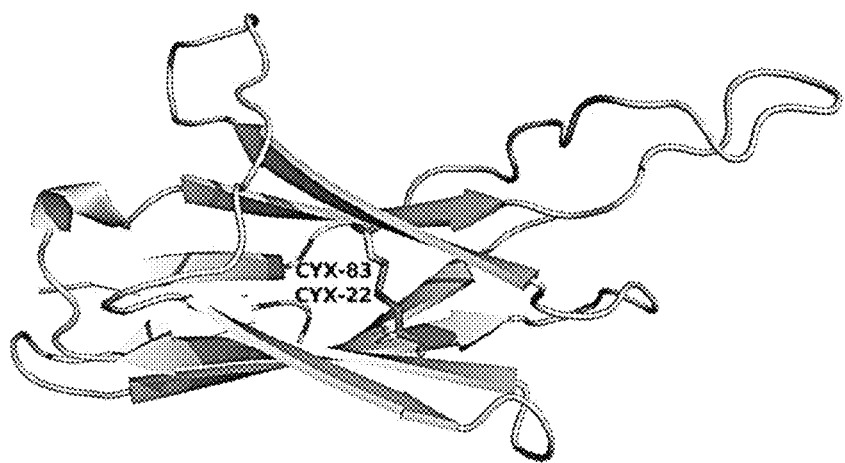
FIG. 42: Disulfide bridges of vNAR V19.

It is a monomer consisting of two groups of beta sheets, with a single disulfide bridge bonding the two groups of sheets; this implies two cysteines (22-83) (FIG. 42).

```
>v19|PDBID|CHAIN|SEQUENCE (SEQ. ID. NO. 8):
  1    AWVEQTPRTATKETGESLTINXVLRDASFELKDTGWYRTKLGSTNEQSISIGGRYVETVN
 61    KGSKSFSLRISDLRVEDSGTYKXQAFYSLPLGDYNYSLLFRGEKGAGTVLIVK
```

During optimization of codons for production in E. coli, differences in the underlined amino acids between the sequences SEQ. ID. NO. 4 and SEQ: ID: NO: 8 were obtained. This does not alter its structure; the proven sequence in subsequent trials has been the SEQ. ID. NO. 4; therefore, this is the preferred embodiment for industrial scaling of V19.

vNAR V32R

Figure 43:
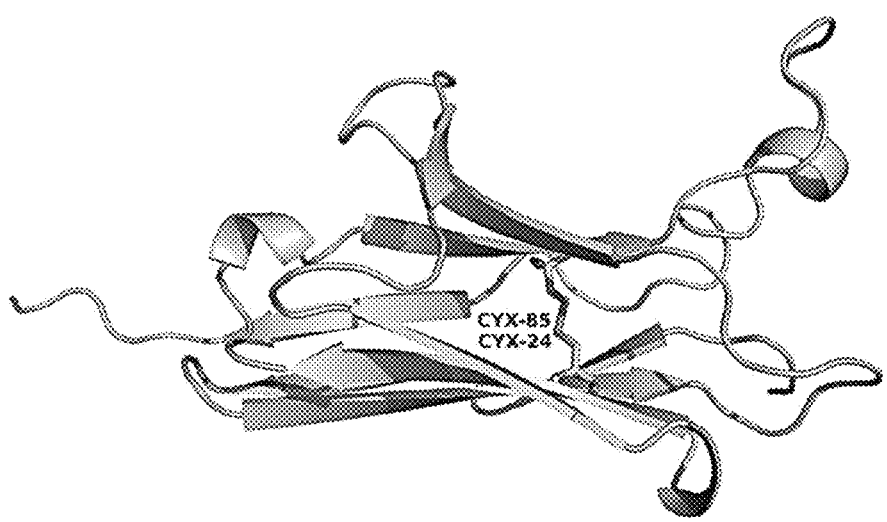
FIG. 43: Disulfide bridges of vNAR V32R.

It is a monomer consisting of two groups of beta sheets, with a single disulfide bridge bonding the two groups of sheets; this implies two cysteines (24-85) (FIG. 43).

```
>V32R|PDBID|CHAIN|SEQUENCE (SEQ. ID. NO. 9):
  1    MAASLDQTPRTATRETGESLTINXVFTDSSCGLCGTSWFRNNPGSTDWERITIGGRYVES

61    VNKGAKSFSLQIKDLTVEDSVTYYXKAQGHRYFSKVCELRCPSYYYDGAGTVLTVNGQAG

121    Q
```

It should be noted that the last 5 underlined amino acids in SEQ. ID. NO. 9 are those that precede the histidine-tag and removed in industrial production so the preferred embodiment of V32R corresponds to SEQ. ID. NO. 6.

Complementarity Determining Regions (CDRS)

Figure 44:
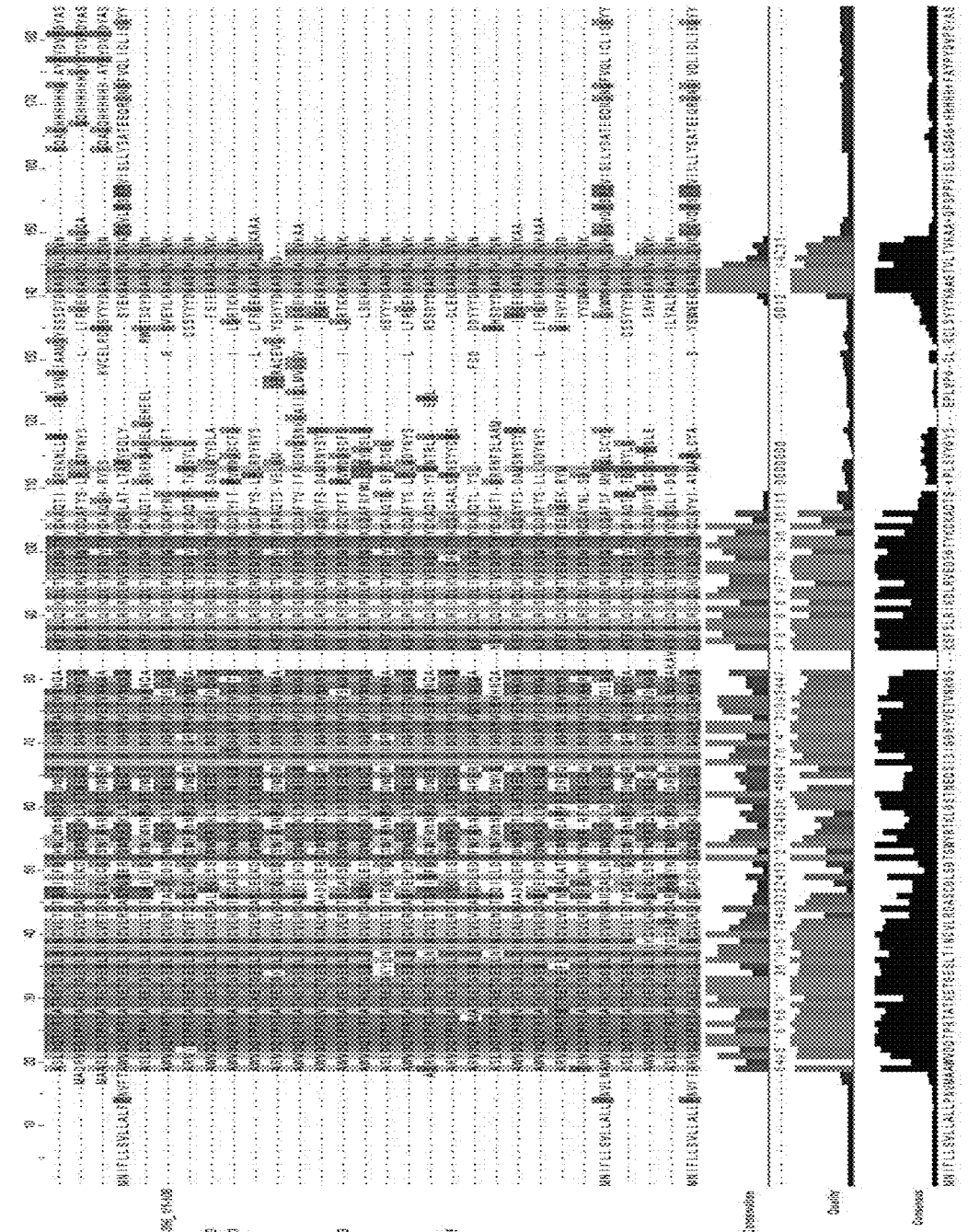
FIG. 44: Multiple sequence alignment.

From the sequences of the antibodies, a search was performed using a local BLAST server (English acronym for Basic Local Alignment Search Tool) using the non-redundant database nr. Those sequences with at least 70% identity to any of the antibodies were recovered. Subsequently, a multiple alignment of the sequences obtained by BLAST and those of the antibodies was performed. For this purpose the software MAFFT (English acronym for Multiple Alignment using Fast Fourier Transform) was used. In this multiple alignment, it is observed which are the invariant and variable regions (related to the CDRs) of this type of antibodies. As it can be seen in FIG. 44, there are clearly conserved regions, other semi-preserved (there are variations in the total set of sequences, but the amino acids are conserved at the subset level, suggesting an evolutionary origin of these variations) and finally variable regions, which are those that provide specificity.

You can see 2 clearly differentiated CDRs:
CDR 1: between positions 45 and 51
CDR 2: between positions 105 and 139

These positions refer to the global numbering provided by the multiple alignments for the set of sequences.

Figure 45:
FIG. 45: CDRs representation (in magenta) of V19 (yellow) bound to VEGF (green).
Figure 46A:
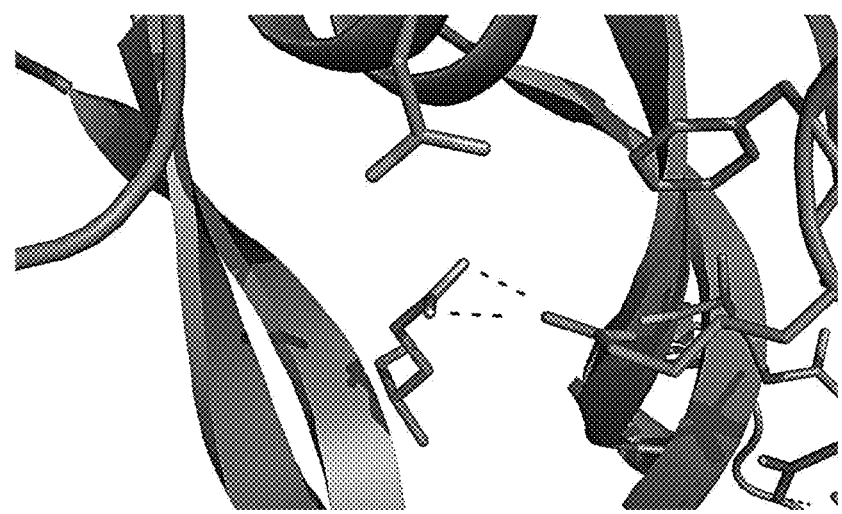
FIG. 46: More important interactions from the area of CDRs of V19 with VEGF. a) ARG101 of V19 with GLU17 of VEGF. b) GLU103 with ARG10.
Figure 46B:
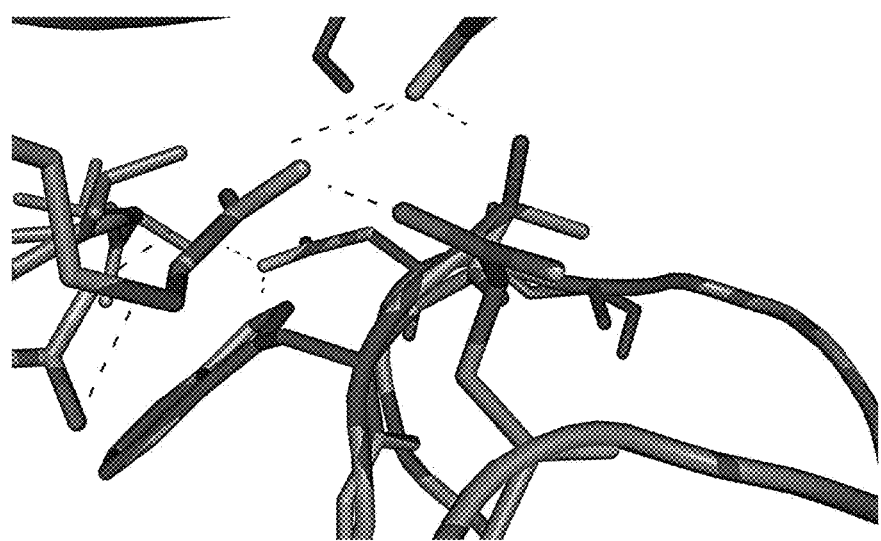
Figure 47:
FIG. 47: CDRs representation (in magenta) of V32R (yellow) bound to VEGF (green).
Figure 48A:
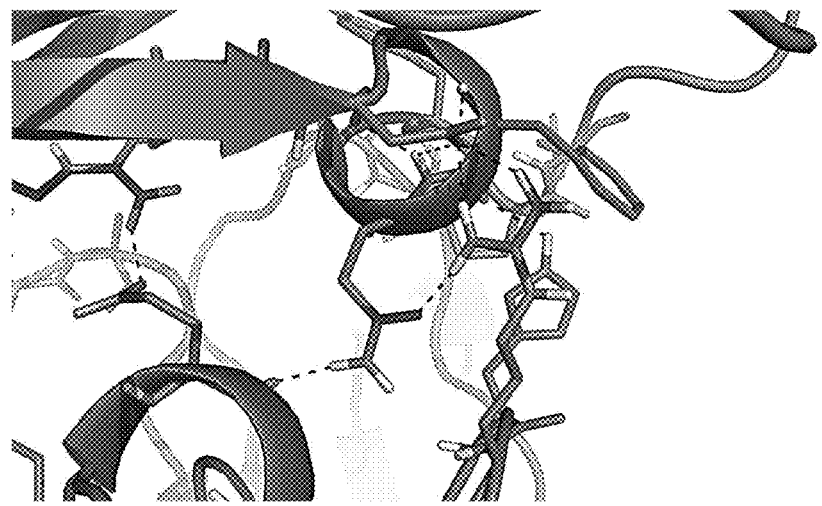
FIG. 48: More important interactions from the area of CDRs of V32R with VEGF. a) GLU98 of V32R with ARG43 and GLN24 of VEGF; ARG91 with GLN24 and ASP21; HIS90 with PHE23; ARG91 with ASP21. b) LYS95 of V32R with GLU25 of VEGF; ARG100 with GLU54; TYR104 with CYS55.
Figure 48B:

In FIGS. 45 and 47 an overview of the area of CDRs pertaining to V19 and V32R is shown. Details of some of the most important interactions from the area of CDRs with VEGF are shown in FIGS. 46a, 46b and 48a, 48b.

Anti-Angiogenic Activity in an In Vitro Model

The activity of the vNAR antibodies: V13 (previously described in the U.S. Pat. No. 8,496,933), V19 and V32R were assessed by an in vitro anti-angiogenic assay using the CellPlayer® angiogenesis kit. The aim of this study was to determine whether the V13, V19 and V32R antibodies were able to inhibit the formation of blood vessels (angiogenesis) and their differences, analyzing the formation parameters and the branching of tubes, taking as reference a commercial antibody (Genentech/Roche) as described in example 10.

Figure 52A:
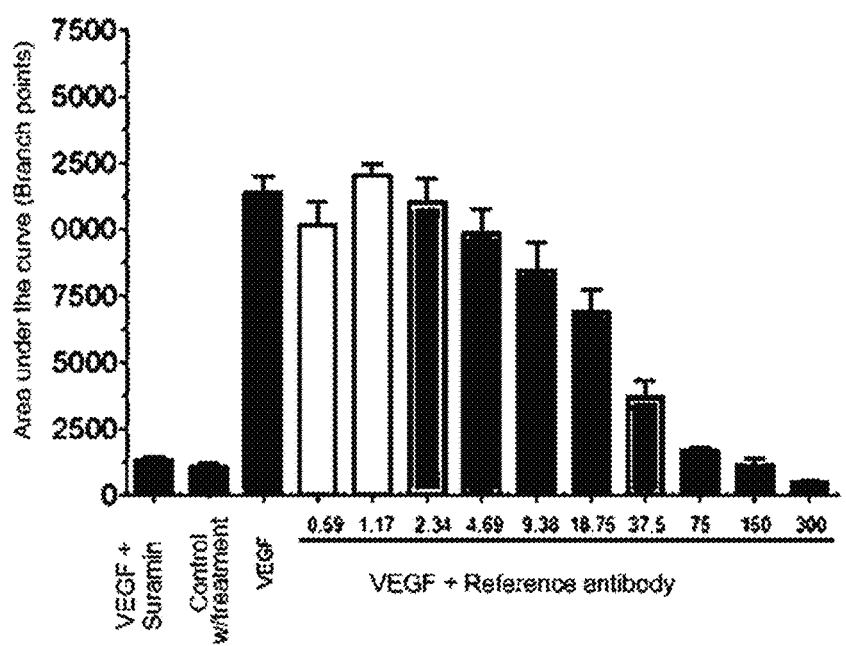
FIG. 52: Histograms represent the mean plus the standard deviation of the area under the curve of the analysis of branching points in presence of antibodies used: (A) Reference antibody*; (B) V13**; (C) V32R; (D): V19. *Ranibizumab (Genentech/Roche). **Clone in the referred patent U.S. Pat. No. 8,496,933.
Figure 52D:
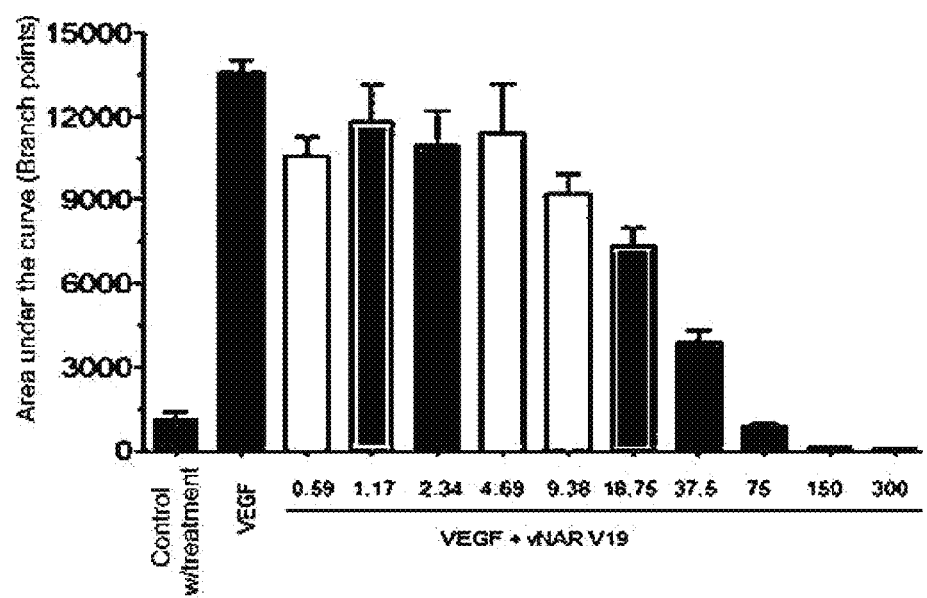
Figure 53:
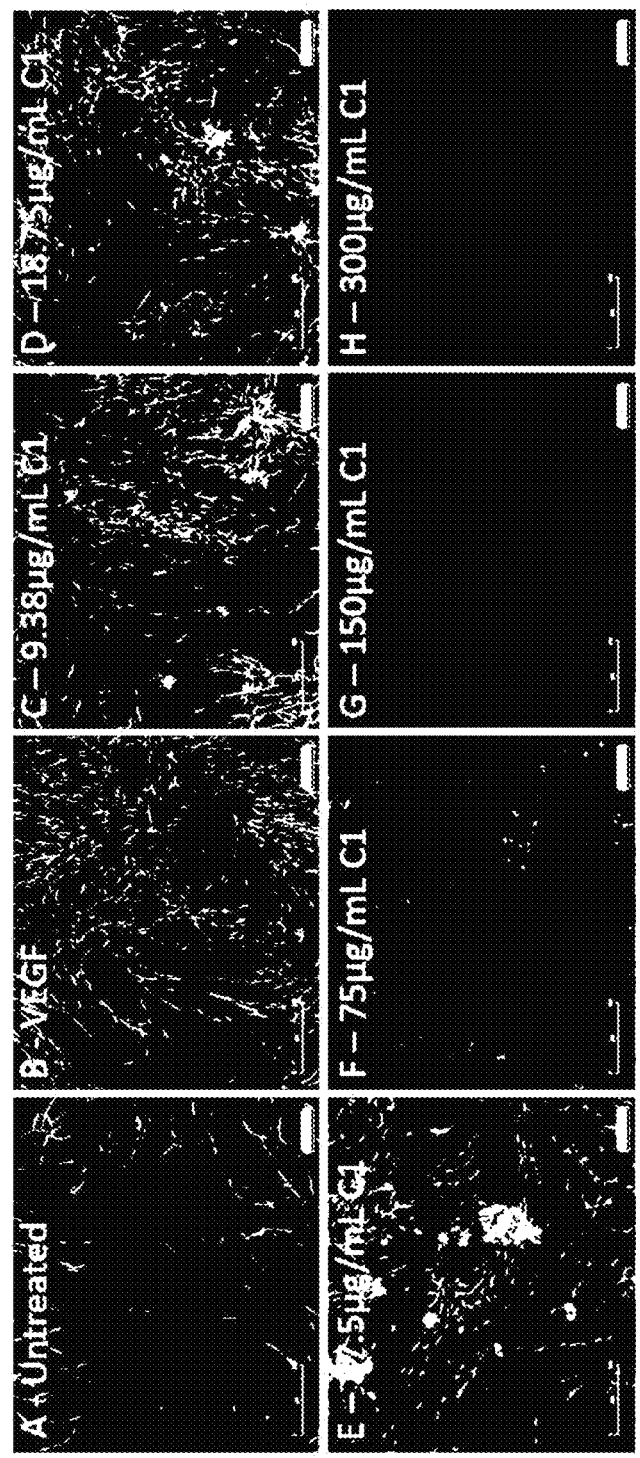
FIG. 53: Representative images of the effect of VEGF and the vNAR V32R antibody in the networking formation.

From this study we were able to conclude that vNAR V13 (previously described in the U.S. Pat. No. 8,496,933), V19 and V32R antibodies are capable of inhibiting the vascularization process mediated by the VEGF cytokine, with a similar kinetics behavior to that of the commercial antibody (Genentech/Roche) (FIG. 50-52). In all cases, an antibody concentration-dependent angiogenic inhibition effect is observed. Inhibition values ($IC_{50}$) considering the two parameters (Table 6) show that both V19 and V32R require up to 12 times less concentration of antibody to produce an inhibitory effect on angiogenesis with respect to the antibody V13 (previously described in the U.S. Pat. No. 8,496, 933) and concentrations similar to those of the commercial reference antibody (Genentech/Roche).

Embodiments of the Invention

The aim of the invention is to provide anti-VEGF molecules useful for treating or preventing diabetic retinopathy, neovascular glaucoma or wet age-related macular degeneration as well as ocular conditions where the phenomenon of VEGF-mediated neovascularization is involved, and whose active component is constituted by vNAR proteins isolated and purified and characterized by their specific amino acid sequence, their tertiary structure, and their significantly increased affinity, neutralizing and recognition capacity of VEGF. Such vNAR recombinant proteins are here referred as V13, V19 and V32R; and their amino acid sequences are defined as SEQ. ID. NO: 2, SEQ. ID. NO: 4 and SEQ. ID. NO: 6 respectively, which by themselves are embodiments of the invention.

Non-limiting embodiments of the invention are the use of vNAR V32R and V19 proteins for ocular administration which contribute to treatment or prevention of pathological processes where neovascularization phenomenon is involved and may be any of the following: Retinal Neovascularization, Choroidal Neovascularization, Corneal Neovascularization, Macular Degeneration, Age-Related Macular Degeneration, Retinal Diseases, Diabetic Retinopathy, Vitreous Hemorrhage, Retinal Hemorrhage, Choroiditis, Retinal Detachment, Retinal Drusen, Neovascular Glaucoma, Choroid Diseases, Uveitis, Myopia, Eye Diseases, Fungal Eye Infections, Telangiectasia, Retinal Artery Occlusion, Degenerative Myopia, Retinal Vein Occlusion, Chorioretinitis, Histoplasmosis, Uveal Diseases, Rubella (German Measles), Ocular Toxoplasmosis, Epiretinal Membrane, Coloboma, Choroid Neoplasms, Retinal Degeneration, Retinitis, Retinal Perforations, Herpetic Keratitis, Retinopathy of Prematurity, Cystoid Macular Edema, Papilledema, Uveomeningoencephalitic Syndrome, Optic Disk Drusen, Angioid Streaks, Retinitis Pigmentosa, Vision Disorders, Sympathetic Ophthalmia, Scar, Ocular Burns, Recurrent Ischemia, Eye Injuries, Glaucoma, Eye Hemorrhage, Scotoma, Posterior Uveitis, Fungemia, Retinal Neoplasms, Corneal Diseases, Pigmentary Incontinence, Hemoglobin C Disease, Fibrosis, Opacity of the Cornea, Anterior Uveitis, Hyphema, Sarcoidosis, Aphakia, Iatrogenic Disease, Panuveitis, Eye Cataract, Postoperative Complications, Sickle Cell Anemia, Retinal Vasculitis, Osteoma, Cytomegalovirus Retinitis, Atrophy, Phlebitis, Keratoconus, Sturge-Weber Syndrome, Viral Eye Infections, Eye Abnormalities, Substance-Related Disorders, Penetrating Eye Injuries, Diabetes Mellitus Type 2, Radiation Injuries, Sickle Cell Trait, Pseudophakia, Pigmented Nevus, Proliferative Vitreoretinopathy, Bleeding, Diabetes Mellitus Type 1, Nevus, Optic Nerve Diseases, Vascular Diseases, Candidiasis, Chemical Burns, Microphthalmia.

Another embodiment of the invention relates to each of the bacterial clones expressing these vNAR for industrial scale production, including clones of *E. coli* named VEG-FvNAR v32R and VEGFvNAR v19, which express the vNAR: V32R and V19.

Another embodiment of the invention relates to plasmid vectors encoding the vNAR V32R and V19, which are characterized by comprising the coding sequences thereof including the vectors described herein.

Embodiments of the invention include the use of vNAR V32R and V19 proteins for the preparation of medicaments for the prevention or treatment of diseases where the neutralization of VEGF activity is required, and wherein the drugs may be for ophthalmic use.

Embodiments of the invention are the ophthalmic pharmaceutical compositions characterized by containing a pharmaceutically correct dose of vNAR proteins of the invention as active ingredient and they are characterized in that the base composition or carrier provides the necessary stability and conservation to these proteins.

The following examples are presented to substantiate the performance of the biopharmaceuticals described herein; these examples are illustrative and non-limitative of the scope of the invention.

EXAMPLES

Example 1: Production of the Immune Library and Selection of vNAR Clones Specific for VEGF The immunization of the shark specimen is the first step continuing an immunization protocol of 20 weeks with 1 μg of protein in PBS, by intravenous administration of human recombinant cytokine $VEGF_{165}$. The first two immunizations also included the complete form of Freund's adjuvant; the challenges were performed every 15 days, during the same period. Before each reinforcement we carried out 1 mL phlebotomies from caudal vein; this serum was stored at −20° C.

Next step was total RNA extraction, from spleen of specimens, which was dissected 7 days after the last immunization, following standard protocols of phenol-chloroform RNA extraction, and precipitation from isopropanol, resulting 1.2 μg/μL of total RNA; purity was tested by means of spectrophotometry. Afterwards, retrotranscription (RT-PCR) with conventional methods was performed, using the antisense oligonucleotide GTTCACAGTCAGCACGGTGCCAGCTC (SEQ. ID. NO. 10) at initial concentration of 20 μM, and 1 μg of total RNA. From the fragment of approximately 620 bp, visualized through a 2% agarose gel, dying it with ethidium bromide, the PCR reaction was carried out to obtain the two DNA strands.

To obtain the double strand of DNA we also used a mixture of the following sense 7 oligonucleotides:

GCACGGCTTGAACAAACACC, (SEQ. ID. NO. 11)

CAACGGGTTGAACAAACACC, (SEQ. ID. NO. 12)

ACAAGGGTAGACCAAACACC, (SEQ. ID. NO. 13)

GCAAGGGTGGACCAAACACC, (SEQ. ID. NO. 14)

GCATGGGTAGACCAAACACC, (SEQ. ID. NO. 15)

GCAAGCCTGGACCAAACACC, (SEQ. ID. NO. 16)

GCATTGACGGACCAAACACC. (SEQ. ID. NO. 17)

Both sense and antisense oligonucleotides have an additional sequence, conferring on them a recognition site for the restriction enzyme SfiI. The amplified fragments were analyzed by means of an electrophoresis on 2% agarose gel and ethidium bromide at final concentration of 50 ng/μL, (30 minutes at 100 Volts). The fragment size corresponding to the expected size according to used oligonucleotide set, (from about 320-350 bp were cut from the gel). Subsequently, using a special kit the DNA was extracted from gel. This process was repeated until a sufficient quantity of DNA was obtained.

Then, 1.5 g of purified DNA fragment was digested, obtained by means of PCR, corresponding to the vNAR genes with 5U of the restriction enzyme SfiI per μg of DNA to be digested, incubating 5 hours at 50° C. The mixture was inactivated and stored at −80° C.

The following step was preparing the cloning vector, the phagemid expression vector pCOMb3X, which possesses two cut sites for the SfiI enzyme, so that cloned vNAR are expressed on phages (phague display). Digestion products were purified on a 1% agarose gel, recovering the restricted vector and obtaining two fragments, one of approximately 3500 bp, and another one of approximately 1500 bp.

The first fragment corresponds to digested vector in both digestion sites, and the second to resultant staffer fragment. They were visualized on 1% agarose gel and both bands were cut, followed by DNA extraction through triturationfreezing. They were purified and quantified by means of a spectrophotometer at 260 nm.

After that, we proceed to perform ligation of $V_HNAR$ fragments and pCOMb3X vector, on a small-scale, to verify all conditions of the digested fragments, and then perform it on a large-scale. Ligation was done between vNAR insert and pCOMb3X vector previously digested, in a 1:1 molar ratio using the enzyme T4 DNA ligase. The positive control of ligation comprised the digested vector plus the stuffer fragment produced by digestion in both cut sites. Negative control of digested vector without stuffer fragment, with and without T4 ligase, was used to verify that the vector was not ligated on itself. Also, a control with a digested vector and without enzyme T4 ligase was made, confirming that the vector is well digested. The efficiency of ligation was verified by electroporation in electrocompetent cells *E. coli* ER2537 (200 Ohms, 2.5 kV, 4 ms) following the standard methodology, including at the end the seeding of electroporated *E. coli* on plates of LB agar in 3 serial dilutions, and colony-forming units were obtained (CFU). The size of the libraries was calculated considering the number of CFU and the ligation, culture and seeding volumes.

The size of the immune library obtained for $VEGF_{165}$ is $6.36 \times 10^8$ CFU/mL, (on large-scale), that can be considered representative of variability generated by the shark after immunization protocol. In negative controls, there was no growth on LB agar plates containing ampicilin (20 μg/mL final concentration). The primary library amplification was performed by cultivating electroporated cells, the helper phage VCSM13 was used following conventional methodology cultivating overnight in SB medium containing ampilicilin and kanamycin, then they were centrifuged for obtaining and storage of supernatant previously sterilized by filtration. After primary library amplification, four selection rounds of the obtained phage-antibodies were performed, using VEGF (1 µg in PBS) on an ELISA plate (previously incubated and blocked with BSA 3% in PBS), therefore 5 g/mL of cytokine VEGF and 50 µL of 3% BSA were put into contact per well (per duplicate), used as the antigen in negative controls. Thus, the cytokine remained immobilized inside the plate wells. 50 µL of phages were incubated at 37° C. for 1 hour; 5, 10, 15 and 20 astringent washes were performed for each one of the 4 rounds (respectively), using Tween 0.05%-PBS 1× per well; with this procedure, we expect that selected phages will be more specific to the VEGF antigen. Subsequently resulting fagos from rounds 3 and 4 were used, this time in cultures of E. coli TOP10F'; the presence of the insert was verified through PCR, and then expression induction of the vNAR protein was carried out, subsequently this was extracted from periplasmic fraction of E. coli by means of osmotic shock, and they were purified by means of affinity chromatography to nickel; ELISA was carried out to determine the expected affinity to VEGF. Yields of the whole process were not the best, this could be due to inclusion bodies formation containing aggregates of insoluble or not active proteins; they cannot be extracted by performing periplasmic extraction, or because ELISA is not able to detect those production levels.

Example 2: Preparation of Expressing Cells of Anti-VEGF vNAR BL21 (DE3), Subsequent Treatment and Characterization of vNAR Recognition Ability Through ELISA To determine the expression and the specific recognition of the products from selected clones, for VEGF as their target molecule, 50 mL of culture of BL21(DE3) cells were induced, modified by plasmids pET-20b(+) (without signal peptide) and pET-28a(+) (with signal peptide) containing separately V13, V19 and a V32R. The obtained clones were individualized and positive clones were confirmed by means of colony-PCR, and through electrophoresis analysis on agarose gel. Saturated cultures from positive clones were prepared in selective LB liquid medium also containing ampicilin (clones in pET20b+) or kanamycin (clones in pET28a+), and from these we obtained stocks in 15% glycerol to preserve them at −80° C. We studied overexpression of the protein of interest by SDS-PAGE and through immunoblotting (Western-Blot), using anti-His or anti-HA antibodies plus secondary antibodies conjugated to peroxidase, and revealed with a specific substrate 7 MB.

On the other hand, we proceeded to evaluate protein expression at small-scale (pilot trials), and then at large-scale from positive resulting clones, initiating with cultures of transformed (positive) BL21 (DE3) bacteria, in LB medium containing antibiotic at 37° C. of temperature until optical density (0.6-0.8) was achieved, which we considered optimum in pilot trials. The expression inductor IPTG at 0.8 mM was added, and expression at optimum conditions of temperature (30° C.), and time (20-22 hours) was maintained. We proceeded to purify from cell pellets obtained from those cultures, from its lysis by means of buffers and sonication, and subsequently we separated the inclusion bodies from the insoluble fraction; purification included carrying out an affinity chromatography by immobilized metals, the corresponding resin has affinity to proteins fused with 6×His. Once the protein was solubilized, we proceeded to perform the folding by means of the above-mentioned method On-column.

To validate vNAR protein functionality, obtained through this procedure, indirect ELISA assays, immunoblotting and flow cytometry were performed.

To perform ELISA tests we upholster plates with 50 µL, 300 ng/well of rhVEGF antigen (recombinant human vascular endothelial factor, version 165) produced in laboratory, and also we use the commercial equivalent antigen (Recombinant Human VEGF165 of Peprotech®). The upholstery was performed with identical results 2 hr/37° C. or 12-16 hours at 4° C. As a negative control antigen of the assay, the bovine serum albumin (BSA) was used and even wells without antigen. Following adsorption, the wells were blocked (16 h at 4° C. or 2 hours at room temperature) with 150 µl PBS-5% skim milk, and the plates were washed with PBS-Tween 0.05%; then, 150-50 µl of diluted vNAR preparation in PBS-5% skim milk were added to the wells (the quantities of added vNAR per well ranged between 0.1 and 15 µg) and incubated for 2 hours at room temperature. After four washes with PBS-Tween, the vNAR antibodies retained in the wells were detected with a secondary antibody to detect the tag fused to the vNAR: 6His or HA. A monoclonal antibody against the histidine tag (Anti 6His) or an anti-HA polyclonal antiserum was used at dilutions between 1:3000 and 1:1000 (50 µl per well) diluted in PBS-5% skim milk. The plates were incubated and washed and the antibody for revealed conjugated to peroxidase (50 µl per well) was added: either goat anti-rabbit IgG antiserum in the wells with the polyclonal anti-HA or rabbit anti-mouse IgG antiserum in wells with the monoclonal anti6His. The plates were incubated for 30-45 minutes at room temperature, washed extensively with PBS-Tween, 100 µl of TMB being added to the wells, substrate of the peroxidase. After a short incubation, the reaction was stopped by adding 50 µl of 3 N $H_2SO_4$ to the wells. The optical density of the oxidized o-phenylenediamine (OPD) was measured ($\lambda$=450 nm) in a Multiscan Plus (Flow) spectrophotometer.

A commercial anti-VEGF monoclonal antibody that recognizes human VEGF165 isoform (Anti-VEGF monoclonal of mouse from Abcam, reference ab1316) at 1:1000 dilution and the one conjugated to peroxidase rabbit anti-mouse IgG antiserum were used as positive control.

FIG. 13 shows the result of the ELISA assay, where increased protein expression by clones V32R and V13 is obvious over clone V19.

Example 3: Isolation of Subcellular Fractions

The standard procedure of these tests starts with 500 ml of bacterial culture by inducing with IPTG (0.8 mM final concentration) at 30° C. or 37° C. for 16-20 hours. The culture is then processed by centrifugal separation of the cells and the culture medium. The cells are either treated with mild osmotic shock mediated by sucrose to obtain the extracellular medium, the proteins from the periplasm; or lysed with lysozyme, detergent and sonication to extract from them the soluble and insoluble intracellular components separated by centrifugation. The evaluation of each fraction was performed essentially by studying overexpression of the protein of interest in SDS-PAGE, followed by Coomassie blue staining and by specific detection thereof by serological methods, specifically Western-Blot using anti "tag" monoclonal antibodies (anti-His or anti-HA) and secondary antibodies conjugated to peroxidase.

Example 4: Determination of the Amino Acid Sequences of the Anti-VEGF vNAR

The purified proteins of the reactive clones were processed to obtain the sequence in the laboratory (Seqxcel Laboratory, San Diego, Calif., EEUU) the mixture was prepared according to the suggested conditions using the primer Ompseq, due to pCOMb3X vector has the complementary sequence for this oligonucleotide, the specific sequences for VEGF were obtained with the Mac Vector 7.2.2 software; these are included in the sequence listing, which are: SEQ. ID NO: 3, SEQ. ID NO: 4 (for clone V19) and SEQ. ID NO: 5 and SEQ. ID NO: 6 (for clone V32R).

Example 5: Refolding In Situ: On Column Refolding

The cytoplasmic fraction of the protein of interest is found mostly forming inclusion bodies, readily isolated after bacterial lysis by centrifugation of the extracts. The protein of interest is recovered by an original purification method of GE Healthcare$^{MR}$ called On-Column Refolding, which requires having the solubilized proteins. Therefore, it was necessary to employ guanidine chloride in those fractions where proteins formed inclusion bodies.

To carry out the On-Column Refolding process, we first proceeded to the preparation of buffers, all at pH 8.0. After we added 100 mM L-Arg: Binding buffer (port A1): Based on 6 M guanidine hydrochloride, solubilization buffer (port A2): Based on 6M urea, and elution buffers (port A3) and Refolding buffer (port B): both containing Tris-HCl NaCl, imidazole, and 2-mercaptoethanol. All contain imidazole, which in the binding buffer operates to reduce nonspecific binding of proteins, that is, those lacking the histidine tails, and also participates in the elution thereof.

We proceeded to prepare the sample (protein previously solubilized with guanidine chloride) by adjusting it to the composition of the binding buffer, diluting or resuspending the inclusion bodies in binding buffer overnight at vortexing.

We continue the preparation of the system and chromatography: After mounting the AKTA-prime equipment and the selected column (His Trap 1 ml FF crude, GE Healthcare), the Application Template, On-column Refolding His Trap method was selected in the system. The exchange of buffers or buffers in the columns was performed. The sample was filtered through 0.45 microns before performing the chromatography.

Figure 49:
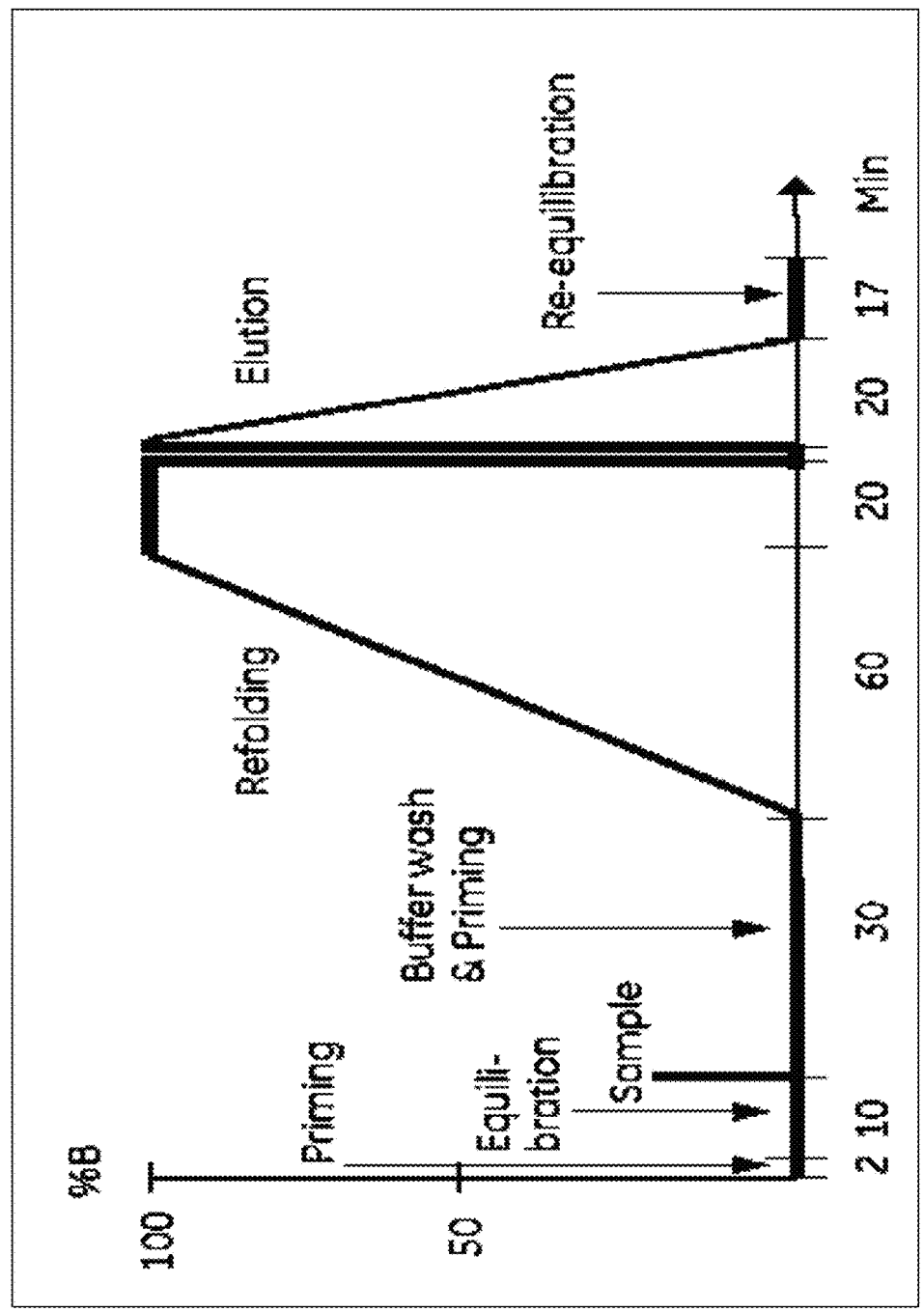
FIG. 49: Theoretical gradient of in situ refolding (On-column refolding) HisTrap application template. Total separation time=160 min+application time of the sample.
Figure 51A:
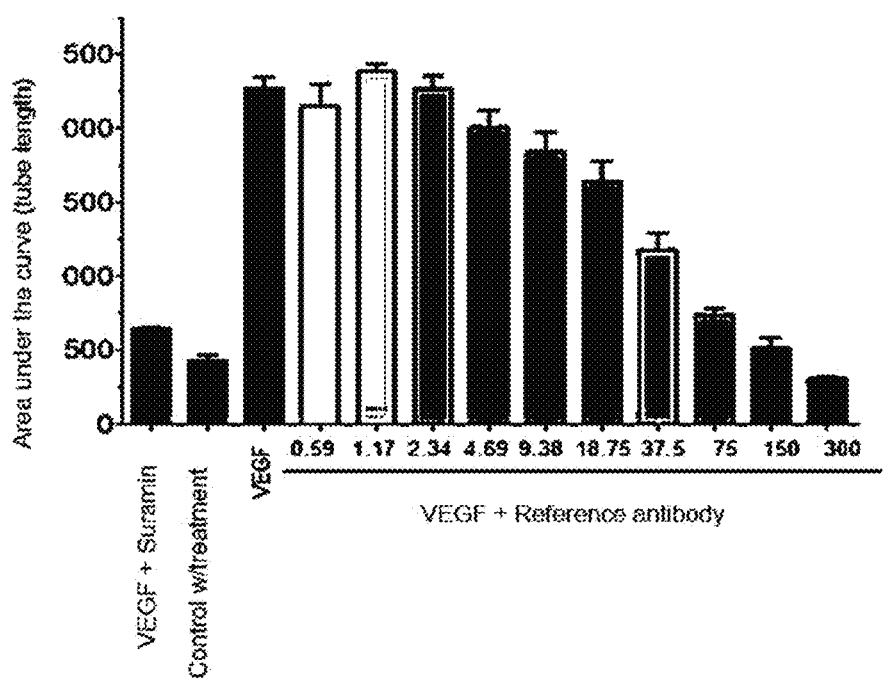
FIG. 51: Histograms represent the mean plus the standard deviation of the area under the curve of the tube length analysis in presence of antibodies used: (A) Reference antibody*; (B) V13**; (C) V32R; (D): V19. *Ranibizumab (Genentech/Roche). **Clone in the referred patent U.S. Pat. No. 8,496,933.
Figure 51B:
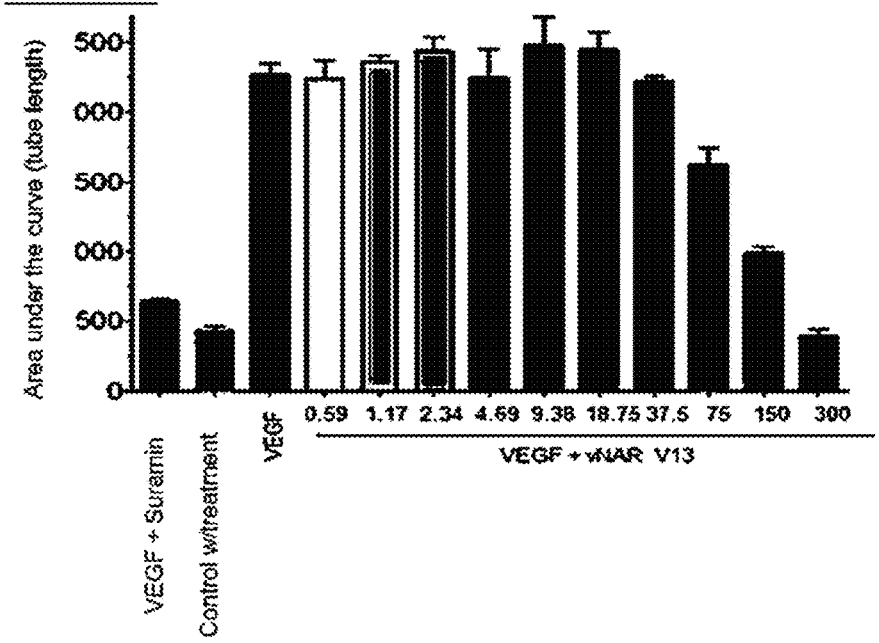
Figure 51C:
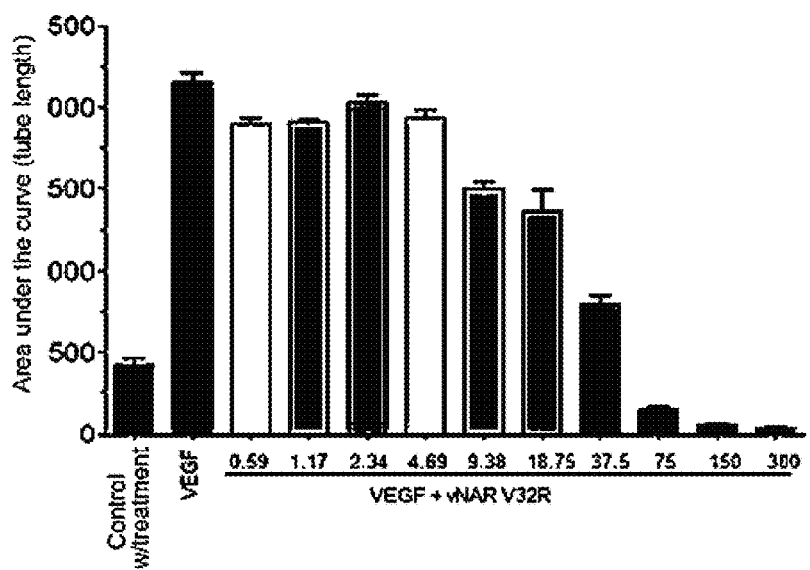
Figure 51D:
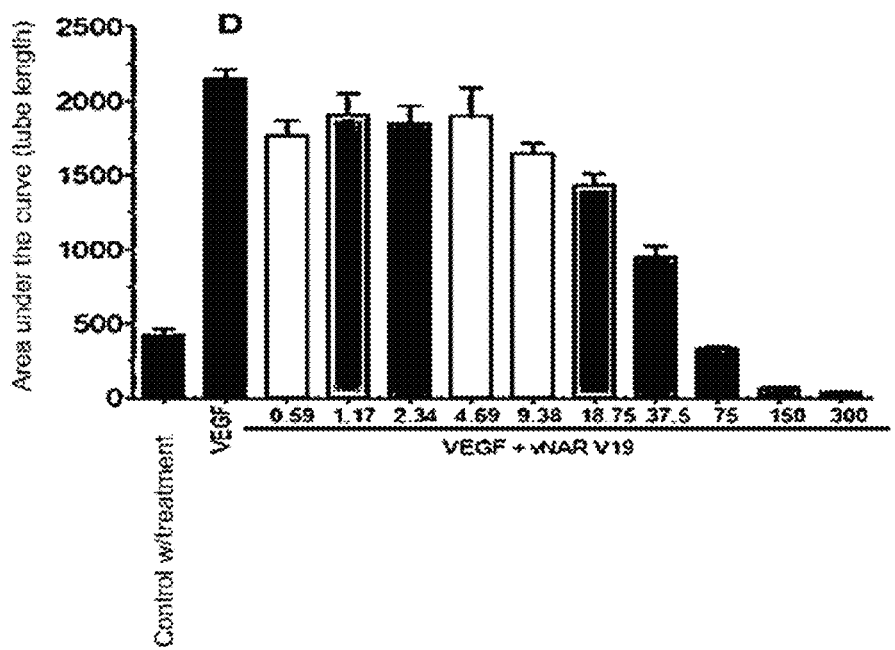

FIG. 49 shows a diagram of the gradient applied by the selected method with the refolding buffer, the different stages of the process and the runtime. The fractions containing the eluted proteins are detected by their absorbance at 280 nm.

Example 6: Flow Cytometry

U937 cells were used as model cells to analyze the reactivity of the vNAR antibodies with VEGF. Some 1,000,000 cells, previously fixed and permeabilized, were incubated with the selected vNAR antibody for 30 min at room temperature at different dilutions according to the preparation and specific activity of the vNAR. After several washes with PBS pH 7.4, the cells were incubated with anti-6×His monoclonal antibody, followed by appropriate washing and incubation with an antibody conjugated to Alexa Fluor 488. After labeling, the cells were washed with PBS and finally resuspended in a volume of 250 µl of PBS. The fluorescently labeled cells were quantified with a flow cytometer. The commercial anti-VEGF monoclonal antibody and the same conjugated secondary antibody were used as positive control. The cells were identified in a "dot plot" by their size (forward scatter or FSC: "forward-angle light scatter") and complexity (side scatter, or SSC: "side-angle light scatter"). The emission of the fluorochrome Alexa Fluor 488 was collected in the FL1 detector. The amplifier detector of the fluorescence intensity was adjusted between $10^0$-$10^1$ with U937 cells, non-treated with primary vNAR antibody (negative control).

Example 7: Thermal Stability

Different aliquots of the vNAR were prepared and incubated at different temperatures for several days (between 3 and 7 days) to assess their short-term thermal stability. Typically, the studied temperatures were: 37° C. (1 hour), RT, 4° C., 0° C., −20° C. and −80° C. Freezing at −20° C. and −80° C. was fast and it was performed in an ethanol-dry ice bath. After the incubation period the samples were subjected to centrifugation to discard the aggregates produced in that time. The frozen samples at −20° C. and −80° C. were thawed on ice prior to centrifugation. A denaturing 15% SDS-PAGE was carried out with the supernatant of these samples. After staining with Coomassie blue, the loss of soluble protein was analyzed by the formation of aggregates in the different incubations.

Example 8: Mass Spectrometry

For the identity analysis by mass spectrometry, the vNAR preparations were subjected to denaturing 15% SDS-PAGE. After staining with Coomassie blue, the vNAR band was cut from the gel and analyzed by MALDI-TOF-TOF mass spectrometry. This system can identify proteins by determining the exact masses of peptides formed by enzymatic digestion. Furthermore, the system can more accurately identify and characterize proteins by tandem time-of-flight (TOF/TOF), a technology to isolate and fragment a molecular ion of interest and obtaining the measurement of ion masses of protein fragments. The gel pieces were washed with 50% acetonitrile. Then, the gel pieces were placed at 56° C. for 45 min in 10 mM DTT, 55 mM iodoacetamide in 25 mM ammonium bicarbonate in darkness. Ammonium bicarbonate was added to the gel fragment trypsin, and it was incubated overnight at 37° C. It was then transferred to 50% acetonitrile, 0.1% trifluoroacetic acid, and the peptides of the gel piece were extracted by sonication for 5 min. The peptides were resuspended in 10 µL of 33% acetonitrile, 0.1% trifluoroacetic acid. For analysis of MALDI-TOF-TOF mass spectrometry, an ABi 4800 MALDI TOF/TOF™ spectrometer was used, in the positive ion reflector mode. The ion accelerating voltage was 20 kV. For identification of mass fingerprinting in peptides, mass maps of trypsinized peptides are transferred through the Bio Tools™ MS (Bruker Daltonics) program to search Swiss-Prot using the Mascot (Matrix Science) software.

Example 9: Endotoxin Removing

For removing endotoxins in the vNAR preparations, two tools were used: Detoxi-Gel Endotoxin Removing Columns: columns using polymyxin B immobilized on a matrix to bind and remove pyrogens present in solutions. This chromatographic approach is simple to use and offers quick removal of small volume samples. Different vNAR samples were used for these columns with good results. Fractions collected after charging and elute the vNAR sample in these columns were analyzed by denaturing SDS-PAGE. Those in which the protein is present, are joined and again quantified by electrophoresis. Overall, vNAR preparations tolerate this treatment and the obtained protein yields are mostly between 75-90% of recovered protein.

Example 10: Comparative Study of the Inhibition of Angiogenesis In Vitro

The assay consisted of cultures in a 96-well plate of endothelial cells from human umbilical vein (HUVEC) transfected with the green fluorescent protein in coculture with human fibroblasts (NHDF) for 14 days. As a positive control, 4 ng/mL VEGF were used, which produced an extensive tube formation and networking on all plates, reaching levels of tube length about 13-14 mm/mm$^2$.

As first negative control, cultures are maintained in the absence of VEGF, which does not favor tube formation, reaching levels of only 2-3 mm/mm$^2$. Another applied negative control is achieved by the addition of 100 µM suramin; this treatment completely inhibited VEGF-mediated angiogenesis.

Different concentrations of the vNAR antibodies are added to the wells on days 4, 5, 7, 10 and 12 of the experiment: V13 (previously described in the U.S. Pat. No. 8,496,933), V19 and V32R, as well as the reference antibody (Genentech/Roche) under the presence of 4 ng/ml VEGF (see FIG. 50). Each plate is used to analyze two compounds. Thus, quadruplicates by concentration are available. Six images were taken per well at the end of each treatment.

Two parameters of the vascularization process were measured after exposure to the compounds for 14 days: the length of the tubes (FIG. 51) and the branching points (FIG. 52). The results from the measurement of these parameters were compared with cells that only received 4 ng/mL VEGF (positive control), and 20 µM suramin+VEGF (negative control).

The analysis shows that VEGF stimulates tube formation and branch points in comparison with controls, and that the reference antibody (Genentech/Roche) (A), V13 (B), V32R (C) and V19 (D) inhibit tube formation and also inhibit the formation of branching points in concentration-dependent manner.

The analysis of the concentration, of each antibody, required to inhibit the process of angiogenesis by 50% (IC$_{50}$) in the in vitro assay, was determined by constructing a dose-response curve, using a non-linear regression model. The data obtained are shown in Table 6; the potency of the antibodies is expressed as the concentration (mg/mL) required to neutralize 50% of the angiogenic activity of two parameters: length of tubes and branching points measured in an in vitro assay.

TABLE 6

| | Inhibition values (IC$_{50}$) | | |
| --- | --- | --- | --- |
| Treatment | Length of the tubes (µg/mL) | Branching points (µg/mL) | Average value (µg/mL) |
| Reference antibody (Genentech/Roche) | 57.6 | 37.5 | 47.6 |
| V13 | 436.1 | 340.4 | 388.3 |

TABLE 6-continued

| | Inhibition values (IC$_{50}$) | | |
| --- | --- | --- | --- |
| Treatment | Length of the tubes (µg/mL) | Branching points (µg/mL) | Average value (µg/mL) |
| V32R | 27.6 | 19.3 | 23.4 |
| V19 | 35.8 | 24.7 | 30.2 |

FIGS. 53, 54, 55 and 56 show images representing the angiogenesis inhibition effect from V32R, V19, and V13 antibodies, and the reference antibody.

The main conclusion of this study is that all antibodies show an inhibitory effect of the angiogenesis process measured by the number and branching points of vessels, in a concentration-dependent manner. The concentration of V32R and V19 antibodies that inhibits in 50% is in a range of 20-40 mg/mL.

REFERENCES

1. Nuttall S D, Krishnan U V, Hattarki M, De Gori R, Irving R A, Hudson P J. Isolation of the new antigen receptor from wobbegong sharks, and use as a scaffold for the display of protein loop libraries. Mol Immunol. 2001 August; 38(4):313-26.
2. Dumoulin M, Conrath K, Van Meirhaeghe A, Meersman F, Heremans K, Frenken L G, Muyldermans S, Wyns L, Matagne A. Single-domain antibody fragments with high conformational stability. Protein Science, 2002. 11: 500-515.
3. Flajnik Martin F., Diaz Marilyn, Velez Jovanna, Singh Mallika, Cerny Jan. Mutational pattern of the nurse shark antigen receptor gene (NAR) is similar to that of mammalian Ig genes and to spontaneous mutations in evolution: the translesion synthesis model of somatic hypermutation. International Immunology, 1999. 11(5):825-833.
4. Wesolowski J., Alzogaray V., Reyelt J., Unger M., Juarez K., Urrutia M., Cauerhff A., Danquah W., Rissiek B., Scheuplein F., Schwarz N., Adriouch S., Boyer O., Seman M., Licea A., Serreze D. V., Goldbaum F. A., Haag F., Koch-Nolte F. Single domain antibodies: promising experimental and therapeutic tools in infection and immunity. Med Microbiol Immunol (2009) 198:157-174.
5. Muyldermans, S, and Lauwereys M. Unique single-domain antigen binding fragments derived from naturally occurring camel heavy-chain antibodies. Journal Molecular Recognition, 1999. 12:131-140.
6. Nuttall S D, Krishnan U V, Doughty L, Pearson K, Ryan M T, Hoogenraad N J, Hattarki M, Carmichael J A, Irving R A, Hudson P J. Isolation and characterization of an IgNAR variable domain specific for the human mitochondrial translocase receptor Tom70. Eur. J. Biochem, 2003. 270: 3543-3554.
7. Nuttall S D, Krishnan U V, Doughty L, Nathanielsz A, Ally N, Pike R N, Hudson P J, Kortt A A, Irving R A. A naturally occurring NAR variable domain binds the Kgp protease from Porphyromonas gingivalis. FEBS Lett. 2002, 10; 516(1-3):80-6.
8. Nuttall S D, Humberstone K S, Krishnan U V, Carmichael J A, Doughty L, Hattarki M, Coley A M, Casey J L, Anders R F, Foley M, Irving R A, Hudson P J. Selection and affinity maturation of IgNAR variable domains targeting Plasmodium falciparum AMA1. Proteins. 2004, 1; 55 (1): 187-97.

9. Dooley H, Flajnik M F, Porter A J. Selection and characterization of naturally occurring single-domain (Ig-NAR) antibody fragments from immunized sharks by phage display. Mol. Immunol. 2003 September; 40(1):25-33.
10. Witmer A N, Vrensen G F, Van Noorden C J, Schlingemann R O. Vascular endothelial growth factors and angiogenesis in eye disease. Prog Retin Eye Res. 2003; 22(1): 1-29.
11. Mitchell Paul, Foran Suriya, Wong Tien Y, Chua Brian, Patel Ilesh, Ojaimi Elvis. Guidelines for the Management of Diabetic Retinopathy. Australian Diabetes Society for the Department of Health and Ageing, 2008.
12. Asociación para Evitar la Ceguera en México, A. C. Hospital "Luis Sánchez Bulnes" http://www.apec.org.mx/nosotros/retina.html (Consulta: 12.09.11)
13. Asociación para Evitar la Ceguera en México, A. C. Hospital "Luis Sánchez Bulnes" http://www.apec.org.mx/pacientes/degeneracion_macular.html (Consulta: 12.09.11)
14. OMS (2011) Datos y Cifras: 10 datos sobre la ceguera y la discapacidad visual. http://www.who.int/features/factfiles/blindness/es/index.html (Consulta: 14.10.11)
15. OMS (2011) Temas de Salud: Ceguera http://www.who.int/topics/blindness/es/index.html (Consulta: 14.10.11)
16. Maharaj A: and Dámore P. Roles for VEGF in adult. Microvasc. Res. 2007; 74(2-3): 100-113
17. Hendriksen E. M., Span P. N., Schuuring J., Peters J. P. W., Sweep F. C. G. J, van der Kogel A. J., Bussink J. Angiogenesis, hypoxia and VEGF expression during tumour growth in a human xenograft tumour model. Microvascular Research, 2009; Vol. 77(2): 96-103.
18. Henderson, K. A., Streltsov, V. A., Coley, A. M., Dolezal, O., Hudson, P. J., Batchelor, A. H., Gupta, A., Bai, T., Murphy, V. J., Anders, R. F., Foley, M., Nuttall, S. D. Structure of an IgNAR-AMA1 complex: targeting a conserved hydrophobic cleft broadens malarial strain recognition. Structure 2007, 15: 1452-1466.
19. Streltsov, V. A., Varghese, J. N., Carmichael, J. A., Irving, R. A., Hudson, P. J., Nuttall, S. D. Structural evidence for evolution of shark Ig new antigen receptor variable domain antibodies from a cell-surface receptor. Proc. Natl. Acad. Sci. USA 2004, 101: 12444-12449.
20. Muller, Y. A., Li, B., Christinger, H. W., Wells, J. A., Cunningham, B. C., de Vos, A. M. Vascular endothelial growth factor: crystal structure and functional mapping of the kinase domain receptor binding site. Proc. Natl. Acad. Sci. USA 1997, 94: 7192-7197.
21. Stanfield, R. L., Dooley, H., Verdino, P., Flajnik, M. F., Wilson, I. A. Maturation of shark single-domain (IgNAR) antibodies: evidence for induced-fit binding. J. Mol. Biol. 2007, 367: 358-372.

The invention claimed is:

1. An isolated anti-VEGF vNAR protein selected from the group consisting of V19 comprising the amino acid sequence of SEQ ID NO: 4 and V32R comprising the amino acid sequence of SEQ ID NO: 6, wherein the anti-VEGF vNAR protein recognizes human VEGF and has enhanced affinity for a target molecule VEGF.

2. The anti-VEGF vNAR protein of claim 1, wherein V19 comprises various β sheets connected by loops, with a highly flexible variable region consisting of two β sheets interconnected by a loop and a monomer consisting of two groups of beta sheets with a single disulfide bridge bonding the two groups of sheets, comprising SEQ ID NO: 4.

3. The anti-VEGF vNAR protein of claim 1, wherein V32R comprises β sheets and a monomer consisting of two groups of beta sheets with a single disulfide bridge bonding the two groups of sheets, comprising SEQ ID NO: 6.

4. The isolated anti-VEGF vNAR protein of claim 1, wherein the V19 or the V32R:
a) originates from *Orectolobus maculatus* or *Heterodontus jrancisci*; and
b) binds to and neutralizes the activity of the vascular endothelial growth factor (VEGF) in the eye.

5. A pharmaceutical composition comprising the isolated anti-VEGF vNAR protein selected from the group consisting of V19 and V32R of claim 1, and a pharmaceutically acceptable excipient.

6. The pharmaceutical composition of claim 5, wherein it is formulated for topical administration.

7. The pharmaceutical composition of claim 5, wherein the composition is formulated for topical ophthalmic administration.

8. The pharmaceutical composition of claim 5, wherein the composition is formulated for topical administration in a VEGF-related eye disease.

9. The pharmaceutical composition of claim 8, wherein the VEGF-related eye disease is selected from wet age-related macular degeneration, diabetic retinopathy, or neovascular glaucoma.

10. A medicament comprising an effective amount of an isolated anti-VEGF vNAR protein comprising the amino acid sequence of SEQ ID NO: 4 (V19) or SEQ ID NO: 6 (V32R), administrable by a topical ophthalmic route.

11. A method treating a VEGF-related eye disease, wherein the disease is also a pathology related to an angiogenic process, where excessive angiogenesis occurs when diseased cells produce abnormal amounts of VEGF or VEGF receptors, the method comprising applying the medicament of claim 10.

12. The method of claim 11, wherein the angiogenic process is selected from the group consisting of age related macular degeneration, diabetic retinopathy, and neovascular glaucoma.

13. The method of claim 12, wherein the angiogenic process is diabetic retinopathy.

14. The method of claim 12, wherein the angiogenic process is wet age-related macular degeneration.

15. The method of claim 12, wherein the angiogenic process is neovascular glaucoma.

16. A method for preparing a medicament comprising an anti-VEGF vNAR protein of claim 1, the method comprising the step of culturing a host cell to produce the anti-VEGF vNAR protein V19 comprising the amino acid sequence of SEQ ID NO: 4 or the anti-VEGF vNAR protein V32R comprising the amino acid sequence of SEQ ID NO: 6.

17. The method of claim 16, wherein the ophthalmic condition is wet age-related macular degeneration, diabetic retinopathy, or neovascular glaucoma.

18. An isolated anti-VEGF vNAR protein selected from the group consisting of V19 and V32R of claim 1, wherein,
    (a) it originates from *Orectolobus maculatus* or *Heterodontus francisci;*
    (b) it binds to and neutralizes the activity of the vascular endothelial growth factor (VEGF) in the eye;
    (c) wherein the following vNAR V19 residues in CDR zone are able to interact with the following VEGF residues:
        i. ARG 101 of V19 interacts with GLU 17 of VEGF,
        ii. GLU103 of V 19 interacts with ARG 10 of VEGF; and,
    (d) wherein the following vNAR V32R residues in CDR zone are able to interact with the following VEGF residues:
        i. GLU 98 of V32R interacts with ARG 43 and GLN 24 of VEGF;
        ii. ARG 91 of V32R interacts with GLN 24 and ASP 21 of VEGF;
        iii. HIS 90 of V32R interacts with PHE 23 of VEGF;
        iv. LYS 95 of V32R interacts with GLU 25 of VEGF;
        v. ARG 100 of V32R interacts with GLU 54 of VEGF; and,
        vi. TYR104 of V32R interacts with CYS55 of VEGF.

19. A process for producing an anti-VEGF vNAR protein of claim 1, said process comprising the steps of:
    a) obtaining a vector comprising the DNA sequence of SEQ ID NO: 3 encoding V19 or the DNA sequence of SEQ ID NO: 5 encoding V32R;
    b) obtaining a host cell comprising said vector; and,
    c) culturing the host cell to produce the anti-VEGF vNAR protein V19 comprising the amino acid sequence of SEQ ID NO: 4 or the anti-VEGF vNAR protein V32 comprising the amino acid sequence of SEQ ID NO: 6.

* * * * *

SEQUENCE LISTING

```
<160> NUMBER OF SEQ ID NOS: 17

<210> SEQ ID NO 1
<211> LENGTH: 368
<212> TYPE: DNA
<213> ORGANISM: Heterodontus francisci

<400> SEQUENCE: 1
gcaagcctgg accaaacacc aagaacggca acgagagaga caggcgaatc cctgagcatt      60
aactgcgtcc tcactgatac tagccatatt ttgttcggca caaaatggct ctggaataat     120
ccgggttcaa cagattggga aagcataacg attggcggac gatatgctga atcagtcaac     180
aaccaagcaa agtcattttc tctgcaaatc aaggacctga cagttgaaga cagtggcacc     240
tattactgca agcgcaaacc ataggaagac gcaaaaatct acttccacgc ccattggtga     300
acggtatagc tgcgatgggg tatagctcca gtgactacga cggagctggc accgtgctga     360
ctgtgaac                                                              368

<210> SEQ ID NO 2
<211> LENGTH: 123
<212> TYPE: PRT
<213> ORGANISM: Heterodontus francisci

<400> SEQUENCE: 2

Ala Ser Leu Asp Gln Thr Pro Arg Thr Ala Thr Arg Glu Thr Gly Glu
1               5                   10                  15

Ser Leu Ser Ile Asn Cys Val Leu Thr Asp Thr Ser His Ile Leu Phe
            20                  25                  30

Gly Thr Lys Trp Leu Trp Asn Asn Pro Gly Ser Thr Asp Trp Glu Ser
        35                  40                  45

Ile Thr Ile Gly Gly Arg Tyr Ala Glu Ser Val Asn Asn Gln Ala Lys
    50                  55                  60

Ser Phe Ser Leu Gln Ile Lys Asp Leu Thr Val Glu Asp Ser Gly Thr
```

```
                65                  70                  75                  80
Tyr Tyr Cys Lys Ala Gln Thr Ile Gly Arg Arg Lys Asn Leu Leu Pro
                    85                  90                  95
Arg Pro Leu Val Asn Gly Ile Ala Ala Met Gly Tyr Ser Ser Ser Asp
                100                 105                 110
Tyr Asp Gly Ala Gly Thr Val Leu Thr Val Asn
        115                 120

<210> SEQ ID NO 3
<211> LENGTH: 339
<212> TYPE: DNA
<213> ORGANISM: Orectolobus maculatus

<400> SEQUENCE: 3
caacgggttg aacaaacacc aagaacagca acaaaagaga cgggcgaatc actgaccatc      60
aactgcgtcc taagagatgc tagttttgaa ttaaaagaca cgggctggta tcggacaaaa     120
ttgggttcaa caaatgagca gagtatatca attggcggac gatatgttga acagtcaac      180 aagggatcaa agtcctttc tctgagaatt agtgatctga gagttgaaga cagtggcacg     240
tataagtgtc aagcattcta ttctcttccg ttgggcgatt acaactattc tctgctgttt     300
aggggtgaga aggagctgg caccgtgctg actgtgaac                              339

<210> SEQ ID NO 4
<211> LENGTH: 114
<212> TYPE: PRT
<213> ORGANISM: Orectolobus maculatus

<400> SEQUENCE: 4

Ala Gln Arg Val Glu Gln Thr Pro Arg Thr Ala Thr Lys Glu Thr Gly
1               5                   10                  15
Glu Ser Leu Thr Ile Asn Cys Val Leu Arg Asp Ala Ser Phe Glu Leu
            20                  25                  30
Lys Asp Thr Gly Trp Tyr Arg Thr Lys Leu Gly Ser Thr Asn Glu Gln
        35                  40                  45
Ser Ile Ser Ile Gly Gly Arg Tyr Val Glu Thr Val Asn Lys Gly Ser
    50                  55                  60
Lys Ser Phe Ser Leu Arg Ile Ser Asp Leu Arg Val Glu Asp Ser Gly
65                  70                  75                  80
Thr Tyr Lys Cys Gln Ala Phe Tyr Ser Leu Pro Leu Gly Asp Tyr Asn
                85                  90                  95
Tyr Ser Leu Leu Phe Arg Gly Glu Lys Gly Ala Gly Thr Val Leu Thr
                100                 105                 110
Val Asn

<210> SEQ ID NO 5
<211> LENGTH: 342
<212> TYPE: DNA
<213> ORGANISM: Heterodontus francisci

<400> SEQUENCE: 5
gcaagcctgg accaaacacc aagaacggca acgagagaga cgggcgaatc cctgaccatt      60
aactgcgtct tcactgattc tagctgtggt ttgtgcggca catcttggtt ccggaataat     120
ccgggttcaa cagattggga acgcataacg attggcggac gatatgttga atcagtcaac     180
aagggagcaa agtcatttc tctgcaaatc aaggacctga cagttgaaga cagtgtcacc     240
tattactgca aagcgcaagg tcatcgatac ttcagtaagg tgtgcgagct gcgatgtccc    300
```
agttactact acgacggagc tggcaccgtg ctgactgtga ac           342

<210> SEQ ID NO 6
<211> LENGTH: 115
<212> TYPE: PRT
<213> ORGANISM: Heterodontus francisci

<400> SEQUENCE: 6

Ala Ala Ser Leu Asp Gln Thr Pro Arg Thr Ala Thr Arg Glu Thr Gly
1               5                   10                  15

Glu Ser Leu Thr Ile Asn Cys Val Phe Thr Asp Ser Ser Cys Gly Leu
            20                  25                  30

Cys Gly Thr Ser Trp Phe Arg Asn Asn Pro Gly Ser Thr Asp Trp Glu
        35                  40                  45

Arg Ile Thr Ile Gly Gly Arg Tyr Val Glu Ser Val Asn Lys Gly Ala
    50                  55                  60

Lys Ser Phe Ser Leu Gln Ile Lys Asp Leu Thr Val Glu Asp Ser Val
65                  70                  75                  80

Thr Tyr Tyr Cys Lys Ala Gln Gly His Arg Tyr Phe Ser Lys Val Cys
                85                  90                  95

Glu Leu Arg Cys Pro Ser Tyr Tyr Asp Gly Ala Gly Thr Val Leu
            100                 105                 110

Thr Val Asn
        115

<210> SEQ ID NO 7
<211> LENGTH: 94
<212> TYPE: PRT
<213> ORGANISM: Homo sapiens

<400> SEQUENCE: 7

Val Val Lys Phe Met Asp Val Tyr Gln Arg Ser Tyr Cys His Pro Ile
1               5                   10                  15

Glu Thr Leu Val Asp Ile Phe Gln Glu Tyr Pro Asp Glu Ile Glu Tyr
            20                  25                  30

Ile Phe Lys Pro Ser Cys Val Pro Leu Met Arg Cys Gly Gly Cys Cys
        35                  40                  45

Asn Asp Glu Gly Leu Glu Cys Val Pro Thr Glu Glu Ser Asn Ile Thr
    50                  55                  60

Met Gln Ile Met Arg Ile Lys Pro His Gln Gly Gln His Ile Gly Glu
65                  70                  75                  80

Met Ser Phe Leu Gln His Asn Lys Cys Glu Cys Arg Pro Lys
                85                  90

<210> SEQ ID NO 8
<211> LENGTH: 113
<212> TYPE: PRT
<213> ORGANISM: Orectolobus maculatus

<400> SEQUENCE: 8

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys

```
                50                  55                  60
Ser Phe Ser Leu Arg Ile Ser Asp Leu Arg Val Glu Asp Ser Gly Thr
 65                  70                  75                  80

Tyr Lys Cys Gln Ala Phe Tyr Ser Leu Pro Leu Gly Asp Tyr Asn Tyr
                 85                  90                  95

Ser Leu Leu Phe Arg Gly Glu Lys Gly Ala Gly Thr Val Leu Thr Val
                100                 105                 110

Lys

<210> SEQ ID NO 9
<211> LENGTH: 121
<212> TYPE: PRT
<213> ORGANISM: Heterodontus francisci

<400> SEQUENCE: 9

Met Ala Ala Ser Leu Asp Gln Thr Pro Arg Thr Ala Thr Arg Glu Thr
 1               5                  10                  15

Gly Glu Ser Leu Thr Ile Asn Cys Val Phe Thr Asp Ser Ser Cys Gly
                 20                  25                  30

Leu Cys Gly Thr Ser Trp Phe Arg Asn Asn Pro Gly Ser Thr Asp Trp
             35                  40                  45

Glu Arg Ile Thr Ile Gly Gly Arg Tyr Val Glu Ser Val Asn Lys Gly
 50                  55                  60

Ala Lys Ser Phe Ser Leu Gln Ile Lys Asp Leu Thr Val Glu Asp Ser
 65                  70                  75                  80

Val Thr Tyr Tyr Cys Lys Ala Gln Gly His Arg Tyr Phe Ser Lys Val
                 85                  90                  95

Cys Glu Leu Arg Cys Pro Ser Tyr Tyr Tyr Asp Gly Ala Gly Thr Val
                100                 105                 110

Leu Thr Val Asn Gly Gln Ala Gly Gln
            115                 120

<210> SEQ ID NO 10
<211> LENGTH: 26
<212> TYPE: DNA
<213> ORGANISM: Unknown
<220> FEATURE:
<223> OTHER INFORMATION: Elasmobranchii

<400> SEQUENCE: 10
gttcacagtc agcacggtgc cagctc                                        26

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
caacgggttg aacaaacacc                                               20

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
```

```
                                    -continued caacgggttg aacaaacacc                                                        20

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
acaagggtag accaaacacc                                                        20

<210> SEQ ID NO 14
<211> LENGTH: 20
<212> TYPE: DNA
<213> ORGANISM: Artificial sequence
<220> FEATURE:
<223> OTHER INFORMATION: Synthetic

<400> SEQUENCE: 14
gcaagggtgg accaaacacc                                                        20

<210> SEQ ID NO 15
<211> LENGTH: 20
<212> TYPE: DNA
<213> ORGANISM: Artificial sequence
<220> FEATURE:
<223> OTHER INFORMATION: Synthetic

<400> SEQUENCE: 15
gcatgggtag accaaacacc                                                        20

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
gcaagcctgg accaaacacc                                                        20

<210> SEQ ID NO 17
<211> LENGTH: 20
<212> TYPE: DNA
<213> ORGANISM: Artificial sequence
<220> FEATURE:
<223> OTHER INFORMATION: Synthetic

<400> SEQUENCE: 17
gcattgacgg accaaacacc                                                        20
```